(12) United States Patent
Vogels et al.

(10) Patent No.: US 6,492,169 B1
(45) Date of Patent: Dec. 10, 2002

(54) COMPLEMENTING CELL LINES

(75) Inventors: Ronald Vogels, Linschoren (NL); Menzo Havenga, Alphen aas den Rijn (NL); Majid Mehtali, Plobsheim (FR)

(73) Assignee: Crucell Holland, B.V., Leiden (NL)

( * ) Notice: Subject to any disclaimer, the term of this patent is extended or adjusted under 35 U.S.C. 154(b) by 0 days.

(21) Appl. No.: 09/713,678

(22) Filed: Nov. 15, 2000

Related U.S. Application Data

(63) Continuation-in-part of application No. 09/573,740, filed on May 18, 2000.
(60) Provisional application No. 60/134,764, filed on May 18, 1999.

(51) Int. Cl.[7] .............................. C12N 5/02; C12N 7/00; C12N 15/63
(52) U.S. Cl. ...................... 435/325; 435/69.1; 435/455; 435/235.1
(58) Field of Search ................................ 435/325, 69.1, 435/320.1, 455, 235.1; 536/23.1

(56) References Cited

U.S. PATENT DOCUMENTS

| | | | | |
|---|---|---|---|---|
| 5,849,561 A | * | 12/1998 | Falck-Pedersen | 435/235.1 |
| 5,994,128 A | * | 11/1999 | Fallaux et al. | 435/325 |
| 6,033,908 A | * | 3/2000 | Bout et al. | 435/325 |
| 6,306,652 B1 | * | 10/2001 | Fallaux et al. | 435/325 |

OTHER PUBLICATIONS

Abrahamsen et al. Journal of Virology. 1997; 71 (11): 8946–8951.*

* cited by examiner

*Primary Examiner*—James Housel
*Assistant Examiner*—Shanon A Foley
(74) *Attorney, Agent, or Firm*—TraskBritt

(57) ABSTRACT

A packaging cell line capable of complemention recombinant adenoviruses based on serotypes from subgroup B, preferably adenovirus type 35. The cell line is preferably human embryonic kidney cells and primary human amniocytes) which are transformed by adenovirus E1 sequences either operatively linked on one DNA molecule or located on two separate DNA molecules, the sequences being operatively linked to regulatory sequences enabling transcription and translation of encoded proteins.

7 Claims, 36 Drawing Sheets

% of human sera with neutralising capacity for human adenovirus (n=100)

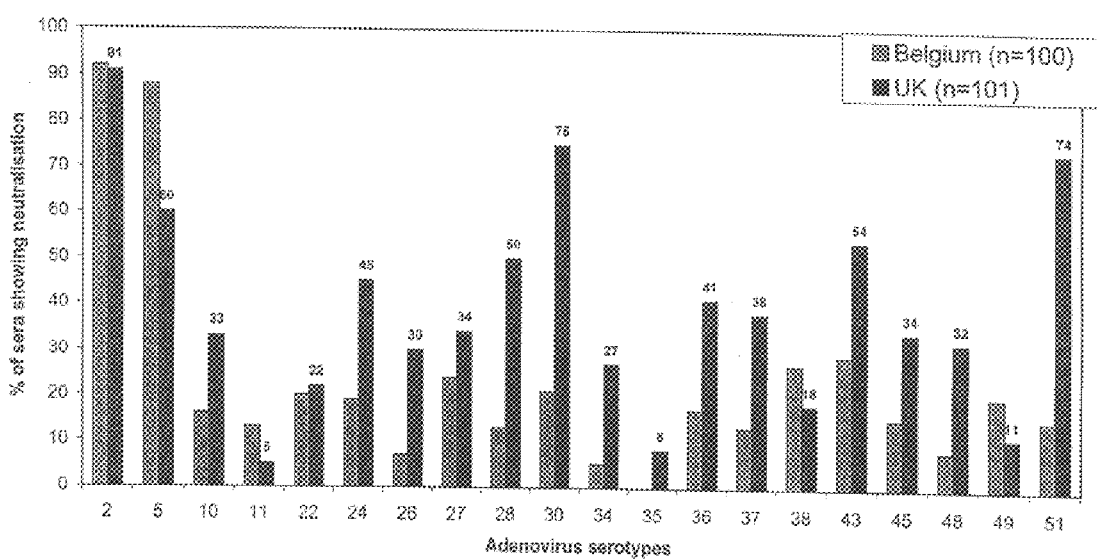

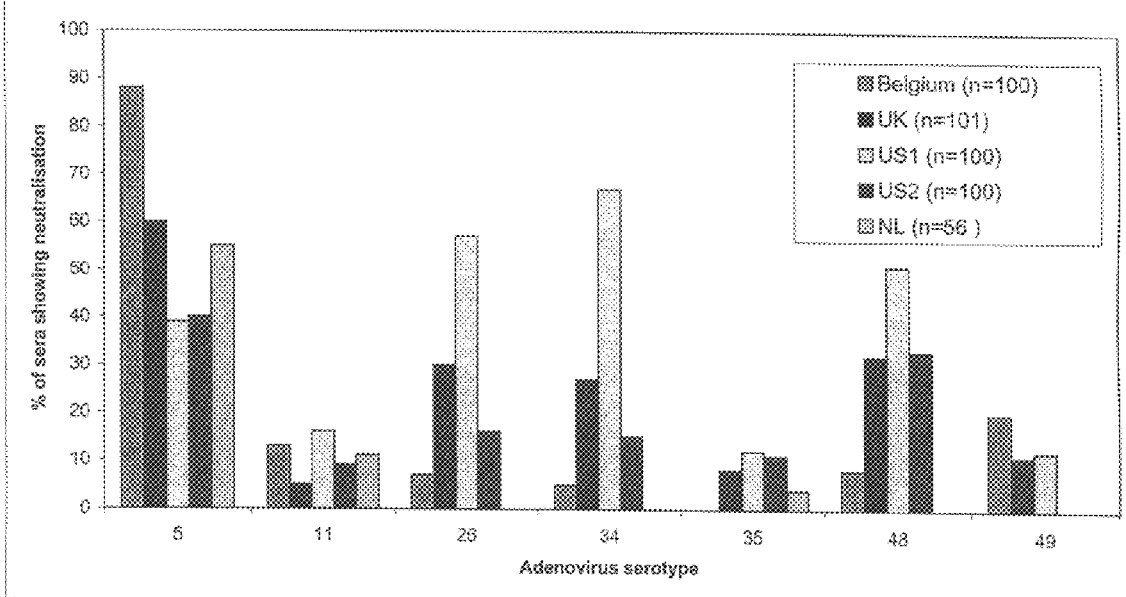

Figure 5A Sequence of Adenovirus serotype 35.

```
   1 CATCATCAAT AATATACCTT ATAGATGGAA TGGTGCCAAT ATGTAAATGA GGTGATTTTA AAAAGTGTGG
  71 GCCGTGTGGT GATTGGCTGT GGGGTTAACG GTTAAAAGGG GCGGCGCGGC CGTGGGAAAA TGACGTTTTA
 141 TGGGGGTGGA GTTTTTTTGC AAGTTGTCGC GGGAAATGTT ACGCATAAAA AGGCTTCTTT TCTCACGGAA
 211 CTACTTAGTT TTCCCACGGT ATTTAACAGG AAATGAGGTA GTTTTGACCG GATGCAAGTG AAAATTGCTG
 281 ATTTTCGCGC GAAAACTGAA TGAGGAAGTG TTTTTCTGAA TAATGTGGTA TTTATGGCAG GGTGGAGTAT
 351 TTGTTCAGGG CCAGGTAGAC TTTGACCCAT TACGTGGAGG TTTCGATTAC CGTGTTTTTT ACCTGAATTT
 421 CCGCGTACCG TGTCAAAGTC TTCTGTTTTT ACGTAGGTGT CAGCTGATCG CTAGGGTATT TATACCTCAG
 491 GGTTTGTGTC AAGAGGCCAC TCTTGAGTGC CAGCGAGAAG AGTTTTCTCC TCTGCGCCGG CAGTTTAATA
 561 ATAAAAAAAT GAGAGATTTG CGATTTCTGC CTCAGGAAAT AATCTCTGCT GAGACTGAAA ATGAAATATT
 631 GGAGCTTGTG GTGCACGCCC TGATGGAGA CGATCCGGAG CCACCTGTGC AGCTTTTTGA GCCTCCTACG
 701 CTTCAGGAAC TGTATGATTT AGAGGTAGAG GGATCGGAGG ATTCTAATGA GGAAGCTGTG AATGGCTTTT
 771 TTACCGATTC TATGCTTTTA GCTGCTAATG AAGGATTAGA ATTAGATCCG CCTTTGGACA CTTTCAATAC
 841 TCCAGGGGTG ATTGTGGAAA GCGGTACAGG TGTAAGAAAA TTACCTGATT TGAGTTCCGT GGACTGTGAT
 911 TTGCACTGCT ATGAAGACGG GTTTCCTCCG AGTGATGAGG AGGACCATGA AAAGGAGCAG TCCATGCAGA
 981 CTGCAGCGGG TGAGGGAGTG AAGGCTGCCA ATGTTGGTTT TCAGTTGGAT TGCCCGGAGC TTCCTGGACA
1051 TGGCTGTAAG TCTTGTGAAT TTCACAGGAA AAATACTGGA GTAAAGGAAC TGTTATGTTC GCTTTGTTAT
1121 ATGAGAACGC ACTGCCACTT TATTTACAGT AAGTGTGTTT AAGTTAAAAT TTAAAGGAAT ATGCTGTTTT
1191 TCACATGTAT ATTGAGTGTG AGTTTTGTGC TTCTTATTAT AGGTCGTGTG TCTGATGCTG ATGAATCACC
1261 ATCTCCTGAT TCTACTACCT CACCTCCTGA TATTCAAGCA CCTGTTCCTG TGGACGTGCG CAAGCCCATT
1331 CCTGTGAAGC TTAAGCCTGG GAAACGTCCA GCAGTGGAGA AACTTGAGGA CTTGTTACAG GGTGGGGACG
1401 GACCTTTGGA CTTGAGTACA CGGAAACGTC CAAGACAATA AGTGTTCCAT ATCCGTGTTT ACTTAAGGTG
1471 ACGTCAATAT TTGTGTGAGA GTGCAATGTA ATAAAAATAT GTTAACTGTT CACTGGTTTT TATTGCTTTT
1541 TGGGCGGGGA CTCAGGTATA TAAGTAGAAG CAGACCTGTG TGGTTAGCTC ATAGGAGCTG GCTTTCATCC
1611 ATGGAGGTTT GGGCCATTTT GGAAGACCTT AGGAAGACTA GGCAACTGTT AGAGAGCGCT TCGGACGGAG
1681 TCTCCGGTTT TTGGAGATTC TGGTTCGCTA GTGAATTAGC TAGGGTAGTT TTTAGGATAA AACAGGACTA
1751 TAAACAAGAA TTTGAAAAGT TGTTGGTAGA TTGCCCAGGA CTTTTTGAAG CTCTTAATTT GGGCCATCAG
1821 GTTCACTTTA AAGAAAAAGT TTTATCAGTT TTAGACTTTT CAACCCCAGG TAGAACTGCT GCTGCTGTGG
1891 CTTTTCTTAC TTTTATATTA GATAAATGGA TCCCGCAGAC TCATTTCAGC AGGGGATACG TTTTGGATTT
1961 CATAGCCACA GCATTGTGGA GAACATGGAA GGTTCGCAAG ATGAGGACAA TCTTAGGTTA CTGGCCAGTG
2031 CAGCCTTTGG GTGTAGCGGG AATCCTGAGG CATCCACCGG TCATGCCAGC GGTTCTGGAG GAGGAACAGC
2101 AAGAGGACAA CCCGAGAGCC GGCCTGGACC CTCCAGTGGA GGAGGCGGAG TAGCTGACTT GTCTCCTGAA
2171 CTGCAACGGG TGCTTACTGG ATCTACGTCC ACTGACGGG ATAGGGGCGT TAAGAGGGAG AGGGCATCCA
2241 GTGGTACTGA TGCTAGATCT GAGTTGGCTT TAAGTTTAAT GAGTCGCAGA CGTCCTGAAA CCATTTGGTG
2311 GCATGAGGTT CAGAAAGAGG GAAGGGATGA AGTTTCTGTA TTGCAGGAGA AATATTCACT GGAACAGGTG
2381 AAAACATGTT GGTTGGAGCC AGAGGATGAT TGGGCGGTGG CCATTAAAAA TTATGCCAAG ATAGCTTTGA
2451 GGCCTGATAA ACAGTATAAG ATCAGTAGAC GGATTAATAT CCGGAATGCT TGTTACATAT CTGGAAATGG
2521 GGCTGAGGTG GTAATAGATA CTCAAGACAA GACAGTTATT AGATGCTGCA TGATGGATAT GTGGCCTGGA
2591 GTAGTCGGTA TGGAAGCAGT CACTTTGTA AATGTTAAGT TTAGGGGAGA TGGTTATAAT GGAATAGTGT
2661 TTATGGCCAA TACCAAACTT ATATTGCATG GTTGTAGCTT TTTTGGTTTC AACAATACCT GTGTAGATGC
2731 CTGGGGACAG GTTAGTGTAC GGGGGTGTAG TTTCTATGCG TGTTGGATTG CCACAGCTGG CAGAACCAAG
2801 AGTCAATTGT CTCTGAAGAA ATGCATATTC CAAAGATGTA ACCTGGGCAT TCTGAATGAA GGCGAAGCAA
2871 GGGTCCGTCA CTGCGCTTCT ACAGATACTG GATGTTTTAT TTTAATTAAG GGAAATGCCA GCGTAAAGCA
2941 TAACATGATT TGTGGTGCTT CCGATGAGAG GCCTTATCAA ATGCTCACTT GTGCTGGTGG GCATTGTAAT
3011 ATGCTGGCTA CTGTGCATAT TGTTTCCCAT CAACGCAAAA AATGGCCTGT TTTGATCAC AATGTGTTGA
3081 CCAAGTGCAC CATGCATGCA GGTGGGCGTA GAGGAATGTT TATGCCTTAC CAGTGTAACA TGAATCATGT
3151 GAAAGTGTTG TTGGAACCAG ATGCCTTTTC CAGAATGAGC CTAACAGGAA TCTTTGACAT GAACACGCAA
3221 ATCTGGAAGA TCCTGAGGTA TGATGATACG AGATCGAGGG TGCGCGCATG CGAATGCGGA GGCAAGCATG
3291 CCAGGTTCCA GCCGGTGTGT GTAGATGTGA CCGAAGATCT CAGACCGGAT CATTTGGTTA TTGCCCGCAC
3361 TGGAGCAGAG TTCGGATCCA GTGGAGAAGA AACTGACTAA GGTGAGTATT GGGAAAACTT TGGGGTGGGA
3431 TTTTCAGATG GACAGATTGA GTAAAAATTT GTTTTTTCTG TCTTGCAGCT GACATGAGTG GAAATGCTTC
3501 TTTTAAGGGG GGAGTCTTCA GCCCTTATCT GACAGGGCGT CTCCCATCCT GGGCAGGAGT TCGTCAGAAT
3571 GTTATGGGAT CTACTGTGGA TGGAAGACCC GTTCAACCCG CCAATTCTTC AACGCTGACC TATGCTACTT
3641 TAAGTTCTTC ACCTTTGGAC GCAGCTGCAG CCGCTGCCGC CGCCTCTGTC GCCGCTAACA CTGTGCTTGG
3711 AATGGGTTAC TATGGAAGCA TCGTGGCTAA TTCCACTTCC TCTAATAACC CTTCTACACT GACTCAGGAC
3781 AAGTTACTTG TCCTTTTGGC CCAGCTGGAG GCTTTGACCC AACGTCTGGG TGAACTTTCT CAGCAGGTGG
```

Figure 5B

```
3851 CCGAGTTGCG AGTACAAACT GAGTCTGCTG TCGGCACGGC AAAGTCTAAA TAAAAAAAAT TCCAGAATCA
3921 ATGAATAAAT AAACGAGCTT GTTGTTGATT TAAAATCAAG TGTTTTTATT TCATTTTTCG CGCACGGTAT
3991 GCCCTGGACC ACCGATCTCG ATCATTGAGA ACTCGGTGGA TTTTTTCCAG AATCCTATAG AGGTGGGATT
4061 GAATGTTTAG ATACATGGGC ATTAGGCCGT CTTTGGGGTG GAGATAGCTC CATTGAAGGG ATTCATGCTC
4131 CGGGGTAGTG TTGTAAATCA CCCAGTCATA ACAAGGTCGC AGTGCATGGT GTTGCACAAT ATCTTTTAGA
4201 AGTAGGCTGA TTGCCACAGA TAAGCCCTTG GTGTAGGTGT TTACAAACCG GTTGAGCTGG GAGGGGTGCA
4271 TTCGAGGTGA AATTATGTGC ATTTTGGATT GGATTTTTAA GTTGGCAATA TTGCCGCCAA GATCCCGTCT
4341 TGGGTTCATG TTATGAAGGA CTACCAAGAC GGTGTATCCG GTACATTTAG GAAATTTATC GTGCAGCTTG
4411 GATGGAAAAG CGTGGAAAAA TTTGGAGACA CCCTTGTGTC CTCCGAGATT TTCCATGCAC TCATCCATGA
4481 TAATAGCAAT GGGGCCGTGG GCAGCGGCGC GGGCAAACAC GTTCCGTGGG TCTGACACAT CATAGTTATG
4551 TTCCTGAGTT AAATCATCAT AAGCCATTTT AATGAATTTG GGGCGGAGCG TACCGATTG GGGTATGAAT
4621 GTTCCTTCGG GCCCCGGAGC ATAGTTCCCC TCACAGATTT GCATTTCCCA AGCTTTCAGT TCTGAGGGTG
4691 GAATCATGTC CACCTGGGGG GCTATGAAGA ACACCGTTTC GGGGGCGGGG GTGATTAGTT GGGATGATAG
4761 CAAGTTTCTG AGCAATTGAG ATTTGCCACA TCCGGTGGGG CCATAAATAA TTCCGATTAC AGGTTGCAGG
4831 TGGTAGTTTA GGGAACGGCA ACTGCCGTCT TCTCGAAGCA AGGGGGCCAC CTCGTTCATC ATTTCCCTTA
4901 CATGCATATT TTCCCGCACC AAATCCATTA GGAGGCGCTC TCCTCCTAGT GATAGAAGTT CTTGTAGTGA
4971 GGAAAAGTTT TTCAGCGGTT TTAGACCGTC AGCCATGGGC ATTTTGGAAA GAGTTTGCTG CAAAAGTTCT
5041 AGTCTGTTCC ACAGTTCAGT GATGTGTTCT ATGGCATCTC GATCCAGCAG ACCTCCTCGT TTCGCGGGTT
5111 TGGACGGCTC CTGGAGTAGG GTATGAGACG ATGGGCGTCC AGCGCTGCCA GGGTTCGGTC CTTCCAGGGT
5181 CTCAGTGTTC GAGTCAGGGT TGTTTCCGTC ACAGTGAAGG GGTGTGCGCC TGCTTGGGCG CTTGCCAGGG
5251 TGCGCTTCAG ACTCATTCTG CTGGTGGAGA ACTTCTGTCG CTTGGCGCCC TGTATGTCGG CCAAGTAGCA
5321 GTTTACCATG AGTTCGTAGT TGAGCGCCTC GGCTGCGTGG CCTTTGGCGC GGAGCTTACC TTTGGAAGTT
5391 TTCTTGCATA CCGGGCAGTA TAGGCATTTC AGCGCATACA GCTTGGGCGC AAGGAAAATG GATTCTGGGG
5461 AGTATGCATC CGCGCCGCAG GAGGCGCAAA CAGTTTCACA TTCCACCAGC CAGGTTAAAT CCGGTTCATT
5531 GGGGTCAAAA ACAAGTTTTC CGCCATATTT TTTGATGCGT TTCTTACCTT TGGTCTCCAT AAGTTCGTGT
5601 CCTCGTTGAG TGACAAACAG GCTGTCCGTA TCTCCGTAGA CTGATTTTAC AGGCCTCTTC TCCAGTGGAG
5671 TGCCTCGGTC TTCTTCGTAC AGGAACTCTG ACCACTCTGA TACAAAGGCG CGCGTCCAGG CCAGCACAAA
5741 GGAGGCTATG TGGGAGGGGT AGCGATCGTT GTCAACCAGG GGGTCCACCT TTTCCAAAGT ATGCAAACAC
5811 ATGTCACCCT CTTCAACATC CAGGAATGTG ATTGGCTTGT AGGTGTATTT CACGTGACCT GGGGTCCCCG
5881 CTGGGGGGGT ATAAAAGGGG GCGGTTCTTT GCTCTTCCTC ACTGTCTTCC GGATCGCTGT CCAGGAACGT
5951 CAGCTGTTGG GGTAGGTATT CCCTCTCGAA GGCGGGCATG ACCTCTGCAC TCAGGTTGTC AGTTTCTAAG
6021 AACGAGGAGG ATTTGATATT GACAGTGCCG GTTGAGATGC CTTTCATGAG GTTTCGTCC ATTTGGTCAG
6091 AAAACACAAT TTTTTTATTG TCAAGTTTGG TGGCAAATGA TCCATACAGG GCGTTGGATA AAAGTTTGGC
6161 AATGGATCGC ATGGTTTGGT TCTTTTCCTT GTCCGCGCGC TCTTTGGCGG CGATGTTGAG TTGGACATAC
6231 TCGCGTGCCA GGCACTTCCA TTCGGGGAAG ATAGTTGTTA ATTCATCTGG CACGATTCTC ACTTGCCACC
6301 CTCGATTATG CAAGGTAATT AAATCCACAC TGGTGGCCAC CTCGCCTCGA AGGGGTTCAT TGGTCCAACA
6371 GAGCCTACCT CCTTTCCTAG AACAGAAAGG GGGAAGTGGG TCTAGCATAA GTTCATCGGG AGGGTCTGCA
6441 TCCATGGTAA AGATTCCCGG AAGTAAATCC TTATCAAAAT AGCTGATGGG AGTGGGGTCA TCTAAGGCCA
6511 TTTGCCATTC TCGAGCTGCC AGTGCGCGCT CATATGGGTT AAGGGGACTG CCCCAGGGCA TGGGATGGGT
6581 GAGAGCAGAG GCATACATGC CACAGATGTC ATAGACGTAG ATGGGATCCT CAAAGATGCC TATGTAGGTT
6651 GGATAGCATC GCCCCCCTCT GATACTTGCT CATATAGTTC CGCACATAGT ATGTGATGGC GCTAGCAGCC
6721 CCGGACCCAA GTTGGTGCGA TTGGGTTTTT CTGTTCTGTA GACGATCTGG CGAAAGATGG CGTGAGAATT
6791 GGAAGAGATG GTGGGTCTTT GAAAAATGTT GAAATGGGCA TGAGGTAGAC CTACAGAGTC TCTGACAAAG
6861 TGGGCATAAG ATTCTTGAAG CTTGGTTACC AGTTCGGCGG TGACAAGTAC GTCTAGGGCG CAGTAGTCAA
6931 GTGTTTCTTG AATGATGTCA TAACCTGGTT GGTTTTTCTT TTCCCACAGT TCGCGGTTGA GAAGGTATTC
7001 TTCGCGATCC TTCCAGTACT CTTCTAGCGG AAACCCGTCT TTGTCTGCAC GGTAAGATCC TAGCATGTAG
7071 AACTGATTAA CTGCCTTGTA AGGGCAGCAG CCCTTCTCTA CGGGTAGAGA GTATGCTTGA GCAGCTTTTC
7141 GTAGCGAAGC GTGAGTAAGG GCAAAGGTGT CTCTGACCAT GACTTTGAGA AATTGGTATT TGAAGTCCAT
7211 GTCGTCACAG GCTCCCTGTT CCCAGAGTTG GAAGTCTACC CGTTTCTTGT AGGCGGGGTT GGGCAAAGCG
7281 AAAGTAACAT CATTGAAGAG AATCTTACCG GCTCTGGGCA TAAAATTGCG AGTGATGCGG AAAGGCTGTG
7351 GTACTTCCGC TCGATTGTTG ATCACCTGGG CAGCTAGGAC GATTTCGTCG AAACCGTTGA TGTTGTGTCC
7421 TACGATGTAT AATTCTATGA AACGCGGCGT GCCTCTGACG TGAGGTAGCT TACTGAGCTC ATCAAAGGTT
7491 AGGTCTGTGG GGTCAGATAA GGCGTAGTGT TCGAGAGCCC ATTCGTGCAG GTGAGGATTT GCATGTAGGA
7561 ATGATGACCA AAGATCTACC GCCAGTGCTG TTTGTAACTG GTCCCGATAC TGACGAAAAT GCCGGCCAAT
7631 TGCCATTTTT TCTGGAGTGA CACAGTAGAA GGTTCTGGGG TCTTGTTGCC ATCGATCCCA CTTGAGTTTA
7701 ATGGCTAGAT CGTGGGCCAT GTTGACGAGA CGCTCTTCTC CTGAGAGTTT CATGACCAGC ATGAAAGGAA
7771 CTAGTTGTTT GCCAAAGGAT CCCATCCAGG TGTAAGTTTC CACATCGTAG GTCAGGAAGA GTCTTTCTGT
```

Figure 5C

```
 7841 GCGAGGATGA GAGCCGATCG GGAAGAACTG GATTTCCTGC CACCAGTTGG AGGATTGGCT GTTGATGTGA
 7911 TGGAAGTAGA AGTTTCTGCG GCGCGCCGAG CATTCGTGTT TGTGCTTGTA CAGACGGCCG CAGTAGTCGC
 7981 AGCGTTGCAC GGGTTGTATC TCGTGAATGA GCTGTACCTG GCTTCCCTTG ACGAGAAATT TCAGTGGGAA
 8051 GCCGAGGCCT GGCGATTGTA TCTCGTGCTC TTCTATATTC GCTGTATCGG CCTGTTCATC TTCTGTTTCG
 8121 ATGGTGGTCA TGCTGACGAG CCCCCGCGGG AGGCAAGTCC AGACCTCGGC GCGGGAGGGG CGGAGCTGAA
 8191 GGACGAGAGC GCGCAGGCTG GAGCTGTCCA GAGTCCTGAG ACGCTGCGGA CTCAGGTTAG TAGGTAGGGA
 8261 CAGAAGATTA ACTTGCATGA TCTTTTCCAG GGCGTGCGGG AGGTTCAGAT GGTACTTGAT TTCCACAGGT
 8331 TCGTTTGTAG AGACGTCAAT GGCTTGCAGG GTTCCGTGTC CTTTGGGCGC CACTACCGTA CCTTTGTTTT
 8401 TTCTTTTGAT CGGTGGTGGC TCTCTTGCTT CTTGCATGCT CAGAAGCGGT GACGGGGACG CGCGCCGGGC
 8471 GGCAGCGGTT GTTCCGGACC CGGGGGCATG GCTGGTAGTG GCACGTCGGC GCCGCGCACG GGCAGGTTCT
 8541 GGTATTGCGC TCTGAGAAGA CTTGCGTGCG CCACCACGCG TCGATTGACG TCTTGTATCT GACGTCTCTG
 8611 GGTGAAAGCT ACCGGCCCCG TGAGCTTGAA CCTGAAAGAG AGTTCAACAG AATCAATTTC GGTATCGTTA
 8681 ACGGCAGCTT GTCTCAGTAT TTCTTGTACG TCACCAGAGT TGTCCTGGTA GGCGATCTCC GCCATGAACT
 8751 GCTCGATTTC TTCCTCCTGA AGATCTCCGC GACCCGCTCT TTCGACGGTG GCCGCGAGGT CATTGGAGAT
 8821 ACGGCCCATG AGTTGGGAGA ATGCATTCAT GCCCGCCTCG TTCCAGACGC GGCTGTAAAC CACGGCCCCC
 8891 TCGGAGTCTC TTGCGCGCAT CACCACCTGA GCGAGGTTAA GCTCCACGTG TCTGGTGAAG ACCGCATAGT
 8961 TGCATAGGCG CTGAAAAAGG TAGTTGAGTG TGGTGGCAAT GTGTTCGGCG ACGAAGAAAT ACATGATCCA
 9031 TCGTCTCAGC GGCATTTCGC TAACATCGCC CAGAGCTTCC AAGCGCTCCA TGGCCTCGTA GAAGTCCACG
 9101 GCAAAATTAA AAAACTGGGA GTTTCGCGCG GACACGGTCA ATTCCTCCTC GAGAAGACGG ATGAGTTCGG
 9171 CTATGGTGGC CCGTACTTCG CGTTCGAAGG CTCCCGGGAT CTCTTCTTCC TCTTCTATCT CTTCTTCCAC
 9241 TAACATCTCT TCTTCGTCTT CAGGCGGGGG CGGAGGGGGC ACGCGGCGAC GTCGACGGCG CACGGGCAAA
 9311 CGGTCGATGA ATCGTTCAAT GACCTCTCCG CGGCGGCGGC GCATGGTTTC AGTGACGGCG CGGCCGTTCT
 9381 CGCGCGGTCG CAGAGTAAAA ACACCGCCGC GCATCTCCTT AAAGTGGTGA CTGGGAGGTT CTCCGTTTGG
 9451 GAGGGAGAGG GCGCTGATTA TACATTTTAT TAATTGGCCC GTAGGGACTG CGCGCAGAGA TCTGATCGTG
 9521 TCAAGATCCA CGGGATCTGA AAACCTTTCG ACGAAAGCGT CTAACCAGTC ACAGTCACAA GGTAGGCTGA
 9591 GTACGGCTTC TTGTGGGCGG GGGTGGTTAT GTGTTCGGTC TGGGTCTTCT GTTTCTTCTT CATCTCGGGA
 9661 AGGTGAGACG ATGCTGCTGG TGATGAAATT AAAGTAGGCA GTTCTAAGAC GGCGGATGGT GGCGAGGAGC
 9731 ACCAGGTCTT TGGGTCCGGC TTGCTGGATA CGCAGGCGAT TGGCCATTCC CCAAGCATTA TCCTGACATC
 9801 TAGCAAGATC TTTGTAGTAG TCTTGCATGA GCCGTTCTAC GGGCACTTCT TCCTCACCCG TTCTGCCATG
 9871 CATACGTGTG AGTCCAAATC CGCGCATTGG TTGTACCAGT GCCAAGTCAG CTACGACTCT TTCGGCGAGG
 9941 ATGGCTTGCT GTACTTGGGT AAGGGTGGCT TGAAAGTCAT CAAAATCCAC AAAGCGGTGG TAAGCCCCTG
10011 TATTAATGGT GTAAGCACAG TTGGCCATGA CTGACCAGTT AACTGTCTGG TGACCAGGGC GCACGAGCTC
10081 GGTGTATTTA AGGCGCGAAT AGGCGCGGGT GTCAAAGATG TAATCGTTGC AGGTGCGCAC CAGATACTGG
10151 TACCCTATAA GAAAATGCGG CGGTGGTTGG CGGTAGAGAG GCCATCGTTC TGTAGCTGGA GCGCCAGGGG
10221 CGAGGTCTTC CAACATAAGG CGGTGATAGC CGTAGATGTA CCTGGACATC CAGGTGATTC CTGCGGCGGT
10291 AGTAGAAGCC CGAGGAAACT CGCGTACGCG GTTCCAAATG TTGCGTAGCG GCATGAAGTA GTTCATTGTA
10361 GGCACGGTTT GACCAGTGAG GCGCGCGCAG TCATTGATGC TCTATAGACA CGGAGAAAAT GAAAGCGTTC
10431 AGCGACTCGA CTCCGTAGCC TGGAGGAACG TGAACGGGTT GGGTCGCGGT GTACCCCGGT TCGAGACTTG
10501 TACTCGAGCC GGCCGGAGCC GCGGCTAACG TGGTATTGGC ACTCCCGTCT CGACCCAGCC TACAAAAATC
10571 CAGGATACGG AATCGAGTCG TTTTGCTGGT TTCCGAATGG CAGGGAAGTG AGTCCTATTT TTTTTTTTTT
10641 TTTGCCGCTC AGATGCATCC CGTGCTGCGA CAGATGCGCC CCCAACAACA GCCCCCCTCG CAGCAGCAGC
10711 AGCAGCAACC ACAAAAGGCT GTCCCTGCAA CTACTGCAAC TGCCGCCGTG AGCGGTGCGG GACAGCCCGC
10781 CTATGATCTG GACTTGGAAG AGGGCGAAGG ACTGGCACGT CTAGGTGCGC CTTCGCCCGA GCGGCATCCG
10851 CGAGTTCAAC TGAAAAAGA TTCTCGCGAG GCGTATGTGC CCCAACAGAA CCTATTTAGA GACAGAAGCG
10921 GCGAGGAGCC GGAGGAGATG CGAGCTTCCC GCTTTAACGC GGGTCGTGAG CTGCGTCACG GTTTGGACCG
10991 AAGACGAGTG TTGCGAGACG AGGATTTCGA AGTTGATGAA GTGACAGGGA TCAGTCCTGC CAGGGCACAC
11061 GTGGCTGCAG CCAACCTTGT ATCGGCTTAC GAGCAGACAG TAAAGGAAGA GCGTAACTTC CAAAAGTCTT
11131 TTAATAATCA TGTGCGAACC CTGATTGCCC GCGAAGAAGT TACCCTTGGT TTGATGCATT TGTGGGATTT
11201 GATGGAAGCT ATCATTCAGA ACCCTACTAG CAAACCTCTG ACCGCCCAGC TGTTTCTGGT GGTGCAACAC
11271 AGCAGAGACA ATGAGGCTTT CAGAGAGGCG CTGCTGAACA TCACCGAACC CGAGGGGAGA TGGTTGTATG
11341 ATCTTATCAA CATTCTACAG AGTATCATAG TGCAGGAGCG GAGCCTGGGC CTGGCCGAGA AGGTAGCTGC
11411 CATCAATTAC TCGGTTTTGA GCTTGGGAAA ATATTACGCT CGCAAAATCT ACAAGACTCC ATACGTTCCC
11481 ATAGACAAGG AGGTGAAGAT AGATGGGTTC TACATGCGCA TGACGCTCAA GGTCTTGACC CTGAGCGATG
11551 ATCTTGGGGT GTATCGCAAT GACAGAATGC ATCGCGCGGT TAGCGCCAGC AGGAGGCGCG AGTTAAGCGA
11621 CAGGGAACTG ATGCACAGTT TGCAAAGAGC TCTGACTGGA GCTGGAACCG AGGGTGAGAA TTACTTCGAC
11691 ATGGGAGCTG ACTTGCAGTG GCAGCCTAGT CGCAGGGCTC TGAGCGCCGC GACGGCAGGA TGTGAGCTTC
11761 CTTACATAGA AGAGGCGGAT GAAGGCGAGG AGGAAGAGGG CGAGTACTTG GAAGACTGAT GGCACAACCC
```

Figure 5D

```
11831 GTGTTTTTTG CTAGATGGAA CAGCAAGCAC CGGATCCCGC AATGCGGGCG GCGCTGCAGA GCCAGCCGTC
11901 CGGCATTAAC TCCTCGGACG ATTGGACCCA GGCCATGCAA CGTATCATGG CGTTGACGAC TCGCAACCCC
11971 GAAGCCTTTA GACAGCAACC CCAGGCCAAC CGTCTATCGG CCATCATGGA AGCTGTAGTG CCTTCCCGAT
12041 CTAATCCCAC TCATGAGAAG GTCCTGGCCA TCGTGAACGC GTTGGTGGAG AACAAAGCTA TTCGTCCAGA
12111 TGAGGCCGGA CTGGTATACA ACGCTCTCTT AGAACGCGTG GCTCGCTACA ACAGTAGCAA TGTGCAAACC
12181 AATTTGGACC GTATGATAAC AGATGTACGC GAAGCCGTGT CTCAGCGCGA AAGGTTCCAG CGTGATGCCA
12251 ACCTGGGTTC GCTGGTGGCG TTAAATGCTT TCTTGAGTAC TCAGCCTGCT AATGTGCCGC GTGGTCAACA
12321 GGATTATACT AACTTTTTAA GTGCTTTGAG ACTGATGGTA TCAGAAGTAC CTCAGAGCGA AGTGTATCAG
12391 TCCGGTCCTG ATTACTTCTT TCAGACTAGC AGACAGGGCT TGCAGACGGT AAATCTGAGC CAAGCTTTTA
12461 AAAACCTTAA AGGTTTGTGG GGAGTGCATG CCCCGGTAGG AGAAAGAGCA ACCGTGTCTA GCTTGTTAAC
12531 TCCGAACTCC CGCCTGTTAT TACTGTTGGT AGCTCCTTTC ACCGACAGCG GTAGCATCGA CCGTAATTCC
12601 TATTTGGGTT ACCTACTAAA CCTGTATCGC GAAGCCATAG GGCAAAGTCA GGTGGACGAG CAGACCTATC
12671 AAGAAATTAC CCAAGTCAGT CGCGCTTTGG GACAGGAAGA CACTGGCAGT TTGGAAGCA CTCTGAACTT
12741 CTTGCTTACC AATCGGTCTC AAAAGATCCC TCCTCAATAT GCTCTTACTG CGGAGGAGGA GAGGATCCTT
12811 AGATATGTGC AGCAGAGCGT GGGATTGTTT CTGATGCAAG AGGGGGCAAC TCCGACTGCA GCACTGGACA
12881 TGACAGCGCG AAATATGGAG CCCAGCATGT ATGCCAGTAA CCGACCTTTC ATTAACAAAC TGCTGGACTA
12951 CTTGCACAGA GCTGCCGCTA TGAACTCTGA TTATTTCACC AATGCCATCT TAAACCCGCA CTGGCTGCCC
13021 CCACCTGGTT TCTACACGGG CGAATATGAC ATGCCCGACC CTAATGACGG ATTTCTGTGG GACGACGTGG
13091 ACAGCGATGT TTTTTCACCT CTTTCTGATC ATCGCACGTG GAAAAAGGAA GGCGGTGATA GAATGCATTC
13161 TTCTGCATCG CTGTCCGGGG TCATGGGTGC TACCGCGGCT GAGCCCGAGT CTGCAAGTCC TTTTCCTAGT
13231 CTACCCTTTT CTCTACACAG TGTACGTAGC AGCGAAGTGG GTAGAATAAG TCGCCCGAGT TTAATGGGCG
13301 AAGAGGAGTA CCTAAACGAT TCCTTGCTCA GACCGGCAAG AGAAAAAAAT TTCCCAAACA ATGGAATAGA
13371 AAGTTTGGTG GATAAAATGA GTAGATGGAA GACTTATGCT CAGGATCACA GAGACGAGCC TGGGATCATG
13441 GGGACTACAA GTAGAGCGAG CCGTAGACGC CAGCGCCATG ACAGACAGAG GGGTCTTGTG TGGGACGATG
13511 AGGATTCGGC CGATGATAGC AGCGTGTTGG ACTTGGGTGG GAGAGGAAGG GGCAACCCGT TTGCTCATTT
13581 GCGCCCTCGC TTGGGTGGTA TGTTGTGAAA AAAAATAAAA AAGAAAAACT CACCAAGGCC ATGGCGACGA
13651 GCGTACGTTC GTTCTTCTTT ATTATCTGTG TCTAGTATAA TGAGGCGAGT CGTGCTAGGC GGAGCGGTGG
13721 TGTATCCGGA GGGTCCTCCT CCTTCGTACG AGAGCGTGAT GCAGCAGCAG CAGGCGACGG CGGTGATGCA
13791 ATCCCCACTG GAGGGTCCCT TTGTGCCTCC GCGATACCTG GCACCTACGG AGGGCAGAAA CAGCATTCGT
13861 TACTCGGAAC TGGCACCTCA GTACGATACC ACCAGGTTGT ATCTGGTGGA CAACAAGTCG GCGGACATTG
13931 CTTCTCTGAA CTATCAGAAT GACCACAGCA ACTTCTTGAC CACGGTGGTG CAGAACAATG ACTTTACCCC
14001 TACGGAAGCC AGCACCCAGA CCATTAACTT TGATGAACGA TCGCGGTGGG GCGGTCAGCT AAAGACCATC
14071 ATGCATACTA ACATGCCAAA CGTGAACGAG TATATGTTTA GTAACAAGTT CAAAGCGCGT GTGATGGTGT
14141 CCAGAAAACC TCCCGACGGT GCTGCAGTTG GGGATACTTA TGATCACAAG CAGGATATTT TGGAATATGA
14211 GTGGTTCGAG TTTACTTTGC CAGAAGGCAA CTTTTCAGTT ACTATGACTA TTGATTTGAT GAACAATGCC
14281 ATCATAGATA ATTACTTGAA AGTGGGTAGA CAGAATGGAG TGCTTGAAAG TGACATTGGT GTTAAGTTCG
14351 ACACCAGGAA CTTCAAGCTG GGATGGGATC CCGAAACCAA GTTGATCATG CCTGGAGTGT ATACGTATGA
14421 AGCTTCCAT CCTGACATTG TCTTACTGCC TGGCTGCGGA GTGGATTTTA CCGAGAGTCG TTTGAGCAAC
14491 CTTCTTGGTA TCAGAAAAAA ACAGCCATTT CAAGAGGGTT TTAAGATTTT GTATGAAGAT TTAGAAGGTG
14561 GTAATATTCC GGCCCTCTTG GATGTAGATG CCTATGAGAA CAGTAAGAAA GAACAAAAAG CCAAAATAGA
14631 AGCTGCTACA GCTGCTGCAG AAGCTAAGGC AAACATAGTT GCCAGCGACT CTACAAGGGT TGCTAACGCT
14701 GGAGAGGTCA GAGGAGACAA TTTTGCGCCA ACACCTGTTC CGACTGCAGA ATCATTATTG GCCGATGTGT
14771 CTGAAGGAAC GGACGTGAAA CTCACTATTG AACCTGTAGA AAAAGATAGT AAGAATAGAA GCTATAATGT
14841 GTTGGAAGAC AAAATCAACA CAGCCTATCG CAGTTGGTAT CTTTCGTACA ATTATGGCGA TCCCGAAAAA
14911 GGAGTGCGTT CCTGGACATT GCTCACCACC TCAGATGTCA CCTGCGGAGC AGAGCAGGTT TACTGGTCGC
14981 TTCCAGACAT GATGAAGGAT CCTGTCACTT TCCGCTCCAC TAGACAAGTC AGTAACTACC CTGTGGTGGG
15051 TGCAGAGCTT ATGCCCGTCT TCTCAAAGAG CTTCTACAAC GAACAAGCTG TGTACTCCCA GCAGCTCCGC
15121 CAGTCCACCT CGCTTACGCA CGTCTTCAAC CGCTTTCCTG AGAACCAGAT TTTAATCGT CCGCCGGCGC
15191 CCACCATTAC CACCGTCAGT GAAAACGTTC CTGCTCTCAC AGATCACGGG ACCCTGCCGT TGCGCAGCAG
15261 TATCCGGGGA GTCCAACGTG TGACCGTTAC TGACGCCAGA CGCCGCACCT GTCCCTACGT GTACAAGGCA
15331 CTGGGCATAG TCGCACCGCG CGTCCTTTCA AGCCGCACTT TCTAAAAAAA AAAAATGTCC ATTCTTATCT
15401 CGCCCAGTAA TAACACCGGT TGGGGTCTGC GCGCTCCAAG CAAGATGTAC GGAGGCGCAC GCAAACGTTC
15471 TACCCAACAT CCCGTCGTG TTCGCGGACA TTTTCGCGCT CCATGGGGTG CCCTCAAGGG CCGCACTCGC
15541 GTTCGAACCA CCGTCGATGA TGTAATCGAT CAGGTGGTTG CCGACGCCCG TAATTATACT CCTACTGCGC
15611 CTACATCTAC TGTGGATGCA GTTATTGACA GTGTAGTGGC TGACGCTCGC AACTATGCTC GACGTAAGAG
15681 CCGGCGAAGG CGCATTGCCA GACGCCACCG AGCTACCACT GCCATGCGAG CCGCAAGAGC TCTGCTACGA
15751 AGAGCTAGAC GCGTGGGGCG AAGAGCCATG CTTAGGGCGG CCAGACGTGC AGCTTCGGGC GCCAGCGCCG
```

Figure 5E

```
15821  GCAGGTCCCG CAGGCAAGCA GCCGCTGTCG CAGCGGCGAC TATTGCCGAC ATGGCCCAAT CGCGAAGAGG
15891  CAATGTATAC TGGGTGCGTG ACGCTGCCAC CGGTCAACGT GTACCCGTGC GCACCCGTCC CCCTCGCACT
15961  TAGAAGATAC TGAGCAGTCT CCGATGTTGT GTCCCAGCGG CGAGGATGTC CAAGCGCAAA TACAAGGAAG
16031  AAATGCTGCA GGTTATCGCA CCTGAAGTCT ACGGCCAACC GTTGAAGGAT GAAAAAAAAC CCCGCAAAAT
16101  CAAGCGGGTT AAAAAGGACA AAAAAGAAGA GGAAGATGGC GATGATGGGC TGGCGGAGTT TGTGCGCGAG
16171  TTTGCCCCAC GGCGACGCGT GCAATGGCGT GGGCGCAAAG TTCGACATGT GTTGAGACCT GGAACTTCGG
16241  TGGTCTTTAC ACCCGGCGAG CGTTCAAGCG CTACTTTTAA GCGTTCCTAT GATGAGGTGT ACGGGGATGA
16311  TGATATTCTT GAGCAGGCGG CTGACCGATT AGGCGAGTTT GCTTATGGCA AGCGTAGTAG AATAACTTCC
16381  AAGGATGAGA CAGTGTCAAT ACCCTTGGAT CATGGAAATC CCACCCCTAG TCTTAAACCG GTCACTTTGC
16451  AGCAAGTGTT ACCCGTAACT CCGCGAACAG GTGTTAAACG CGAAGGTGAA GATTTGTATC CCACTATGCA
16521  ACTGATGGTA CCCAAACGCC AGAAGTTGGA GGACGTTTTG GAGAAAGTAA AAGTGGATCC AGATATTCAA
16591  CCTGAGGTTA AAGTGAGACC CATTAAGCAG GTAGCGCCTG GTCTGGGGGT ACAAACTGTA GACATTAAGA
16661  TTCCCACTGA AAGTATGGAA GTGCAAACTG AACCCGCAAA GCCTACTGCC ACCTCCACTG AAGTGCAAAC
16731  GGATCCATGG ATGCCCATGC CTATTACAAC TGACGCCGCC GGTCCCACTC GAAGATCCCG ACGAAAGTAC
16801  GGTCCAGCAA GTCTGTTGAT GCCCAATTAT GTTGTACACC CATCTATTAT TCCTACTCCT GGTTACCGAG
16871  GCACTCGCTA CTATCGCAGC CGAAACAGTA CCTCCCGCCG TCGCCGCAAG ACACCTGCAA ATCGCAGTCG
16941  TCGCCGTAGA CGCACAAGCA AACCGACTCC CGGCGCCCTG GTGCGGCCAG GTGTACCGCAA TGGTAGTGCG
17011  GAACCTTTGA CACTGCCGCG TGCGCGTTAC CATCCGAGTA TCATCACTTA ATCAATGTTG CCGCTGCCTC
17081  CTTGCAGATA TGGCCCTCAC TTGTCGCCTT CGCGTTCCCA TCACTGGTTA CCGAGGAAGA AACTCGCGCC
17151  GTAGAAGAGG GATGTTGGGA CGCGGAATGC GACGCTACAG GCGACGGCGT GCTATCCGCA AGCAATTGCG
17221  GGGTGGTTTT TTACCAGCCT TAATTCCAAT TATCGCTGCT GCAATTGGCG CGATACCAGG CATAGCTTCC
17291  GTGGCGGTTC AGGCCTCGCA ACGACATTGA CATTGGAAAA AAAACGTATA AATAAAAAAA AATACAATGG
17361  ACTCTGACAC TCCTGGTCCT GTGACTATGT TTTCTTAGAG ATGGAAGACA TCAATTTTTC ATCCTTGGCT
17431  CCGCGACACG GCACGAAGCC GTACATGGGC ACCTGGAGCG ACATCCGCAC GAGCCAACTG AACGGGGGCG
17501  CCTTCAATTG GAGCAGTATC TGGGACGGGC TTAAAAATTT TGGCTCAACC ATAAAAACAT ACGGGAACAA
17571  AGCTTGGAAC AGCAGTACAG GACAGGCGCT TAGAAATAAA CTTAAAGACC AGAACTTCCA ACAAAAAGTA
17641  GTCGATGGGA TAGCTTCCGG CATCAATGGA GTGGTAGATT TGGCTAACCA GGCTGTGCAG AAAAAGATAA
17711  ACAGTCGTTT GGACCCGCCG CCAGCAACCC CAGGTGAAAT GCAAGTGGAG GAAGAAATTC CTCCGCCAGA
17781  AAAACGAGGC GACAAGCGTC CGCGTCCCGA TTTGGAAGAG ACGCTGGTGA CGCGCGTAGA TGAACCGCCT
17851  TCTTATGAGG AAGCAACGAA GCTTGGAATG CCCACCACTA GACCGATAGC CCCAATGGCC ACCGGGGTGA
17921  TGAAACCTTC TCAGTTGCAT CGACCCGTCA CCTTGGATTT GCCCCCTCCC CCTGCTGCTA CTGCTGTACC
17991  CGCTTCTAAG CCTGTCGCTG CCCCGAAACC AGTCGCCGTA GCCAGGTCAC GTCCCGGGGG CGCTCCTCGT
18061  CCAAATGCGC ACTGGCAAAA TACTCTGAAC AGCATCGTGG GTCTAGGCGT GCAAAGTGTA AAACGCCGTC
18131  GCTGCTTTTA ATTAAATATG GAGTAGCGCT TAACTTGCCT ATCTGTGTAT ATGTGTCATT ACACGCCGTC
18201  ACAGCAGCAG AGGAAAAAAG GAAGAGGTCG TGCGTCGACG CTGAGTTACT TTCAAGATGG CCACCCCATC
18271  GATGCTGCCC CAATGGGCAT ACATGCACAT CGCCGGACAG GATGCTTCGG AGTACCTGAG TCCGGGTCTG
18341  GTGCAGTTCG CCCGCGCCAC AGACACCTAC TTCAATCTGG GAAATAAGTT TAGAAATCCC ACCGTAGCGC
18411  CGACCCACGA TGTGACCACC GACCGTAGCC AGCGGCTCAT GTTGCGCTTC GTGCCCGTTG ACCGGGAGGA
18481  CAATACATAC TCTTACAAAG TGCGGTACAC CCTGGCCGTG GGCGACAACA GAGTGCTGGA TATGGCCAGC
18551  ACGTTCTTTG ACATTAGGGG CGTGTTGACA AGAGGTCCCA GTTTCAAACC CTATTCTGGT ACGGCTTACA
18621  ACTCTCTGGC TCCTAAAGGC GCTCCAAATG CATCTCAATG GATTGCAAAA GGCGTACCAA CTGCAGCAGC
18691  CGCAGGCAAT GGTGAAGAAG AACATGAAAC AGAGGAGAAA ACTGCTACTT ACACTTTTGC CAATGCTCCT
18761  GTAAAAGCCG AGGCTCAAAT TACAAAAGAG GGCTTACCAA TAGGTTTGGA GATTTCAGCT GAAAACGAAT
18831  CTAAACCCAT CTATGCAGAT AAACTTTATC AGCCAGAACC TCAAGTGGGA GATGAAACTT GGACTGACCT
18901  AGACGGAAAA ACCGAAGAGT ATGGAGGCAG GGCTCTAAAG CCTACTACTA ACATGAAACC CTGTTACGGG
18971  TCCTATGCGA AGCCTACTAA TTTAAAAGGT GGTCAGGCAA AACCGAAAAA CTCGGAACCG TCGAGTGAAA
19041  AAATTGAATA TGATATTGAC ATGGAATTTT TTGATAACTC ATCGCAAAGA ACAAACTTCA GTCCTAAAAT
19111  TGTCATGTAT GCAGAAAATG TAGGTTTGGA AACGCCAGAC ACTCATGTAG TGTACAAACC TGGAACAGAA
19181  GACACAAGTT CCGAAGCTAA TTTGGGACAA CAGTCTATGC CCAACAGACC CAACTACATT GGCTTCAGAG
19251  ATAACTTTAT TGGACTCATG TACTATAACA GTACTGGTAA CATGGGGGTG CTGGCTGGTC AAGCGTCTCA
19321  GTTAAATGCA GTGGTTGACT TGCAGGACAG AAACACAGAA CTTTCTTACC AACTCTTGCT TGACTCTCTG
19391  GGCGACAGAA CCAGATACTT TAGCATGTGG AATCAGGCTG TGGACAGTTA TGATCCTGAT GTACGTGTTA
19461  TTGAAAATCA TGGTGTGGAA GATGAACTTC CCAACTATTG TTTTCCACTG GACGGCATAG GTGTTCCAAC
19531  AACCAGTTAC AAATCAATAG TTCCAAATGG AGAAGATAAT AATAATTGGA AAGAACCTGA AGTAAATGGA
19601  ACAAGTGAGA TCGGACAGGG TAATTTGTTT GCCATGGAAA TTAACCTTCA AGCCAATCTA TGGCGAAGTT
19671  TCCTTTATTC CAATGTGGCT CTGTATCTCC CAGACTCGTA CAAATACACC CCGTCCAATG TCACTCTTCC
19741  AGAAAACAAA AACACCTACG ACTACATGAA CGGGCGGGTG GTGCCGCCAT CTCTAGTAGA CACCTATGTG
```

Figure 5F

```
19811 AACATTGGTG CCAGGTGGTC TCTGGATGCC ATGGACAATG TCAACCCATT CAACCACCAC CGTAACGCTG
19881 GCTTGCGTTA CCGATCTATG CTTCTGGGTA ACGGACGTTA TGTGCCTTTC CACATACAAG TGCCTCAAAA
19951 ATTCTTCGCT GTTAAAAACC TGCTGCTTCT CCCAGGCTCC TACACTTATG AGTGGAACTT TAGGAAGGAT
20021 GTGAACATGG TTCTACAGAG TTCCCTCGGT AACGACCTGC GGGTAGATGG CGCCAGCATC AGTTTCACGA
20091 GCATCAACCT CTATGCTACT TTTTTCCCCA TGGCTCACAA CACCGCTTCC ACCCTTGAAG CCATGCTGCG
20161 GAATGACACC AATGATCAGT CATTCAACGA CTACCTATCT GCAGCTAACA TGCTCTACCC CATTCCTGCC
20231 AATGCAACCA ATATTCCCAT TTCCATTCCT TCTCGCAACT GGGCGGCTTT CAGAGGCTGG TCATTTACCA
20301 GACTGAAAAC CAAAGAAACT CCCTCTTTGG GGTCTGGATT TGACCCCTAC TTTGTCTATT CTGGTTCTAT
20371 TCCCTACCTG GATGGTACCT TCTACCTGAA CCACACTTTT AAGAAGGTTT CCATCATGTT TGACTCTTCA
20441 GTGAGCTGGC CTGGAAATGA CAGGTTACTA TCTCCTAACG AATTTGAAAT AAAGCGCACT GTGGATGGCG
20511 AAGGCTACAA CGTAGCCCAA TGCAACATGA CCAAAGACTG GTTCTTGGTA CAGATGCTCG CCAACTACAA
20581 CATCGGCTAT CAGGGCTTCT ACATTCCAGA AGGATACAAA GATCGCATGT ATTCATTTTT CAGAAACTTC
20651 CAGCCCATGA GCAGGCAGGT GGTTGATGAG GTCAATTACA AAGACTTCAA GGCCGTCGCC ATACCCTACC
20721 AACACAACAA CTCTGGCTTT GTGGGTTACA TGGCTCCGAC CATGCGCCAA GGTCAACCCT ATCCCGCTAA
20791 CTATCCCTAT CCACTCATTG GAACAACTGC CGTAAATAGT GTTACGCAGA AAAAGTTCTT GTGTGACAGA
20861 ACCATGTGGC GCATACCGTT CTCGAGCAAC TTCATGTCTA TGGGGGCCCT TACAGACTTG GGACAGAATA
20931 TGCTCTATGC CAACTCAGCT CATGCTCTGG ACATGACCTT TGAGGTGGAT CCCATGGATG AGCCCACCCT
21001 GCTTTATCTT CTCTTCGAAG TTTTCGACGT GGTCAGAGTG CATCAGCCAC ACCGCGGCAT CATCGAGGCA
21071 GTCTACCTGC GTACACCGTT CTCGGCCGGT AACGCTACCA CGTAAGAAGC TTCTTGCTTC TTGCAAATAG
21141 CAGCTGCAAC CATGGCCTGC GGATCCCAAA ACGGCTCCAG CGAGCAAGAG CTCAGAGCCA TTGTCCAAGA
21211 CCTGGGTTGC GGACCCTATT TTTTGGGAAC CTACGATAAG CGCTTCCCGG GGTTCATGGC CCCCGATAAG
21281 CTCGCCTGTG CCATTGTAAA TACGGCCGGA CGTGAGACGG GGGGAGAGCA CTGGTTGGCT TTCGGTTGGA
21351 ACCCACGTTC TAACACCTGC TACCTTTTTG ATCCTTTTGG ATTCTCGGAT GATCGTCTCA AACAGATTTA
21421 CCAGTTTGAA TATGAGGGTC TCCTGCGCCG CAGCGCTCTT GCTACCAAGG ACCGCTGTAT TACGCTGGAA
21491 AAATCTACCC AGACCGTGCA GGGCCCCCGT TCTGCCGCCT GCGGACTTTT CTGCTGCATG TTCCTTCACG
21561 CCTTTGTGCA CTGGCCTGAC CGTCCCATGG ACGGAAACCC CACCATGAAA TTGCTAACTG GAGTGCCAAA
21631 CAACATGCTT CATTCCTTCA AAGTCCAGCC CACCCTGTGT GACAATCAAA AAGCACTCTA CCATTTTCTT
21701 AATACCCATT CGCCTTATTT TCGCTCTCAT CGTACACACA TCGAAAGGGC CACTGCGTTC GACCGTATGG
21771 ATGTTCAATA ATGACTCATG TAAACAACGT GTTCAATAAA CATCACTTTA TTTTTTTACA TGTATCAAGG
21841 CTCTGGATTA CTTATTTATT TACAAGTCGA ATGGGTTCTG ACGAGAATCA GAATGACCCG CAGGCAGTGA
21911 TACGTTGCGG AACTGATACT TGGGTTGCCA CTTGAATTCG GAATCACCA ACTTGGGAAC CGGTATATCG
21981 GGCAGGATGT CACTCCACAG CTTTCTGGTC AGCTGCAAAG CTCCAAGCAG GTCAGGAGCC GAAATCTTGA
22051 AATCACAATT AGGACCAGTG CTCTGAGCGC GAGAGTTGCG GTACACCGGA TTGCAGCACT GAAACACCAT
22121 CAGCGACGGA TGTCTCACGC TTGCCAGCAC GGTGGGATCT GCAATCATGC CCACATCCAG ATCTTCAGCA
22191 TTGGCAATGC TGAACGGGGT CATCTTGCAG GTCTGCCTAC CCATGGCGGG CACCCAATTA GGCTTGTGGT
22261 TGCAATCGCA GTGCAGGGGG ATCAGTATCA TCTTGGCCTG ATCCTGTCTG ATTCCTGGAT ACACGGCTCT
22331 CATGAAAGCA TCATATTGCT TGAAAGCCTG CTGGGCTTTA CTACCCTCGG TATAAAACAT CCCGCAGGAC
22401 CTGCTCGAAA ACTGGTTAGC TGCACAGCCG GCATCATTCA CACAGCAGCG GGCGTCATTG TTGGCTATTT
22471 GCACCACACT TCTGCCCCAG CGGTTTTGGG TGATTTTGGT TCGCTCGGGA TTCTCCTTTA AGGCTCGTTG
22541 TCCGTTCTCG CTGGCCACAT CCATCTCGAT AATCTGCTCC TTCTGAATCA TAATATTGCC ATGCAGGCAC
22611 TTCAGCTTGC CCTCATAATC ATTGCAGCCA TGAGGCCACA ACGCACAGCC TGTACATTCC CAATTATGGT
22681 GGGCGATCTG AGAAAAAGAA TGTATCATTC CCTGCAGAAA TCTTCCCATC ATCGTGCTCA GTGTCTTGTG
22751 ACTAGTGAAA GTTAACTGGA TGCCTCGGTG CTCTTCGTTT ACGTACTGGT GACAGATGCG CTTGTATTGT
22821 TCGTGTTGCT CAGGCATTAG TTTTAAAACAG GTTCTAAGTT CGTTATCCAG CCTGTACTTC TCCATCAGCA
22891 GACACATCAC TTCCATGCCT TTCTCCCAAG CAGACACCAG GGGCAAGCTA ATCGGATTCT TAACAGTGCA
22961 GGCAGCAGCT CCTTTAGCCA GAGGGTCATC TTTAGCGATC TTCTCAATGC TTCTTTTGCC ATCCTTCTCA
23031 ACGATGCGCA CGGGCGGGTA GCTGAAACCC ACTGCTACAA GTTGCGCCTC TTCTCTTTCT TCTTCGCTGT
23101 CTTGACTGAT GTCTTGCATG GGGATATGTT TGGTCTTCCT TGGCTTCTTT TTGGGGGTA TCGGAGGAGG
23171 AGGACTGTCG CTCCGTTCCG GAGACAGGGA GGATTGTGAC GTTTCGCTCA CCATTACCAA CTGACTGTCG
23241 GTAGAAGAAC CTGACCCCAC ACGGCGACAG GTGTTTTTCT TCGGGGGCAG AGGTGGAGGC GATTGCGAAG
23311 GGCTGCGGTC CGACCTGGAA GGCGGATGAC TGGCAGAACC CCTTCCGCGT TCGGGGGTGT GCTCCCTGTG
23381 GCGGTCGCTT AACTGATTTC CTTCGCGGCT GGCCATTGTG TTCTCCTAGG CAGAGAAACA ACAGACATGG
23451 AAACTCAGCC ATTGCTGTCA ACATCGCCAC GAGTGCCATC ACATCTCGTC CTCAGCGACG AGGAAAAGGA
23521 GCAGAGCTTA AGCATTCCAC CGCCCAGTCC TGCCACCACC TCTACCCTAG AAGATAAGGA GGTCGACGCA
23591 TCTCATGACA TGCAGAATAA AAAAGCGAAA GAGTCTGAGA CAGACATCGA GCAAGACCCG GGCTATGTGA
23661 CACCGGTGGA ACACGAGGAA GAGTTGAAAC GCTTTCTAGA GAGAGAGGAT GAAAACTGCC CAAAACAGCG
23731 AGCAGATAAC TATCACCAAG ATGCTGGAAA TAGGGATCAG AACACCGACT ACCTCATAGG GCTTGACGGG
```

Figure 5G

```
23801 GAAGACGCGC TCCTTAAACA TCTAGCAAGA CAGTCGCTCA TAGTCAAGGA TGCATTATTG GACAGAACTG
23871 AAGTGCCCAT CAGTGTGGAA GAGCTCAGCT GCGCCTACGA GCTTAACCTT TTTTCACCTC GTACTCCCCC
23941 CAAACGTCAG CCAAACGGCA CCTGCGAGCC AAATCCTCGC TTAAACTTTT ATCCAGCTTT TGCTGTGCCA
24011 GAAGTACTGG CTACCTATCA CATCTTTTTT AAAAATCAAA AAATTCCAGT CTCCTGCCGC GCTAATCGCA
24081 CCCGCGCCGA TGCCCTACTC AATCTGGGAC CTGGTTCACG CTTACCTGAT ATAGCTTCCT TGGAAGAGGT
24151 TCCAAAGATC TTCGAGGGTC TGGGCAATAA TGAGACTCGG GCCGCAAATG CTCTGCAAAA GGGAGAAAAT
24221 GGCATGGATG AGCATCACAG CGTTCTGGTG GAATTGGAAG GCGATAATGC CAGACTCGCA GTACTCAAGC
24291 GAAGCGTCGA GGTCACACAC TTCGCATATC CCGCTGTCAA CCTGCCCCCT AAAGTCATGA CGGCGGTCAT
24361 GGACCAGTTA CTCATTAAGC GCGCAAGTCC CCTTTCAGAA GACATGCATG ACCCAGATGC CTGTGATGAG
24431 GGTAAACCAG TGGTCAGTGA TGAGCAGCTA ACCCGATGGC TGGGCACCGA CTCTCCCCGG GATTTGGAAG
24501 AGCGTCGCAA GCTTATGATG GCCGTGGTGC TGGTTACCGT AGAACTAGAG TGTCTCCGAC GTTTCTTTAC
24571 CGATTCAGAA ACCTTGCGCA AACTCGAAGA GAATCTGCAC TACACTTTTA GACACGGCTT TGTGCGGCAG
24641 GCATGCAAGA TATCTAACGT GGAACTCACC AACCTGGTTT CCTACATGGG TATTCTGCAT GAGAATCGCC
24711 TAGGACAAAG CGTGCTGCAC AGCACCCTTA AGGGGAAGC CCGCCGTGAT TACATCCGCG ATTGTGTCTA
24781 TCTCTACCTG TGCCACACGT GGCAAACCGG CATGGGTGTA TGGCAGCAAT GTTTAGAAGA ACAGAACTTG
24851 AAAGAGCTTG ACAAGCTCTT ACAGAAATCT CTTAAGGTTC TGTGGACAGG GTTCGACGAG CGCACCGTCG
24921 CTTCCGACCT GGCAGACCTC ATCTTCCCAG AGCGTCTCAG GGTTACTTTG CGAAACGGAT TGCCTGACTT
24991 TATGAGCCAG AGCATGCTTA ACAATTTTCG CTCTTTCATC CTGGAACGCT CGGTATCCT GCCCGCCACC
25061 TGCTGCGCAC TGCCCTCCGA CTTTGTGCCT CTCACCTACC GCGAGTGCCC CCCGCCGCTA TGGAGTCACT
25131 GCTACCTGTT CCGTCTGGCC AACTATCTCT CCTACCACTC GGATGTGATC GAGGATGTGA GCGGAGACGG
25201 CTTGCTGGAG TGCCACTGCC GCTGCAATCT GTGCACGCCC CACCGGTCCC TAGCTTGCAA CCCCCAGTTG
25271 ATGAGCGAAA CCCAGATAAT AGGCACCTTT GAATTGCAAG GCCCCAGCAG CCAAGGCGAT GGGTCTTCTC
25341 CTGGGCAAAG TTTAAAACTG ACCCCGGGAC TGTGGACCTC CGCCTACTTG CGCAAGTTTG CTCCGGAAGA
25411 TTACCACCCC TATGAAATCA AGTTCTATGA GGACCAATCA CAGCCTCCAA AGGCCGAACT TTCGGCTTGC
25481 GTCATCACCC AGGGGGCAAT TCTGCCCAA TTGCAAGCCA TCCAAAAATC CCGCCAAGAA TTTCTACTGA
25551 AAAAGGGTAA GGGGGTCTAC CTTGACCCCC AGACCGGCGA GGAACTCAAC ACAAGGTTCC CTCAGGATGT
25621 CCCAACGACG AGAAAACAAG AAGTTGAAGG TGCAGCGCC GCCCCCAGAA GATATGGAGG AAGATTGGGA
25691 CAGTCAGGCA GAGGAGGCGG AGGAGGACAG TCTGGAGGAC AGTCTGGAGG AAGACAGTTT GGAGGAGGAA
25761 AACGAGGAGG CAGAGGAGGT GGAAGAAGTA ACCGCCGACA AACAGTTATC CTCGGCTGCG GAGACAAGCA
25831 ACAGCGCTAC CATCTCCGCT CCGAGTCGAG GAACCCGGCG GCGTCCCAGC AGTAGATGGG ACGAGACCGG
25901 ACGCTTCCCG AACCCAACCA GCGCTTCCAA GACCGGTAAG AAGGATCGGC AGGGATACAA GTCCTGGCGG
25971 GGGCATAAGA ATGCCATCAT CTCCTGCTTG CATGAGTGCG GGGCAACAT ATCCTTCACG CGGCGCTACT
26041 TGCTATTCCA CCATGGGGTG AACTTTCCGC GCAATGTTTT GCATTACTAC CGTCACCTCC ACAGCCCCTA
26111 CTATAGCCAG CAAATCCCGA CAGTCTCGAC AGATAAAGAC AGCGGCGGCG ACCTCCAACA GAAAACCAGC
26181 AGCGGCAGTT AGAAAATACA CAACAAGTGC AGCAACAGGA GGATTAAAGA TTACAGCCAA CGAGCCAGCG
26251 CAAACCCGAG AGTTAAGAAA TCGGATCTTT CCAACCCTGT ATGCCATCTT CCAGCAGAGT CGGGGTCAAG
26321 AGCAGGAACT GAAAATAAAA AACCGATCTC TGCGTTCGCT CACCAGAAGT TGTTTGTATC ACAAGAGCGA
26391 AGATCAACTT CAGCGCACTC TCGAGGACGC CGAGGCTCTC TTCAACAAGT ACTGCGCGCT GACTCTTAAA
26461 GAGTAGGCAG CGACCGCGCT TATTCAAAAA AGGCGGGAAT TACATCATCC TCGACATGAG TAAAGAAATT
26531 CCCACGCCTT ACATGTGGAG TTATCAACCC CAAATGGGAT TGGCAGCAGG CGCCTCCCAG GACTACTCCA
26601 CCCGCATGAA TTGGCTCAGC GCCGGGCCTT CTATGATTTC TCGAGTTAAT GATATACGCG CCTACCGAAA
26671 CCAAATACTT TTGGAACAGT CAGCTCTTAC CACCACGCCC CGCCAACACC TTAATCCCAG AAATTGGCCC
26741 GCCGCCCTAG TGTACCAGGA AAGTCCCGCT CCCACCACTG TATTACTTCC TCGAGACGCC CAGGCCGAAG
26811 TCCAAATGAC TAATGCAGGT GCGCAGTTAG CTGGCGGCTC CACCCTATGT CGTCACAGGC CTCGGCATAA
26881 TATAAAACGC CTGATGATCA GAGGCCGAGG TATCCAGCTC AACGACGAGT CGGTGAGCTC TCCGCTTGGT
26951 CTACGACCAG ACGGAATCTT TCAGATTGCC GGCTGCGGGA GATCTTCCTT CACCCCTCGT CAGGCTGTTC
27021 TGACTTTGGA AAGTTCGTCT TCGCAACCCC GCTCGGGCGG AATCGGGACC GTTCAATTTG TAGAGGAGTT
27091 TACTCCCTCT GTCTACTTCA ACCCCTTCTC CGGATCTCCT GGGCACTACC GGACGAGTT CATACCGAAC
27161 TTCGACGCGA TTAGCGAGTC AGTGGACGGC TACGATTGAT GTCTGGTGAC GCGGCTGAGC TATCTCGGCT
27231 GCGACATCTA GACCACTGCC GCCGCTTTCG CTGCTTTGCC CGGGAACTTA TTGAGTTCAT CTACTTCGAA
27301 CTCCCCAAGG ATCACCCTCA AGGTCCGCC CACGGAGTGC GGATTACTAT CGAAGGCAAA ATAGACTCTC
27371 GCCTGCAACG AATTTTCTCC CAGCGGCCCG TGCTGATCGA GCGAGACCAG GGAAACACCA CGGTTTCCAT
27441 CTACTGCATT TGTAATCACC CCGGATTGCA TGAAAGCCTT TGCTGTCTTA TGTGTACTGA GTTTAATAAA
27511 AACTGAATTA AGACTCTCCT ACGGACTGCC GCTTCTTCAA CCCGGATTTT ACAACCAGAA GAACAAAACT
27581 TTTCCTGTCG TCCAGGACTC TGTTAACTTC ACCTTTCCTA CTCACAAACT AGAAGCTCAA CGACTACACC
27651 GCTTTTCCAG AAGCATTTTC CCTACTAATA CTACTTTCAA AACCGGAGGT GAGCTCCACG GTCTCCCTAC
27721 AGAAAACCCT TGGGTGGAAG CGGGCCTTGT AGTACTAGGA ATTCTTGCGG GTGGGCTTGT GATTATTCTT
```

Figure 5H

```
27791 TGCTACCTAT ACACACCTTG CTTCACTTTC CTAGTGGTGT TGTGGTATTG GTTTAAAAAA TGGGGCCCAT
27861 ACTAGTCTTG CTTGTTTTAC TTTCGCTTTT GGAACCGGGT TCTGCCAATT ACGATCCATG TCTAGACTTT
27931 GACCCAGAAA ACTGCACACT TACTTTTGCA CCCGACACAA GCCGCATCTG TGGAGTTCTT ATTAAGTGCG
28001 GATGGGAATG CAGGTCCGTT GAAATTACAC ACAATAACAA AACCTGGAAC AATACCTTAT CCACCACATG
28071 GGAGCCAGGA GTTCCCGAGT GGTACACTGT CTCTGTCCGA GGTCCTGACG GTTCCATCCG CATTAGTAAC
28141 AACACTTTCA TTTTTTCTGA AATGTGCGAT CTGGCCATGT TCATGAGCAA ACAGTATTCT CTATGCCCTC
28211 CTAGCAAGGA CAACATCGTA ACGTTCTCCA TTGCTTATTG CTTGTGCGCT TGCCTTCTTA CTGCTTTACT
28281 GTGCGTATGC ATACACCTGC TTGTAACCAC TCGCATCAAA AACGCCAATA ACAAAGAAAA AATGCCTTAA
28351 CCTCTTTCTG TTTACAGACA TGGCTTCTCT TACATCTCTC ATATTTGTCA GCATTGTCAC TGCCGCTCAC
28421 GGACAAACAG TCGTCTCTAT CCCACTAGGA CATAATTACA CTCTCATAGG ACCCCCAATC ACTTCAGAGG
28491 TCATCTGGAC CAAACTGGGA AGCGTTGATT ACTTTGATAT AATCTGTAAC AAAACAAAAC CAATAATAGT
28561 AACTTGCAAC ATACAAAATC TTACATTGAT TAATGTTAGC AAAGTTTACA GCGGTTACTA TTATGGTTAT
28631 GACAGATACA GTAGTCAATA TAGAAATTAC TTGGTTCGTG TTACCCAGTT GAAAACCACG AAAATGCCAA
28701 ATATGGCAAA GATTCGATCC GATGACAATT CTCTAGAAAC TTTTACATCT CCCACCACAC CCGACGAAAA
28771 AAACATCCCA GATTCAATGA TTGCAATTGT TGCAGCGGTG GCAGTGGTGA TGGCACTAAT AATAATATGC
28841 ATGCTTTTAT ATGCTTGTCG CTACAAAAAG TTTCATCCTA AAAAACAAGA TCTCCTACTA AGGCTTAACA
28911 TTTAATTTCT TTTTATACAG CCATGGTTTC CACTACCACA TTCCTTATGC TTACTAGTCT CGCAACTCTG
28981 ACTTCTGCTC GCTCACACCT CACTGTAACT ATAGGCTCAA ACTGCACACT AAAAGGACCT CAAGGTGGTC
29051 ATGTCTTTTG GTGGAGAATA TATGACAATG GATGGTTTAC AAAACCATGT GACCAACCTG GTAGATTTTT
29121 CTGCAACGGC AGAGACCTAA CCATTATCAA CGTGACGACA AATGACAAAG GCTTCTATTA TGGAACCGAC
29191 TATAAAAGTA GTTTAGATTA TAACATTATT GTACTGCCAT CTACCACTCC AGCACCCCGC ACAACTACTT
29261 TCTCTAGCAG CAGTGTCGCT AACAATACAA TTTCCAATCC AACCTTTGCC GCGCTTTTAA AACGCACTGT
29331 GAATAATTCT ACAACTTCAC ATACAACAAT TTCCACTTCA ACAATCAGCA TCATCGCTGC AGTGACAATT
29401 GGAATATCTA TTCTTGTTTT TACCATAACC TACTACGCCT GCTGCTATAG AAAAGACAAA CATAAAGGTG
29471 ATCCATTACT TAGATTTGAT ATTTAATTTG TTCTTTTTTT TTATTTACAG TATGGTGAAC ACCAATCATG
29541 GTACCTAGAA ATTTCTTCTT CACCATACTC ATCTGTGCTT TTAATGTTTG CGCTACTTTC ACAGCAGTAG
29611 CCACAGCAAC CCCAGACTGT ATAGGAGCAT TTGCTTCCTA TGCACTTTTT GCTTTTGTTA CTTGCATCTG
29681 CGTATGTAGC ATAGTCTGCC TGGTTATTAA TTTTTTCCAA CTTCTAGACT GGATCCTTGT GCGAATTGCC
29751 TACCTGCGCC ACCATCCCGA ATACCGCAAC CAAAATATCG CGGCACTTCT TAGACTCATC TAAAACCATG
29821 CAGGCTATAC TACCAATATT TTTGCTTCTA TTGCTTCCCT ACGCTGTCTC AACCCCAGCT GCCTATAGTA
29891 CTCCACCAGA ACACCTTAGA AATGCAAAT TCCAACAACC GTGGTCATTT CTTGCTTGCT ATCGAGAAAA
29961 ATCAGAAATC CCCCCAAATT TAATAATGAT TGCTGGAATA ATTAATATAA TCTGTTGCAC CATAATTTCA
30031 TTTTTGATAT ACCCCCTATT TGATTTTGGC TGGAATGCTC CCAATGCACA TGATCATCCA CAAGACCCAG
30101 AGGAACACAT TCCCCCACAA AACATGCAAC ATCCAATAGC GCTAATAGAT TACGAAAGTG AACCACAACC
30171 CCCACTACTC CCTGCTATTA GTTACTTCAA CCTAACCGGC GGAGATGACT GAAACACTCA CCACCTCCAA
30241 TTCCGCCGAG GATCTGCTCG ATATGGACGG CCGCGTCTCA GAACAACGAC TTGCCCAACT ACGCATCCGC
30311 CAGCAGCAGG AACGCGTGGC CAAAGAGCTC AGAGATGTCA TCCAAATTCA CCAATGCAAA AAAGGCATAT
30381 TCTGTTTGGT AAAACAAGCC AAGATATCCT ACGAGATCAC CGCTACTGAC CATCGCCTCT CTTACGAACT
30451 TGGCCCCCAA CGACAAAAAT TTACCTGCAT GGTGGGAATC AACCCCATAG TTATCACCCA ACAAAGTGGA
30521 GATACTAAGG GTTGCATTCA CTGCTCCTGC GATTCCATCG AGTGCACCTA CACCCTGCTG AAGACCCTAT
30591 GCGGCCTAAG AGACCTGCTA CCAATGAATT AAAAAAAAAT GATTAATAAA AAATCACTTA CTTGAAATCA
30661 GCAATAAGGT CTCTGTTGAA ATTTTCTCCC AGCAGCACCT CACTTCCCTC TTCCCAACTC TGGTATTCTA
30731 AACCCCGTTC AGCGGCATAC TTTCTCCATA CTTTAAAGGG GATGTCAAAT TTTAGCTCCT CTCCTGTACC
30801 CACAATCTTC ATGTCTTTCT TCCCAGATGA CCAAGAGAGT CCGGCTCAGT GACTCCTTCA ACCCTGTCTA
30871 CCCCTATGAA GATGAAAGCA CCTCCCAACA CCCCTTTATA AACCCAGGGT TTATTTCCCC AAATGGCTTC
30941 ACACAAAGCC CAGACGGAGT TCTTACTTTA AATGTTTAA CCCCACTAAC AACCACAGGC GGATCTCTAC
31011 AGCTAAAAGT GGGAGGGGGA CTTACAGTGG ATGACACTGA TGGTACCTTA CAAGAAAACA TACGTGCTAC
31081 AGCACCCATT ACTAAAAATA ATCACTCTGT AGAACTATCC ATTGGAAATG GATTAGAAAC TCAAAACAAT
31151 AAACTATGTG CCAAATTGGG AAATGGGTTA AATTTAACA ACGTGACAT TTGTATAAAG GATAGTATTA
31221 ACACCTTATG GACTGGAATA AACCCTCCAC CTAACTGTCA AATGTGGAA AACACTAATA CAAATGATGG
31291 CAAACTTACT TTAGTATTAG TAAAAAATGC AGGGCTTGTT AATGGCTACG TGTCTCTAGT TGGTGTATCA
31361 GACACTGTGA ACCAAATGTT CACACAAAAG ACAGCAAACA TCCAATTAAG ATTATATTTT GACTCTTCTG
31431 GAAATCTATT AACTGAGGAA TCAGACTTAA AAATTCCACT TAAAAATAAA TCTTCTACAG CGACCAGTGA
31501 AACTGTAGCC AGCAGCAAAG CCTTTATGCC AAGTACTACA GCTTATCCCT TCAACACCAC TACTAGGGAT
31571 AGTGAAAACT ACATTCATGG AATATGTTAC TACATGACTA GTTATGATAG AAGTCTATTT CCCTTGAACA
31641 TTTCTATAAT GCTAAACAGC CGTATGATTT CTTCCAATGT TGCCTATGCC ATACAATTTG AATGGAATCT
31711 AAATGCAAGT GAATCTCCAG AAAGCAACAT AGCTACGCTG ACCACATCCC CCTTTTTCTT TTCTTACATT
```

Figure 5I

```
31781 ACAGAAGACG ACAACTAAAA TAAAGTTTAA GTGTTTTTAT TTAAAATCAC AAAATTCGAG TAGTTATTTT
31851 GCCTCCACCT TCCCATTTGA CAGAATACAC CAATCTCTCC CCACGCACAG CTTTAAACAT TTGGATACCA
31921 TTAGAGATAG ACATTGTTTT AGATTCCACA TTCCAAACAG TTTCAGAGCG AGCCAATCTG GGGTCAGTGA
31991 TAGATAAAAA TCCATCGCGA TAGTCTTTTA AAGCGCTTTC ACAGTCCAAC TGCTGCGGAT GCGACTCCGG
32061 AGTTTGGATC ACGGTCATCT GGAAGAAGAA CGATGGGAAT CATAATCCGA AAACGGTATC GGACGATTGT
32131 GTCTCATCAA ACCCACAAGC AGCCGCTGTC TGCGTCGCTC CGTGCGACTG CTGTTTATGG GATCAGGGTC
32201 CACAGTTTCC TGAAGCATGA TTTTAATAGC CCTTAACATC AACTTTCTGG TGCGATGCGC GCAGCAACGC
32271 ATTCTGATTT CACTCAAATC TTTGCAGTAG GTACAACACA TTATTACAAT ATTGTTTAAT AAACCATAAT
32341 TAAAAGCGCT CCAGCCAAAA CTCATATCTG ATATAATCGC CCCTGCATGA CCATCATACC AAAGTTTAAT
32411 ATAAATTAAA TGACGTTCCC TCAAAAACAC ACTACCCACA TACATGATCT CTTTTGGCAT GTGCATATTA
32481 ACAATCTGTC TGTACCATGG ACAACGTTGG TTAATCATGC AACCCAATAT AACCTTCCGG AACCACACTG
32551 CCAACACCGC TCCCCCAGCC ATGCATTGAA GTGAACCCTG CTGATTACAA TGACAATGAA GAACCCAATT
32621 CTCTCGACCG TGAATCACTT GAGAATGAAA AATATCTATA GTGGCACAAC ATAGACATAA ATGCATGCAT
32691 CTTCTCATAA TTTTTAACTC CTCAGGATTT AGAAACATAT CCCAGGGAAT AGGAAGCTCT TGCAGAACAG
32761 TAAAGCTGGC AGAACAAGGA AGACCACGAC CACAACTTAC ACTATGCATA GTCATAGTAT CACAATCTGG
32831 CAACAGCGGG TGGTCTTCAG TCATAGAAGC TCGGGTTTCA TTTTCCTCAC AACGTGGTAA CTGGGCTCTG
32901 GTGTAAGGGT GATGTCTGGC GCATGATGTC GAGCGTGCGC GCAACCTTGT CATAATGGAG TTGCTTCCTG
32971 ACATTCTCGT ATTTTGTATA GCAAACGCG GCCCTGGCAG AACACACTCT TCTTCGCCTT CTATCCTGCC
33041 GCTTAGCGTG TTCCGTGTGA TAGTTCAAGT ACAGCCACAC TCTTAAGTTG GTCAAAAGAA TGCTGGCTTC
33111 AGTTGTAATC AAAACTCCAT CGCATCTAAT TGTTCTGAGG AAATCATCCA CGGTAGCATA TGCAAATCCC
33181 AACCAAGCAA TGCAACTGGA TTGCGTTTCA AGCAGGAGAG GAGAGGGAAG AGACGGAAGA ACCATGTTAA
33251 TTTTTATTCC AAACGATCTC GCAGTACTTC AAATTGTAGA TCGCGCAGAT GGCATCTCTC GCCCCCACTG
33321 TGTTGGTGAA AAAGCACAGC TAAATCAAAA GAAATGCGAT TTTCAAGGTG CTCAACGGTG GCTTCCAACA
33391 AAGCCTCCAC GCGCACATCC AAGAACAAAA GAATACCAAA AGAAGGAGCA TTTTCTAACT CCTCAATCAT
33461 CATATTCAT TCCTGCACCA TTCCCAGATA ATTTTCAGCT TTCCAGCCTT GAATTATTCG TGTCAGTTCT
33531 TGTGGTAAAT CCAATCCACA CATTACAAAC AGGTCCCGGA GGGCGCCCTC CACCACCATT CTTAAACACA
33601 CCCTCATAAT GACAAATAT CTTGCTCCTG TGTCACCTGT AGCGAATTGA GAATGGCAAC ATCAATTGAC
33671 ATGCCCTTGG CTCTAAGTTC TTCTTTAAGT TCTAGTTGTA AAAACTCTCT CATATTATCA CCAAACTGCT
33741 TAGCCAGAAG CCCCCCGGGA ACAAGAGCAG GGGACGCTAC AGTGCAGTAC AAGCGCAGAC CTCCCCAATT
33811 GGCTCCAGCA AAAACAGAT TGGAATAAGC ATATTGGGAA CCACCAGTAA TATCATCGAA GTTGCTGGAA
33881 ATATAATCAG GCAGAGTTTC TTGTAGAAAT TGAATAAAAG AAAAATTTGC CAAAAAAACA TTCAAAACCT
33951 CTGGGATGCA AATGCAATAG GTTACCGCGC TGCGCTCCAA CATTGTTAGT TTTGAATTAG TCTGCAAAAA
34021 TAAAAAAAA ACAAGCGTCA TATCATAGTA GCCTGACGAA CAGGTGGATA AATCAGTCTT TCCATCACAA
34091 GACAAGCCAC AGGGTCTCCA GCTCGACCCT CGTAAACCT GTCATCGTGA TTAAACAACA GCACCGAAAG
34161 TTCCTCGCGG TGACCAGCAT GAATAAGTCT TGATGAAGCA TACAATCCAG ACATGTTAGC ATCAGTTAAG
34231 GAGAAAAAAC AGCCAACATA GCCTTTGGGT ATAATTATGC TTAATCGTAA GTATAGCAAA GCCACCCCTC
34301 GCGGATACAA AGTAAAAGGC ACAGGAGAAT AAAAAATATA ATTATTTCTC TGCTGCTGTT TAGGCAACGT
34371 CGCCCCCGGT CCCTCTAAAT ACACATACAA AGCCTCATCA GCCATGGCTT ACCAGAGAAA GTACAGCGGG
34441 CACACAAACC ACAAGCTCTA AAGTCACTCT CCAACCTSTC CACAATATAT ATACACAAGC CCTAAACTGA
34511 CGTAATGGGA CTAAAGTGTA AAAAATCCCG CCAAACCCAA CACACACCCC GAAACTGCGT CACCAGGGAA
34581 AAGTACAGTT TCACTTCCGC AATCCCAACA AGCGTCACTT CCTCTTTCTC ACGGTACGTC ACATCCCATT
34651 AACTTACAAC GTCATTTTCC CACGGCCGCG CCGCCCCTTT TAACCGTTAA CCCCACAGCC AATCACCACA
34721 CGGCCCACAC TTTTTAAAAT CACCTCATTT ACATATTGGC ACCATTCCAT CTATAAGGTA TATTATTGAT
34791 GATG
```

Figure 7: Construction of cosmid vector pWE.Ad35.pIX-rITR

SEQUENCE LISTING

<160> NUMBER OF SEQ ID NOS: 39

<210> SEQ ID NO 1
<211> LENGTH: 14
<212> TYPE: DNA
<213> ORGANISM: human adenovirus type 35

<400> SEQUENCE: 1
ccaataatat acct                                                                 14

<210> SEQ ID NO 2
<211> LENGTH: 21
<212> TYPE: DNA
<213> ORGANISM: human adenovirus type 35

<400> SEQUENCE: 2
aggtatatta ttgatgatgg g                                                         21

<210> SEQ ID NO 3
<211> LENGTH: 18
<212> TYPE: DNA
<213> ORGANISM: human adenovirus

<400> SEQUENCE: 3
catcatcaat aatatacc                                                             18

<210> SEQ ID NO 4
<211> LENGTH: 47
<212> TYPE: DNA
<213> ORGANISM: Artificial Sequence
<220> FEATURE:
<223> OTHER INFORMATION: Linker

<400> SEQUENCE: 4
tcgatggcaa acagctatta tgggtattat gggttcgaat taattaa                             47

<210> SEQ ID NO 5
<211> LENGTH: 47
<212> TYPE: DNA
<213> ORGANISM: Artificial Sequence
<220> FEATURE:
<223> OTHER INFORMATION: Linker

<400> SEQUENCE: 5
tcgattaatt aattcgaacc cataataccc ataatagctg tttgcca                             47

<210> SEQ ID NO 6
<211> LENGTH: 41
<212> TYPE: DNA
<213> ORGANISM: Artificial Sequence
<220> FEATURE:
<223> OTHER INFORMATION: PCR Primer

<400> SEQUENCE: 6
ccccaattgg tcgaccatca tcaataatat accttatttg g                                   41

<210> SEQ ID NO 7
<211> LENGTH: 22
<212> TYPE: DNA
<213> ORGANISM: Artificial Sequence
<220> FEATURE:
<223> OTHER INFORMATION: PCR Primer

<400> SEQUENCE: 7

```
gcgaaaattg tcacttcctg tg                                            22

<210> SEQ ID NO 8
<211> LENGTH: 37
<212> TYPE: DNA
<213> ORGANISM: Artificial Sequence
<220> FEATURE:
<223> OTHER INFORMATION: Linker

<400> SEQUENCE: 8
aattcggcgc gccgtcgacg atatcgatag cggccgc                            37

<210> SEQ ID NO 9
<211> LENGTH: 37
<212> TYPE: DNA
<213> ORGANISM: Artificial Sequence
<220> FEATURE:
<223> OTHER INFORMATION: Linker

<400> SEQUENCE: 9
aattgcggcc gctatcgata tcgtcgacgg cgcgccg                            37

<210> SEQ ID NO 10
<211> LENGTH: 49
<212> TYPE: DNA
<213> ORGANISM: Artificial Sequence
<220> FEATURE:
<223> OTHER INFORMATION: Linker

<400> SEQUENCE: 10
agctctagag gatccgttaa cgctagcgaa ttcaccggta ccaagctta               49

<210> SEQ ID NO 11
<211> LENGTH: 49
<212> TYPE: DNA
<213> ORGANISM: Artificial Sequence
<220> FEATURE:
<223> OTHER INFORMATION: Linker

<400> SEQUENCE: 11
ctagtaagct tggtaccggt gaattcgcta gcgttaacgg atcctctag               49

<210> SEQ ID NO 12
<211> LENGTH: 44
<212> TYPE: DNA
<213> ORGANISM: Artificial Sequence
<220> FEATURE:
<223> OTHER INFORMATION: PCR Primer

<400> SEQUENCE: 12
cggaattctt aattaatcga catcatcaat aatatacctt atag                    44

<210> SEQ ID NO 13
<211> LENGTH: 33
<212> TYPE: DNA
<213> ORGANISM: Artificial Sequence
<220> FEATURE:
<223> OTHER INFORMATION: PCR Primer

<400> SEQUENCE: 13
ggtggtccta ggctgacacc tacgtaaaaa cag                                33

<210> SEQ ID NO 14
<211> LENGTH: 30
<212> TYPE: DNA
```

```
<213> ORGANISM: Artificial Sequence
<220> FEATURE:
<223> OTHER INFORMATION: PCR Primer

<400> SEQUENCE: 14
tggtggagat ctggtgagta ttgggaaaac                                30

<210> SEQ ID NO 15
<211> LENGTH: 37
<212> TYPE: DNA
<213> ORGANISM: Artificial Sequence
<220> FEATURE:
<223> OTHER INFORMATION: PCR Primer

<400> SEQUENCE: 15
cggaattctt aattaaggga aatgcaaatc tgtgagg                        37

<210> SEQ ID NO 16
<211> LENGTH: 34
<212> TYPE: DNA
<213> ORGANISM: Artificial Sequence
<220> FEATURE:
<223> OTHER INFORMATION: PCR Primer

<400> SEQUENCE: 16
cggaattcgc ggccgcggtg agtattggga aaac                           34

<210> SEQ ID NO 17
<211> LENGTH: 21
<212> TYPE: DNA
<213> ORGANISM: Artificial Sequence
<220> FEATURE:
<223> OTHER INFORMATION: PCR Primer

<400> SEQUENCE: 17
cgccagatcg tctacagaac a                                         21

<210> SEQ ID NO 18
<211> LENGTH: 23
<212> TYPE: DNA
<213> ORGANISM: Artificial Sequence
<220> FEATURE:
<223> OTHER INFORMATION: PCR Primer

<400> SEQUENCE: 18
gaatgctggc ttcagttgta atc                                       23

<210> SEQ ID NO 19
<211> LENGTH: 42
<212> TYPE: DNA
<213> ORGANISM: Artificial Sequence
<220> FEATURE:
<223> OTHER INFORMATION: PCR Primer

<400> SEQUENCE: 19
cggaattcgc ggccgcattt aaatcatcat caataatata cc                  42

<210> SEQ ID NO 20
<211> LENGTH: 33
<212> TYPE: DNA
<213> ORGANISM: Artificial Sequence
<220> FEATURE:
<223> OTHER INFORMATION: PCR Primer

<400> SEQUENCE: 20
ggggtaccga attctcgcta gggtatttat acc                            33
```

<210> SEQ ID NO 21
<211> LENGTH: 38
<212> TYPE: DNA
<213> ORGANISM: Artificial Sequence
<220> FEATURE:
<223> OTHER INFORMATION: PCr Primer

<400> SEQUENCE: 21
gctctagacc tgcaggttag tcagtttctt ctccactg                                    38

<210> SEQ ID NO 22
<211> LENGTH: 27
<212> TYPE: DNA
<213> ORGANISM: Artificial Sequence
<220> FEATURE:
<223> OTHER INFORMATION: PCR Primer

<400> SEQUENCE: 22
ggctctagag atccttcgcg ggacgtc                                                27

<210> SEQ ID NO 23
<211> LENGTH: 26
<212> TYPE: DNA
<213> ORGANISM: Artificial Sequence
<220> FEATURE:
<223> OTHER INFORMATION: PCR Primer

<400> SEQUENCE: 23
ggcgaattca ctgccttcca ccaagc                                                 26

<210> SEQ ID NO 24
<211> LENGTH: 17
<212> TYPE: DNA
<213> ORGANISM: Artificial Sequence
<220> FEATURE:
<223> OTHER INFORMATION: Linker

<400> SEQUENCE: 24
gtgcctaggc cacgggg                                                           17

<210> SEQ ID NO 25
<211> LENGTH: 13
<212> TYPE: DNA
<213> ORGANISM: Artificial Sequence
<220> FEATURE:
<223> OTHER INFORMATION: Linker

<400> SEQUENCE: 25
gtggcctagg cac                                                               13

<210> SEQ ID NO 26
<211> LENGTH: 20
<212> TYPE: DNA
<213> ORGANISM: Artificial Sequence
<220> FEATURE:
<223> OTHER INFORMATION: PCR Primer

<400> SEQUENCE: 26
cacctctgcc taatcatctc                                                        20

<210> SEQ ID NO 27
<211> LENGTH: 27
<212> TYPE: DNA
<213> ORGANISM: Artificial Sequence
<220> FEATURE:

<223> OTHER INFORMATION: PCR Primer

<400> SEQUENCE: 27
gctctagaaa ttccactgcc ttccacc                                                      27

<210> SEQ ID NO 28
<211> LENGTH: 25
<212> TYPE: DNA
<213> ORGANISM: Artificial Sequence
<220> FEATURE:
<223> OTHER INFORMATION: PCR Primer

<400> SEQUENCE: 28
ttagatccat ggatcccgca gactc                                                        25

<210> SEQ ID NO 29
<211> LENGTH: 18
<212> TYPE: DNA
<213> ORGANISM: Artificial Sequence
<220> FEATURE:
<223> OTHER INFORMATION: PCR Primer

<400> SEQUENCE: 29
cctcagcccc atttccag                                                                18

<210> SEQ ID NO 30
<211> LENGTH: 25
<212> TYPE: DNA
<213> ORGANISM: Artificial Sequence
<220> FEATURE:
<223> OTHER INFORMATION: PCR Primer

<400> SEQUENCE: 30
ttagatccat ggatcccgca gactc                                                        25

<210> SEQ ID NO 31
<211> LENGTH: 18
<212> TYPE: DNA
<213> ORGANISM: Artificial Sequence
<220> FEATURE:
<223> OTHER INFORMATION: PCR Primer

<400> SEQUENCE: 31
cctcagcccc atttccag                                                                18

<210> SEQ ID NO 32
<211> LENGTH: 20
<212> TYPE: DNA
<213> ORGANISM: Artificial Sequence
<220> FEATURE:
<223> OTHER INFORMATION: PCR Primer

<400> SEQUENCE: 32
gagacgcccg acatcacctg                                                              20

<210> SEQ ID NO 33
<211> LENGTH: 26
<212> TYPE: DNA
<213> ORGANISM: Artificial Sequence
<220> FEATURE:
<223> OTHER INFORMATION: PCr Primer

<400> SEQUENCE: 33
caagcctcca tggggtcaga tgtaac                                                       26

<210> SEQ ID NO 34
<211> LENGTH: 21
<212> TYPE: DNA
<213> ORGANISM: Artificial Sequence
<220> FEATURE:
<223> OTHER INFORMATION: PCR Primer

<400> SEQUENCE: 34
gagcgaagaa acccatctga g                                               21

<210> SEQ ID NO 35
<211> LENGTH: 19
<212> TYPE: DNA
<213> ORGANISM: Artificial Sequence
<220> FEATURE:
<223> OTHER INFORMATION: PCR Primer

<400> SEQUENCE: 35
ggtccaggcc ggctctcgg                                                  19

<210> SEQ ID NO 36
<211> LENGTH: 18
<212> TYPE: DNA
<213> ORGANISM: Artificial Sequence
<220> FEATURE:
<223> OTHER INFORMATION: PCR Primer

<400> SEQUENCE: 36
ccgagagccg gcctggac                                                   18

<210> SEQ ID NO 37
<211> LENGTH: 38
<212> TYPE: DNA
<213> ORGANISM: Artificial Sequence
<220> FEATURE:
<223> OTHER INFORMATION: PCR Primer

<400> SEQUENCE: 37
gctctagacc tgcaggttag tcagtttctt ctccactg                             38

<210> SEQ ID NO 38
<211> LENGTH: 43
<212> TYPE: DNA
<213> ORGANISM: Artificial Sequence
<220> FEATURE:
<223> OTHER INFORMATION: PCR Primer

<400> SEQUENCE: 38
gctctagacc tgcagggtag caacaattcc ggatatttac aag                       43

<210> SEQ ID NO 39
<211> LENGTH: 34794
<212> TYPE: DNA
<213> ORGANISM: Human Adenovirus Type 35

<400> SEQUENCE: 39
catcatcaat aatatacctt atagatggaa tggtgccaat atgtaaatga ggtgatttta      60
aaaagtgtgg gccgtgtggt gattggctgt ggggttaacg gttaaaaggg cggcgcggc     120 cgtgggaaaa tgacgtttta tggggtggga gtttttttgc aagttgtcgc gggaaatgtt    180
acgcataaaa aggcttcttt tctcacggaa ctacttagtt ttcccacggt atttaacagg    240
aaatgaggta gttttgaccg gatgcaagtg aaaattgctg attttcgcgc gaaaactgaa    300
tgaggaagtg tttttctgaa taatgtgtta tttatggcag ggtggagtat ttgttcaggg    360

-continued

| | | | | |
|---|---|---|---|---|
| ccaggtagac | tttgacccat | tacgtggagg | tttcgattac | cgtgtttttt acctgaattt | 420 |
| ccgcgtaccg | tgtcaaagtc | ttctgttttt | acgtaggtgt | cagctgatcg ctagggtatt | 480 |
| tatacctcag | gtttgtgtc | aagaggccac | tcttgagtgc | cagcgagaag agttttctcc | 540 |
| tctgcgccgg | cagtttaata | ataaaaaaat | gagagatttg | cgatttctgc ctcaggaaat | 600 |
| aatctctgct | gagactggaa | atgaaatatt | ggagcttgtg | gtgcacgccc tgatgggaga | 660 |
| cgatccggag | ccacctgtgc | agcttttga | gcctcctacg | cttcaggaac tgtatgattt | 720 |
| agaggtagag | ggatcggagg | attctaatga | ggaagctgtg | aatggctttt ttaccgattc | 780 |
| tatgcttta | gctgctaatg | aaggattaga | attagatccg | cctttggaca ctttcaatac | 840 |
| tccagggtg | attgtggaaa | gcggtacagg | tgtaagaaaa | ttacctgatt tgagttccgt | 900 |
| ggactgtgat | ttgcactgct | atgaagacgg | gttcctccg | agtgatgagg aggaccatga | 960 |
| aaaggagcag | tccatgcaga | ctgcagcggg | tgagggagtg | aaggctgcca atgttggttt | 1020 |
| tcagttggat | tgcccggagc | ttcctggaca | tggctgtaag | tcttgtgaat tcacaggaa | 1080 |
| aaatactgga | gtaaaggaac | tgttatgttc | gctttgttat | atgagaacgc actgccactt | 1140 |
| tatttacagt | aagtgtgttt | aagttaaaat | ttaaaggaat | atgctgtttt tcacatgtat | 1200 |
| attgagtgtg | agttttgtgc | ttcttattat | aggtcctgtg | tctgatgctg atgaatcacc | 1260 |
| atctcctgat | tctactacct | cacctcctga | tattcaagca | cctgttcctg tggacgtgcg | 1320 |
| caagcccatt | cctgtgaagc | ttaagcctgg | gaaacgtcca | gcagtggaga aacttgagga | 1380 |
| cttgttacag | ggtggggacg | gacctttgga | cttgagtaca | cggaaacgtc caagacaata | 1440 |
| agtgttccat | atccgtgttt | acttaaggtg | acgtcaatat | ttgtgtgaga gtgcaatgta | 1500 |
| ataaaaatat | gttaactgtt | cactggtttt | tattgctttt | tgggcgggga ctcaggtata | 1560 |
| taagtagaag | cagacctgtg | tggttagctc | ataggagctg | gctttcatcc atggaggttt | 1620 |
| gggccatttt | ggaagacctt | aggaagacta | ggcaactgtt | agagagcgct tcggacggag | 1680 |
| tctccggttt | ttggagattc | tggttcgcta | gtgaattagc | tagggtagtt tttaggataa | 1740 |
| aacaggacta | taaacaagaa | tttgaaaagt | tgttggtaga | ttgcccagga cttttgaag | 1800 |
| ctcttaattt | gggccatcag | gttcacttta | agaaaaagt | tttatcagtt ttagactttt | 1860 |
| caaccccagg | tagaactgct | gctgctgtgg | cttttcttac | ttttatatta gataaatgga | 1920 |
| tcccgcagac | tcatttcagc | agggatacg | ttttggattt | catagccaca gcattgtgga | 1980 |
| gaacatggaa | ggttcgcaag | atgaggacaa | tcttaggtta | ctggccagtg cagcctttgg | 2040 |
| gtgtagcggg | aatcctgagg | catccaccgg | tcatgccagc | ggttctggag gaggaacagc | 2100 |
| aagaggacaa | cccgagagcc | ggcctggacc | ctccagtgga | ggaggcggag tagctgactt | 2160 |
| gtctcctgaa | ctgcaacggg | tgcttactgg | atctacgtcc | actggacggg ataggggcgt | 2220 |
| taagagggag | agggcatcca | gtggtactga | tgctagatct | gagttggctt taagtttaat | 2280 |
| gagtcgcaga | cgtcctgaaa | ccatttggtg | gcatgaggtt | cagaaagagg aagggatga | 2340 |
| agtttctgta | ttgcaggaga | aatattcact | ggaacaggtg | aaaacatgtt ggttggagcc | 2400 |
| agaggatgat | tgggcggtgg | ccattaaaaa | ttatgccaag | atagctttga ggcctgataa | 2460 |
| acagtataag | atcagtagac | ggattaatat | ccggaatgct | tgttacatat ctggaaatgg | 2520 |
| ggctgaggtg | gtaatagata | tcaagacaa | gacagttatt | agatgctgca tgatggatat | 2580 |
| gtggcctgga | gtagtcggta | tggaagcagt | cactttgta | aatgttaagt ttaggggaga | 2640 |
| tggttataat | ggaatagtgt | ttatggccaa | taccaaactt | atattgcatg ttgtagctt | 2700 |
| ttttggtttc | aacaatacct | gtgtagatgc | ctggggacag | gttagtgtac gggggtgtag | 2760 |

```
tttctatgcg tgttggattg ccacagctgg cagaaccaag agtcaattgt ctctgaagaa    2820
atgcatattc caaagatgta acctgggcat tctgaatgaa ggcgaagcaa gggtccgtca    2880
ctgcgcttct acagatactg gatgttttat tttaattaag ggaaatgcca gcgtaaagca    2940
taacatgatt tgtggtgctt ccgatgagag gccttatcaa atgctcactt gtgctggtgg    3000
gcattgtaat atgctggcta ctgtgcatat tgtttcccat caacgcaaaa aatggcctgt    3060
ttttgatcac aatgtgttga ccaagtgcac catgcatgca ggtgggcgta gaggaatgtt    3120
tatgccttac cagtgtaaca tgaatcatgt gaaagtgttg ttggaaccag atgccttttc    3180
cagaatgagc ctaacaggaa tctttgacat gaacacgcaa atctggaaga tcctgaggta    3240
tgatgatacg agatcgaggg tgcgcgcatg cgaatgcgga ggcaagcatg ccaggttcca    3300
gccggtgtgt gtagatgtga ccgaagatct cagaccggat catttggtta ttgcccgcac    3360
tggagcagag ttcggatcca gtggagaaga aactgactaa ggtgagtatt gggaaaactt    3420
tggggtggga ttttcagatg gacagattga gtaaaaattt gtttttttctg tcttgcagct    3480
gacatgagtg gaaatgcttc ttttaagggg ggagtcttca gcccttatct gacagggcgt    3540
ctcccatcct gggcaggagt tcgtcagaat gttatgggat ctactgtgga tggaagaccc    3600
gttcaacccg ccaattcttc aacgctgacc tatgctactt taagttcttc acctttggac    3660
gcagctgcag ccgctgccgc cgcctctgtc gccgctaaca ctgtgcttgg aatgggttac    3720
tatggaagca tcgtggctaa ttccacttcc tctaataacc cttctacact gactcaggac    3780
aagttacttg tccttttggc ccagctggag gctttgaccc aacgtctggg tgaactttct    3840
cagcaggtgg ccgagttgcg agtacaaact gagtctgctg tcggcacggc aaagtctaaa    3900
taaaaaaaat tccagaatca atgaataaat aaacgagctt gttgttgatt taaaatcaag    3960
tgttttatt tcattttttcg cgcacggtat gccctggacc accgatctcg atcattgaga    4020
actcggtgga ttttttccag aatcctatag aggtgggatt gaatgtttag atacatgggc    4080
attaggccgt ctttggggtg gagatagctc cattgaaggg attcatgctc cggggtagtg    4140
ttgtaaatca cccagtcata acaaggtcgc agtgcatggt gttgcacaat atcttttaga    4200
agtaggctga ttgccacaga taagcccttg gtgtaggtgt ttacaaaccg gttgagctgg    4260
gagggtgca ttcgaggtga aattatgtgc attttggatt ggatttttaa gttggcaata    4320
ttgccgccaa gatcccgtct tgggttcatg ttatgaagga ctaccaagac ggtgtatccg    4380
gtacatttag gaaatttatc gtgcagcttg gatggaaaag cgtggaaaaa tttggagaca    4440
cccttgtgtc ctccgagatt ttccatgcac tcatccatga taatagcaat ggggccgtgg    4500
gcagcggcgc gggcaaacac gttccgtggg tctgacacat catagttatg ttcctgagtt    4560
aaatcatcat aagccatttt aatgaatttg gggcggagcg taccagattg gggtatgaat    4620
gttccttcgg gccccggagc atagttcccc tcacagattt gcatttccca agctttcagt    4680
tctgagggtg gaatcatgtc cacctggggg gctatgaaga acaccgtttc ggggggcgggg    4740
gtgattagtt gggatgatag caagtttctg agcaattgag atttgccaca tccggtgggg    4800
ccataaataa ttccgattac aggttgcagg tggtagttta gggaacggca actgccgtct    4860
tctcgaagca agggggccac ctcgttcatc atttcccctta catgcatatt ttcccgcacc    4920
aaatccatta ggaggcgctc tcctcctagt gatagaagtt cttgtagtga ggaaaagttt    4980
ttcagcggtt ttagaccgtc agccatgggc attttgaaaa gagtttgctg caaaagttct    5040
agtctgttcc acagttcagt gatgtgttct atggcatctc gatccagcag acctcctcgt    5100
```

-continued

```
ttcgcgggtt tggacggctc ctggagtagg gtatgagacg atgggcgtcc agcgctgcca      5160
gggttcggtc cttccagggt ctcagtgttc gagtcaggqt tgtttccgtc acagtgaagg      5220
ggtgtgcgcc tgcttgggcg cttgccaggg tgcgcttcag actcattctg ctggtggaga      5280
acttctgtcg cttggcgccc tgtatgtcgg ccaagtagca gtttaccatg agttcgtagt      5340
tgagcgcctc ggctgcgtgg cctttggcgc ggagcttacc tttggaagtt ttcttgcata      5400
ccgggcagta taggcatttc agcgcataca gcttggcgcg aaggaaaatg gattctgggg      5460
agtatgcatc cgcgccgcag gaggcgcaaa cagtttcaca ttccaccagc caggttaaat      5520
ccggttcatt ggggtcaaaa acaagttttc cgccatattt tttgatgcgt ttcttacctt      5580
tggtctccat aagttcgtgt cctcgttgag tgacaaacag gctgtccgta tctccgtaga      5640
ctgattttac aggcctcttc tccagtggag tgcctcggtc ttcttcgtac aggaactctg      5700
accactctga tacaaaggcg cgcgtccagg ccagcacaaa ggaggctatg tgggaggggt      5760
agcgatcgtt gtcaaccagg gggtccacct tttccaaagt atgcaaacac atgtcaccct      5820
cttcaacatc caggaatgtg attggcttgt aggtgtattt cacgtgacct ggggtccccg      5880
ctgggggggt ataaaagggg gcggttcttt gctcttcctc actgtcttcc ggatcgctgt      5940
ccaggaacgt cagctgttgg ggtaggtatt ccctctcgaa ggcgggcatg acctctgcac      6000
tcaggttgtc agtttctaag aacgaggagg atttgatatt gacagtgccg gttgagatgc      6060
ctttcatgag gttttcgtcc atttggtcag aaaacacaat ttttttattg tcaagtttgg      6120
tggcaaatga tccatacagg gcgttggata aagtttggc aatggatcgc atggtttggt      6180
tcttttcctt gtccgcgcgc tctttggcgg cgatgttgag ttggacatac tcgcgtgcca      6240
ggcacttcca ttcggggaag atagttgtta attcatctgg cacgattctc acttgccacc      6300
ctcgattatg caaggtaatt aaatccacac tggtggccac ctcgcctcga aggggttcat      6360
tggtccaaca gagcctacct cctttcctag aacagaaagg gggaagtggg tctagcataa      6420
gttcatcggg agggtctgca tccatggtaa agattcccgg aagtaaatcc ttatcaaaat      6480
agctgatggg agtggggtca tctaaggcca tttgccattc tcgagctgcc agtgcgcgct      6540
catatgggtt aaggggactg ccccagggca tgggatgggt gagagcagag gcatacatgc      6600
cacagatgtc atagacgtag atgggatcct caaagatgcc tatgtaggtt ggatagcatc      6660
gcccccctct gatacttgct cgcacatagt catatagttc atgtgatggc gctagcagcc      6720
ccggacccaa gttggtgcga ttgggttttt ctgttctgta gacgatctgg cgaaagatgg      6780
cgtgagaatt ggaagagatg gtgggtcttt gaaaaatgtt gaaatgggca tgaggtagac      6840
ctacagagtc tctgacaaag tgggcataag attcttgaag cttggttacc agttcggcgg      6900
tgacaagtac gtctagggcg cagtagtcaa gtgtttcttg aatgatgtca taacctggtt      6960 ggttttttctt ttcccacagt tcgcggttga aaggtattc ttcgcgatcc ttccagtact      7020
cttctagcgg aaacccgtct ttgtctgcac ggtaagatcc tagcatgtag aactgattaa      7080
ctgccttgta agggcagcag cccttctcta cgggtagaga gtatgcttga gcagcttttc      7140
gtagcgaagc gtgagtaagg gcaaaggtgt ctctgaccat gactttgaga aattggtatt      7200
tgaagtccat gtcgtcacag gctccctgtt cccagagttg gaagtctacc cgtttcttgt      7260
aggcggggtt gggcaaagcg aaagtaacat cattgaagag aatcttaccg gctctgggca      7320
taaaattgcg agtgatgcgg aaaggctgtg gtacttccgc tcgattgttg atcacctggg      7380
cagctaggac gatttcgtcg aaaccgttga tgttgtgtcc tacgatgtat aattctatga      7440
aacgcggcgt gcctctgacg tgaggtagct tactgagctc atcaaaggtt aggtctgtgg      7500
```

-continued

```
ggtcagataa ggcgtagtgt tcgagagccc attcgtgcag gtgaggattt gcatgtagga      7560
atgatgacca aagatctacc gccagtgctg tttgtaactg gtcccgatac tgacgaaaat      7620
gccggccaat tgccattttt tctggagtga cacagtagaa ggttctgggg tcttgttgcc      7680
atcgatccca cttgagttta atggctagat cgtgggccat gttgacgaga cgctcttctc      7740
ctgagagttt catgaccagc atgaaaggaa ctagttgttt gccaaaggat cccatccagg      7800
tgtaagtttc cacatcgtag gtcaggaaga gtctttctgt gcgaggatga gagccgatcg      7860
ggaagaactg gatttcctgc caccagttgg aggattggct gttgatgtga tggaagtaga      7920
agtttctgcg gcgcgccgag cattcgtgtt tgtgcttgta cagacggccg cagtagtcgc      7980
agcgttgcac gggttgtatc tcgtgaatga gctgtacctg gcttcccttg acgagaaatt      8040
tcagtgggaa gccgaggcct ggcgattgta tctcgtgctc ttctatattc gctgtatcgg      8100
cctgttcatc ttctgtttcg atggtggtca tgctgacgag ccccgcgggg aggcaagtcc      8160
agacctcggc gcgggagggg cggagctgaa ggacgagagc gcgcaggctg agctgtcca      8220 gagtcctgag acgctgcgga ctcaggttag taggtaggga cagaagatta acttgcatga      8280
tcttttccag ggcgtgcggg aggttcagat ggtacttgat ttccacaggt tcgtttgtag      8340
agacgtcaat ggcttgcagg gttccgtgtc ctttgggcgc cactaccgta cctttgtttt      8400
ttcttttgat cggtggtggc tctcttgctt cttgcatgct cagaagcggt gacggggacg      8460
cgcgccgggc ggcagcggtt gttccggacc cgggggcatg gctggtagtg gcacgtcggc      8520
gccgcgcacg ggcaggttct ggtattgcgc tctgagaaga cttgcgtgcg ccaccacgcg      8580
tcgattgacg tcttgtatct gacgtctctg ggtgaaagct accggccccg tgagcttgaa      8640
cctgaaagag agttcaacag aatcaatttc ggtatcgtta acggcagctt gtctcagtat      8700
ttcttgtacg tcaccagagt tgtcctggta ggcgatctcc gccatgaact gctcgatttc      8760
ttcctcctga agatctccgc gacccgctct ttcgacggtg gccgcgaggt cattggagat      8820
acggcccatg agttgggaga atgcattcat gcccgcctcg ttccagacgc ggctgtaaac      8880
cacggccccc tcggagtctc ttgcgcgcat caccacctga gcgaggttaa gctccacgtg      8940
tctggtgaag accgcatagt tgcataggcg ctgaaaaagg tagttgagtg tggtggcaat      9000
gtgttcggcg acgaagaaat acatgatcca tcgtctcagc ggcatttcgc taacatcgcc      9060
cagagcttcc aagcgctcca tggcctcgta gaagtccacg gcaaaattaa aaaactggga      9120
gtttcgcgcg gacacggtca attcctcctc gagaagacgg atgagttcgg ctatggtggc      9180
ccgtacttcg cgttcgaagg ctcccgggat ctcttcttcc tcttctatct cttcttccac      9240
taacatctct tcttcgtctt caggcggggg cggagggggc acgcggcgac gtcgacggcg      9300
cacgggcaaa cggtcgatga atcgttcaat gacctctccg cggcggcggc gcatggtttc      9360
agtgacggcg cggccgttct cgcgcggtcg cagagtaaaa acaccgccgc gcatctcctt      9420
aaagtggtga ctgggaggtt ctccgtttgg gagggagagg gcgctgatta tacattttat      9480
taattggccc gtagggactg cgcgcagaga tctgatcgtg tcaagatcca cgggatctga      9540 aaaccttcg acgaaagcgt ctaaccagtc acagtcacaa ggtaggctga gtacggcttc      9600 ttgtgggcg gggtggttat gtgttcggtc tgggtcttct gtttcttctt catctcggga      9660
aggtgagacg atgctgctgg tgatgaaatt aaagtaggca gttctaagac ggcggatggt      9720
ggcgaggagc accaggtctt tgggtccggc ttgctggata cgcaggcgat tggccattcc      9780
ccaagcatta tcctgacatc tagcaagatc tttgtagtag tcttgcatga gccgttctac      9840
```

-continued

```
gggcacttct tcctcacccg ttctgccatg catacgtgtg agtccaaatc cgcgcattgg    9900
ttgtaccagt gccaagtcag ctacgactct ttcggcgagg atggcttgct gtacttgggt    9960
aagggtggct tgaaagtcat caaaatccac aaagcggtgg taagcccctg tattaatggt   10020
gtaagcacag ttggccatga ctgaccagtt aactgtctgg tgaccagggc cacgagctc    10080
ggtgtattta aggcgcgaat aggcgcgggt gtcaaagatg taatcgttgc aggtgcgcac   10140
cagatactgg taccctataa gaaaatgcgg cggtggttgg cggtagagag gccatcgttc   10200
tgtagctgga gcgccagggg cgaggtcttc aacataagg cggtgatagc cgtagatgta    10260
cctggacatc caggtgattc ctgcggcggt agtagaagcc cgaggaaact cgcgtacgcg   10320
gttccaaatg ttgcgtagcg gcatgaagta gttcattgta ggcacggttt gaccagtgag   10380
gcgcgcgcag tcattgatgc tctatagaca cggagaaaat gaaagcgttc agcgactcga   10440
ctccgtagcc tggaggaacg tgaacgggtt gggtcgcggt gtaccccggt tcgagacttg   10500
tactcgagcc ggccggagcc gcggctaacg tggtattggc actcccgtct cgacccagcc   10560
tacaaaaatc caggatacgg aatcgagtcg ttttgctggt ttccgaatgg cagggaagtg   10620
agtcctattt tttttttttt tttgccgctc agatgcatcc cgtgctgcga cagatgcgcc   10680
cccaacaaca gccccctcg cagcagcagc agcagcaacc acaaaaggct gtccctgcaa     10740
ctactgcaac tgccgccgtg agcggtgcgg gacagcccgc ctatgatctg gacttggaag   10800
agggcgaagg actggcacgt ctaggtgcgc cttcgcccga gcggcatccg cgagttcaac   10860
tgaaaaaaga ttctcgcgag gcgtatgtgc cccaacagaa cctatttaga gacagaagcg   10920
gcgaggagcc ggaggagatg cgagcttccc gctttaacgc gggtcgtgag ctgcgtcacg   10980
gtttggaccg aagacgagtg ttgcgagacg aggatttcga agttgatgaa gtgacaggga   11040
tcagtcctgc cagggcacac gtggctgcag ccaaccttgt atcggcttac gagcagacag   11100
taaggaaga gcgtaacttc caaaagtctt ttaataatca tgtgcgaacc ctgattgccc    11160
gcgaagaagt taccttggt ttgatgcatt tgtgggattt gatggaagct atcattcaga    11220
accctactag caaacctctg accgccagc tgtttctggt ggtgcaacac agcagagaca    11280
atgaggcttt cagagaggcg ctgctgaaca tcaccgaacc cgagggagat ggttgtatg    11340
atcttatcaa cattctacag agtatcatag tgcaggagcg gagcctgggc ctggccgaga   11400
aggtagctgc catcaattac tcggttttga gcttgggaaa atattacgct cgcaaaatct   11460
acaagactcc atacgttccc atagacaagg aggtgaagat agatgggttc tacatgcgca   11520
tgacgctcaa ggtcttgacc ctgagcgatg atcttggggt gtatcgcaat gacagaatgc   11580
atcgcgcggt tagcgccagc aggaggcgcg agttaagcga cagggaactg atgcacagtt   11640
tgcaaagagc tctgactgga gctggaaccg agggtgagaa ttacttcgac atgggagctg   11700
acttgcagtg gcagcctagt cgcagggctc tgagcgccgc gacggcagga tgtgagcttc   11760
cttacataga agaggcggat gaaggcgagg aggaagaggg cgagtacttg gaagactgat   11820
ggcacaaccc gtgttttttg ctagatggaa cagcaagcac cggatcccgc aatgcgggcg   11880
gcgctgcaga gccagccgtc cggcattaac tcctcggacg attggaccca ggccatgcaa   11940
cgtatcatgg cgttgacgac tcgcaacccc gaagcctta dacagcaacc ccaggccaac    12000
cgtctatcgg ccatcatgga agctgtagtg ccttcccgat ctaatcccac tcatgagaag   12060
gtcctggcca tcgtgaacgc gttggtggag aacaaagcta ttcgtccaga tgaggccgga   12120
ctggtataca cgctctctt agaacgcgtg gctcgctaca acagtagcaa tgtgcaaacc    12180
aatttggacc gtatgataac agatgtacgc gaagccgtgt ctcagcgcga aaggttccag   12240
```

```
cgtgatgcca acctgggttc gctggtggcg ttaaatgctt tcttgagtac tcagcctgct   12300
aatgtgccgc gtggtcaaca ggattatact aactttttaa gtgctttgag actgatggta   12360
tcagaagtac ctcagagcga agtgtatcag tccggtcctg attacttctt tcagactagc   12420
agacagggct tgcagacggt aaatctgagc caagctttta aaaaccttaa aggtttgtgg   12480
ggagtgcatg ccccggtagg agaaagagca accgtgtcta gcttgttaac tccgaactcc   12540
cgcctgttat tactgttggt agctcctttc accgacagcg gtagcatcga ccgtaattcc   12600
tatttgggtt acctactaaa cctgtatcgc gaagccatag ggcaaagtca ggtggacgag   12660
cagacctatc aagaaattac ccaagtcagt cgcgctttgg gacaggaaga cactggcagt   12720
ttggaagcca ctctgaactt cttgcttacc aatcggtctc aaaagatccc tcctcaatat   12780
gctcttactg cggaggagga gaggatcctt agatatgtgc agcagagcgt gggattgttt   12840
ctgatgcaag aggggcaac tccgactgca gcactggaca tgacagcgcg aaatatggag   12900
cccagcatgt atgccagtaa ccgacctttc attaacaaac tgctggacta cttgcacaga   12960
gctgccgcta tgaactctga ttatttcacc aatgccatct aaacccgca ctggctgccc   13020 ccacctggtt tctacacggg cgaatatgac atgcccgacc ctaatgacgg atttctgtgg   13080
gacgacgtgg acagcgatgt ttttcacct ctttctgatc atcgcacgtg aaaaaggaa    13140 ggcggtgata gaatgcattc ttctgcatcg ctgtccgggg tcatgggtgc taccgcggct   13200
gagcccgagt ctgcaagtcc ttttcctagt ctacccttt ctctacacag tgtacgtagc    13260
agcgaagtgg gtagaataag tcgcccgagt ttaatgggcg aagaggagta cctaaacgat   13320
tccttgctca gaccggcaag agaaaaaat ttcccaaaca atggaataga agtttggtg     13380 gataaaatga gtagatggaa gacttatgct caggatcaca gagacgagcc tgggatcatg   13440
gggactacaa gtagagcgag ccgtagacgc cagcgccatg acagacagag gggtcttgtg   13500
tgggacgatg aggattcggc cgatgatagc agcgtgttgg acttgggtgg gagaggaagg   13560
ggcaacccgt ttgctcattt gcgccctcgc ttgggtggta tgttgtgaaa aaaaataaaa   13620
aagaaaaact caccaaggcc atggcgacga gcgtacgttc gttcttcttt attatctgtg   13680
tctagtataa tgaggcgagt cgtgctaggc ggagcggtgg tgtatccgga gggtcctcct   13740
ccttcgtacg agagcgtgat gcagcagcag caggcgacgg cggtgatgca atccccactg   13800
gaggctccct ttgtgcctcc gcgatacctg gcacctacgg agggcagaaa cagcattcgt   13860
tactcggaac tggcacctca gtacgatacc accaggttgt atctggtgga caacaagtcg   13920
gcggacattg cttctctgaa ctatcagaat gaccacagca acttcttgac cacggtggtg   13980
cagaacaatg actttacccc tacgaagcc agcacccaga ccattaactt tgatgaacga    14040
tcgcggtggg gcggtcagct aaagaccatc atgcatacta acatgccaaa cgtgaacgag   14100
tatatgttta gtaacaagtt caaagcgcgt gtgatggtgt ccagaaaacc tcccgacggt   14160
gctgcagttg gggatactta tgatcacaag caggatattt tggaatatga gtggttcgag   14220
tttactttgc cagaaggcaa ctttcagtt actatgacta tgatttgat gaacaatgcc    14280 atcatagata attacttgaa agtgggtaga cagaatggag tgcttgaaag tgacattggt   14340
gttaagttcg acaccaggaa cttcaagctg ggatgggatc cgaaaccaa gttgatcatg   14400 cctggagtgt atacgtatga agccttccat cctgacattg tcttactgcc tggctgcgga   14460
gtggatttta ccgagagtcg tttgagcaac cttcttggta tcagaaaaaa acagccattt   14520
caagagggtt ttaagatttt gtatgaagat ttagaaggtg gtaatattcc ggccctcttg   14580
```

```
gatgtagatg cctatgagaa cagtaagaaa gaacaaaaag ccaaaataga agctgctaca    14640
gctgctgcag aagctaaggc aaacatagtt gccagcgact ctacaagggt tgctaacgct    14700
ggagaggtca gaggagacaa ttttgcgcca acacctgttc cgactgcaga atcattattg    14760
gccgatgtgt ctgaaggaac ggacgtgaaa ctcactattc aacctgtaga aaagatagt     14820
aagaatagaa gctataatgt gttggaagac aaaatcaaca cagcctatcg cagttggtat    14880
ctttcgtaca attatggcga tcccgaaaaa ggagtgcgtt cctggacatt gctcaccacc    14940
tcagatgtca cctgcggagc agagcaggtt tactggtcgc ttccagacat gatgaaggat    15000
cctgtcactt tccgctccac tagacaagtc agtaactacc ctgtggtggg tgcagagctt    15060
atgcccgtct tctcaaagag cttctacaac gaacaagctg tgtactccca gcagctccgc    15120
cagtccacct cgcttacgca cgtcttcaac cgctttcctg agaaccagat tttaatccgt    15180
ccgccggcgc ccaccattac caccgtcagt gaaaacgttc ctgctctcac agatcacggg    15240
accctgccgt tgcgcagcag tatccgggga gtccaacgtg tgaccgttac tgacgccaga    15300
cgccgcacct gtccctacgt gtacaaggca ctgggcatag tcgcaccgcg cgtcctttca    15360
agccgcactt tctaaaaaaa aaaaatgtcc attcttatct cgcccagtaa taacaccggt    15420
tggggtctgc gcgctccaag caagatgtac ggaggcgcac gcaaacgttc tacccaacat    15480
cccgtgcgtg ttcgcggaca ttttcgcgct ccatggggtg ccctcaaggg ccgcactcgc    15540
gttcgaacca ccgtcgatga tgtaatcgat caggtggttg ccgacgcccg taattatact    15600
cctactcgc ctacatctac tgtggatgca gttattgaca gtgtagtggc tgacgctcgc     15660
aactatgctc gacgtaagag ccggcgaagg cgcattgcca gacgccaccg agctaccact    15720
gccatgcgag ccgcaagagc tctgctacga agagctagac gcgtggggcg aagagccatg    15780
cttagggcgg ccagacgtgc agcttcgggc gccagcgccg gcaggtcccg caggcaagca    15840
gccgctgtcg cagcggcgac tattgccgac atggcccaat cgcgaagagg caatgtatac    15900
tgggtgcgtg acgctgccac cggtcaacgt gtacccgtgc gcacccgtcc ccctcgcact    15960
tagaagatac tgagcagtct ccgatgttgt gtcccagcgg cgaggatgtc caagcgcaaa    16020
tacaaggaag aaatgctgca ggttatcgca cctgaagtct acggccaacc gttgaaggat    16080
gaaaaaaaac cccgcaaaat caagcgggtt aaaaaggaca aaaagaaga ggaagatggc      16140
gatgatgggc tggcggagtt tgtgcgcgag tttgccccac ggcgacgcgt gcaatggcgt    16200
gggcgcaaag ttcgacatgt gttgagacct ggaacttcgg tggtctttac acccggcgag    16260
cgttcaagcg ctacttttaa gcgttcctat gatgaggtgt acggggatga tgatattctt    16320
gagcaggcgg ctgaccgatt aggcgagttt gcttatggca agcgtagtag aataacttcc    16380
aaggatgaga cagtgtcaat acccttggat catggaaatc ccaccctag tcttaaaccg      16440
gtcactttgc agcaagtgtt acccgtaact ccgcgaacag gtgttaaacg cgaaggtgaa    16500
gatttgtatc ccactatgca actgatggta cccaaacgcc agaagttgga ggacgttttg    16560
gagaaagtaa aagtggatcc agatattcaa cctgaggtta aagtgagacc cattaagcag    16620
gtagcgcctg gtctgggggt acaaactgta gacattaaga ttcccactga agtatggaa     16680
gtgcaaactg aacccgcaaa gcctactgcc acctccactg aagtgcaaac ggatccatgg    16740
atgcccatgc ctattacaac tgacgccgcc ggtcccactc gaagatcccg acgaaagtac    16800
ggtccagcaa gtctgttgat gcccaattat gttgtacacc catctattat tcctactcct    16860
ggttaccgag gcactcgcta ctatcgcagc cgaaacagta cctcccgccg tcgccgcaag    16920
acacctgcaa atcgcagtcg tcgccgtaga cgcacaagca aaccgactcc cggcgccctg    16980
```

```
gtgcggcaag tgtaccgcaa tggtagtgcg gaacctttga cactgccgcg tgcgcgttac   17040
catccgagta tcatcactta atcaatgttg ccgctgcctc cttgcagata tggccctcac   17100
ttgtcgcctt cgcgttccca tcactggtta ccgaggaaga aactcgcgcc gtagaagagg   17160
gatgttggga cgcggaatgc gacgctacag gcgacggcgt gctatccgca agcaattgcg   17220
gggtggtttt ttaccagcct taattccaat tatcgctgct gcaattggcg cgataccagg   17280
catagcttcc gtggcggttc aggcctcgca acgacattga cattggaaaa aaacgtata    17340 aataaaaaaa aatacaatgg actctgacac tcctggtcct gtgactatgt tttcttagag   17400
atggaagaca tcaattttc atccttggct ccgcgacacg gcacgaagcc gtacatgggc    17460
acctggagcg acatcggcac gagccaactg aacgggggcg ccttcaattg gagcagtatc   17520
tggagcgggc ttaaaaattt tggctcaacc ataaaaacat acgggaacaa agcttggaac   17580
agcagtacag gacaggcgct tagaaataaa cttaaagacc agaacttcca acaaaaagta   17640
gtcgatggga tagcttccgg catcaatgga gtggtagatt tggctaacca ggctgtgcag   17700
aaaaagataa acagtcgttt ggacccgccg ccagcaaccc caggtgaaat gcaagtggag   17760
gaagaaattc ctccgccaga aaacgaggc gacaagcgtc cgcgtcccga tttggaagag    17820
acgctggtga cgcgcgtaga tgaaccgcct tcttatgagg aagcaacgaa gcttggaatg   17880
cccaccacta gaccgatagc cccaatggcc accggggtga tgaaaccttc tcagttgcat   17940
cgacccgtca ccttggattt gccccctccc cctgctgcta ctgctgtacc cgcttctaag   18000
cctgtcgctg ccccgaaacc agtcgccgta gccaggtcac gtcccggggg cgctcctcgt   18060
ccaaatgcgc actggcaaaa tactctgaac agcatcgtgg gtctaggcgt gcaaagtgta   18120
aaacgccgtc gctgcttta attaaatatg gagtagcgct taacttgcct atctgtgtat    18180
atgtgtcatt acacgccgtc acagcagcag aggaaaaaag gaagaggtcg tgcgtcgacg   18240
ctgagttact ttcaagatgg ccaccccatc gatgctgccc caatgggcat acatgcacat   18300
cgccggacag gatgcttcgg agtacctgag tccgggtctg gtgcagttcg cccgcgccac   18360
agacacctac ttcaatctgg gaaataagtt tagaaatccc accgtagcgc cgacccacga   18420
tgtgaccacc gaccgtagcc agcggctcat gttgcgcttc gtgcccgttg accgggagga   18480
caatacatac tcttacaaag tgcggtacac cctggccgtg ggcgacaaca gagtgctgga   18540 tatgccagc acgttctttg acattagggg cgtgttggac agaggtccca gtttcaaacc    18600
ctattctggt acggcttaca actctctggc tcctaaaggc gctccaaatg catctcaatg   18660
gattgcaaaa ggcgtaccaa ctgcagcagc cgcaggcaat ggtgaagaag aacatgaaac   18720
agaggagaaa actgctactt acactttgc caatgctcct gtaaaagccg aggctcaaat    18780
tacaaaagag ggcttaccaa taggtttgga gatttcagct gaaaacgaat ctaaacccat   18840
ctatgcagat aaactttatc agccagaacc tcaagtggga gatgaaactt ggactgacct   18900
agacggaaaa accgaagagt atggaggcag ggctctaaag cctactacta acatgaaacc   18960
ctgttacggg tcctatgcga agcctactaa tttaaaggt ggtcaggcaa aaccgaaaaa    19020
ctcggaaccg tcgagtgaaa aaattgaata tgatattgac atggaatttt tgataactc    19080 atcgcaaaga acaaacttca gtcctaaaat tgtcatgtat gcagaaaatg taggtttgga   19140
aacgccagac actcatgtag tgtacaaacc tggaacagaa gacacaagtt ccgaagctaa   19200
tttgggacaa cagtctatgc ccaacagacc caactacatt ggcttcagag ataactttat   19260
tggactcatg tactataaca gtactggtaa catgggggtg ctggctggtc aagcgtctca   19320
```

```
gttaaatgca gtggttgact tgcaggacag aaacacagaa cttcttacc aactcttgct    19380
tgactctctg ggcgacagaa ccagatactt tagcatgtgg aatcaggctg tggacagtta   19440
tgatcctgat gtacgtgtta ttgaaaatca tggtgtggaa gatgaacttc ccaactattg   19500
ttttccactg gacggcatag gtgttccaac aaccagttac aaatcaatag ttccaaatgg   19560
agaagataat aataattgga aagaacctga agtaaatgga acaagtgaga tcggacaggg   19620
taatttgttt gccatggaaa ttaaccttca agccaatcta tggcgaagtt tcctttattc   19680
caatgtggct ctgtatctcc cagactcgta caaatacacc ccgtccaatg tcactcttcc   19740
agaaaacaaa aacacctacg actacatgaa cgggcgggtg gtgccgccat ctctagtaga   19800
cacctatgtg aacattggtg ccaggtggtc tctggatgcc atggacaatg tcaacccatt   19860
caaccaccac cgtaacgctg gcttgcgtta ccgatctatg cttctgggta acggacgtta   19920
tgtgcctttc cacatacaag tgcctcaaaa attcttcgct gttaaaaacc tgctgcttct   19980
cccaggctcc tacacttatg agtggaactt taggaaggat gtgaacatgg ttctacagag   20040
ttccctcggt aacgacctgc gggtagatgg cgccagcatc agtttcacga gcatcaacct   20100
ctatgctact ttttccccca tggctcacaa caccgcttcc acccttgaag ccatgctgcg   20160
gaatgacacc aatgatcagt cattcaacga ctacctatct gcagctaaca tgctctaccc   20220
cattcctgcc aatgcaacca atattcccat ttccattcct tctcgcaact gggcggcttt   20280
cagaggctgg tcatttacca gactgaaaac caaagaaact ccctctttgg ggtctggatt   20340
tgacccctac tttgtctatt ctggttctat tccctacctg gatggtacct tctacctgaa   20400
ccacactttt aagaaggttt ccatcatgtt tgactcttca gtgagctggc ctggaaatga   20460
caggttacta tctcctaacg aatttgaaat aaagcgcact gtggatggcg aaggctacaa   20520
cgtagcccaa tgcaacatga ccaaagactg gttcttggta cagatgctcg ccaactacaa   20580
catcggctat cagggcttct acattccaga aggatacaaa gatcgcatgt attcattttt   20640
cagaaacttc cagcccatga gcaggcaggt ggttgatgag gtcaattaca agacttcaa    20700
ggccgtcgcc atacgctacc aacacaacaa ctctggcttt gtgggttaca tggctccgac   20760
catgcgccaa ggtcaaccct atcccgctaa ctatccctat ccactcattg gaacaactgc   20820
cgtaaatagt gttacgcaga aaagttctt gtgtgacaga accatgtggc gcataccgtt    20880
ctcgagcaac ttcatgtcta tgggggccct tacagacttg ggacagaata tgctctatgc   20940
caactcagct catgctctgg acatgacctt tgaggtggat cccatggatg agcccaccct   21000
gctttatctt ctcttcgaag ttttcgacgt ggtcagagtg catcagccac accgcggcat   21060
catcgaggca gtctacctgc gtacaccgtt ctcggccggt aacgctacca cgtaagaagc   21120
ttcttgcttc ttgcaaatag cagctgcaac catggcctgc ggatcccaaa acggctccag   21180
cgagcaagag ctcagagcca ttgtccaaga cctgggttgc ggaccctatt ttttgggaac   21240
ctacgataag cgcttcccgg ggttcatggc ccccgataag ctcgcctgtg ccattgtaaa   21300
tacggccgga cgtgagacgg ggggagagca ctggttggct ttcggttgga acccacgttc   21360
taacacctgc tacctttttg atcctttggg attctcggat gatcgtctca acagatttta   21420
ccagtttgaa tatgagggtc tcctgcgccg cagcgctctt gctaccaagg accgctgtat   21480
tacgctggaa aaatctaccc agaccgtgca gggccccgt tctgccgcct gcggactttt    21540
ctgctgcatg ttccttcacg cctttgtgca ctggcctgac cgtcccatgg acggaaaccc   21600
caccatgaaa ttgctaactg gagtgccaaa caacatgctt cattctccta agtccagcc    21660
caccctgtgt gacaatcaaa aagcactcta ccatttttctt aatacccatt cgccttattt   21720
```

-continued

```
tcgctctcat cgtacacaca tcgaaagggc cactgcgttc gaccgtatgg atgttcaata    21780
atgactcatg taaacaacgt gttcaataaa catcacttta ttttttttaca tgtatcaagg    21840 ctctggatta cttatttatt tacaagtcga atgggttctg acgagaatca gaatgacccg    21900
caggcagtga tacgttgcgg aactgatact tgggttgcca cttgaattcg ggaatcacca    21960
acttgggaac cggtatatcg ggcaggatgt cactccacag ctttctggtc agctgcaaag    22020
ctccaagcag gtcaggagcc gaaatcttga aatcacaatt aggaccagtg ctctgagcgc    22080
gagagttgcg gtacaccgga ttgcagcact gaaacaccat cagcgacgga tgtctcacgc    22140
ttgccagcac ggtgggatct gcaatcatgc ccacatccag atcttcagca ttggcaatgc    22200
tgaacggggt catcttgcag gtctgcctac ccatggcggg cacccaatta ggcttgtggt    22260
tgcaatcgca gtgcagggg atcagtatca tcttggcctg atcctgtctg attcctggat    22320
acacggctct catgaaagca tcatattgct tgaaagcctg ctgggcttta ctaccctcgg    22380
tataaaacat cccgcaggac ctgctcgaaa actggttagc tgcacagccg gcatcattca    22440
cacagcagcg ggcgtcattg ttggctattt gcaccacact tctgccccag cggttttggg    22500 tgatttggt tcgctcggga ttctcctta aggctcgttg tccgttctcg ctggccacat    22560
ccatctcgat aatctgctcc ttctgaatca taatattgcc atgcaggcac ttcagcttgc    22620
cctcataatc attgcagcca tgaggccaca acgcacagcc tgtacattcc caattatggt    22680
gggcgatctg agaaaaagaa tgtatcattc cctgcagaaa tcttcccatc atcgtgctca    22740
gtgtcttgtg actagtgaaa gttaactgga tgcctcggtg ctcttcgttt acgtactggt    22800
gacagatgcg cttgtattgt tcgtgttgct caggcattag tttaaaacag gttctaagtt    22860
cgttatccag cctgtacttc tccatcagca gacacatcac ttccatgcct ttctcccaag    22920
cagacaccag gggcaagcta atcggattct taacagtgca ggcagcagct cctttagcca    22980
gagggtcatc tttagcgatc ttctcaatgc ttcttttgcc atccttctca acgatgcgca    23040
cgggcgggta gctgaaaccc actgctacaa gttgcgcctc ttctcttct tcttcgctgt    23100 cttgactgat gtcttgcatg gggatatgtt tggtcttcct tggcttcttt ttgggggta    23160 tcggaggagg aggactgtcg ctccgttccg gagacaggga ggattgtgac gtttcgctca    23220
ccattaccaa ctgactgtcg gtagaagaac ctgacccccac acggcgacag gtgttttct    23280 tcggggcag aggtggaggc gattgcgaag ggctgcggtc cgacctggaa ggcggatgac    23340
tggcagaacc ccttccgcgt tcgggggtgt gctccctgtg gcggtcgctt aactgatttc    23400
cttcgcggct ggccattgtg ttctcctagg cagagaaaca acagacatgg aaactcagcc    23460
attgctgtca acatcgccac gagtgccatc acatctcgtc ctcagcgacg aggaaaagga    23520
gcagagctta agcattccac cgcccagtcc tgccaccacc tctaccctag aagataagga    23580
ggtcgacgca tctcatgaca tgcagaataa aaaagcgaaa gagtctgaga cagacatcga    23640
gcaagacccg ggctatgtga caccggtgga acacgaggaa gagttgaaac gctttctaga    23700
gagagaggat gaaaactgcc caaaacagcg agcagataac tatcaccaag atgctggaaa    23760
tagggatcag aacaccgact acctcatagg gcttgacggg gaagacgcgc tccttaaaca    23820
tctagcaaga cagtcgctca tagtcaagga tgcattattg gacagaactg aagtgcccat    23880
cagtgtggaa gagctcagct gcgcctacga gcttaacctt ttttcacctc gtactcccccc    23940 caaacgtcag ccaaacggca cctgcgagcc aaatcctcgc ttaaactttt atccagcttt    24000
tgctgtgcca gaagtactgg ctacctatca catcttttt aaaaatcaaa aaattccagt    24060
```

-continued

```
ctcctgccgc gctaatcgca cccgcgccga tgccctactc aatctgggac ctggttcacg    24120
cttacctgat atagcttcct tggaagaggt tccaaagatc ttcgagggtc tgggcaataa    24180
tgagactcgg gccgcaaatg ctctgcaaaa gggagaaaat ggcatggatg agcatcacag    24240
cgttctggtg gaattggaag gcgataatgc cagactcgca gtactcaagc gaagcgtcga    24300
ggtcacacac ttcgcatatc ccgctgtcaa cctgccccct aaagtcatga cggcggtcat    24360
ggaccagtta ctcattaagc gcgcaagtcc cctttcagaa gacatgcatg acccagatgc    24420
ctgtgatgag ggtaaaccag tggtcagtga tgagcagcta acccgatggc tgggcaccga    24480
ctctccccgg gatttggaag agcgtcgcaa gcttatgatg gccgtggtgc tggttaccgt    24540
agaactagag tgtctccgac gtttctttac cgattcagaa accttgcgca aactcgaaga    24600
gaatctgcac tacactttta gacacggctt tgtgcggcag gcatgcaaga tatctaacgt    24660
ggaactcacc aacctggttt cctacatggg tattctgcat gagaatcgcc taggacaaag    24720
cgtgctgcac agcaccctta aggggaagc cgccgtgat tacatccgcg attgtgtcta    24780
tctctacctg tgccacacgt ggcaaaccgg catgggtgta tggcagcaat gtttagaaga    24840
acagaacttg aaagagcttg acaagctctt acagaaatct cttaaggttc tgtggacagg    24900
gttcgacgag cgcaccgtcg cttccgacct ggcagacctc atcttcccag agcgtctcag    24960
ggttactttg cgaaacggat tgcctgactt tatgagccaa agcatgctta acaattttcg    25020
ctctttcatc ctggaacgct ccggtatcct gcccgccacc tgctgcgcac tgccctccga    25080
ctttgtgcct ctcacctacc gcgagtgccc ccgccgcta tggagtcact gctacctgtt    25140
ccgtctggcc aactatctct cctaccactc ggatgtgatc gaggatgtga gcggagacgg    25200
cttgctggag tgccactgcc gctgcaatct gtgcacgccc caccggtccc tagcttgcaa    25260
cccccagttg atgagcgaaa cccagataat aggcacctt gaattgcaag gccccagcag    25320
ccaaggcgat gggtcttctc ctgggcaaag ttttaaaactg accccgggac tgtggaccct    25380
cgcctacttg cgcaagtttg ctccggaaga ttaccacccc tatgaaatca gttctatga    25440
ggaccaatca cagcctccaa aggccgaact ttcggcttgc gtcatcaccc agggggcaat    25500
tctggcccaa ttgcaagcca tccaaaaatc ccgccaagaa tttctactga aaaagggtaa    25560
gggggtctac cttgaccccc agaccggcga ggaactcaac acaagttcc ctcaggatgt    25620
cccaacgacg agaaaacaag aagttgaagg tgcagccgcc gcccccagaa gatatggagg    25680
aagattggga cagtcaggca gaggaggcgg aggaggacga tctggaggac agtctggagg    25740
aagacagttt ggaggaggaa acgaggagg cagaggaggt ggaagaagta accgccgaca    25800
aacagttatc ctcggctgcg gagacaagca acagcgctac catctccgct ccgagtcgag    25860
gaacccggcg gcgtcccagc agtagatggg acgagaccgg acgcttccg aacccaacca    25920
gcgcttccaa gaccggtaag aaggatcggc agggatacaa gtcctggcgg gggcataaga    25980
atgccatcat ctcctgcttg catgagtgcg ggggcaacat atccttcacg cggcgctact    26040
tgctattcca ccatgggtg aactttccgc gcaatgtttt gcattactac cgtcacctcc    26100
acagcccta ctatagccag caaatcccga cagtctcgac agataaagac agcggcggcg    26160
acctccaaca gaaaaccagc agcggcagtt agaaaatca caacagtgc agcaacagga    26220
ggattaaaga ttacagccaa cgagccagcg caaacccgag agttaagaaa tcggatcttt    26280
ccaaccctgt atgccatctt ccagcagagt cggggtcaag agcaggaact gaaaataaaa    26340
aaccgatctc tgcgttcgct caccagaagt tgtttgtatc acaagagcga agatcaactt    26400
cagcgcactc tcgaggacgc cgaggctctc ttcaacaagt actgcgcgct gactcttaaa    26460
```

-continued

```
gagtaggcag cgaccgcgct tattcaaaaa aggcgggaat tacatcatcc tcgacatgag   26520
taaagaaatt cccacgcctt acatgtggag ttatcaaccc caaatgggat tggcagcagg   26580
cgcctcccag gactactcca cccgcatgaa ttggctcagc gccgggcctt ctatgatttc   26640
tcgagttaat gatatacgcg cctaccgaaa ccaaatactt ttggaacagt cagctcttac   26700
caccacgccc cgccaacacc ttaatcccag aaattggccc gccgcctag tgtaccagga   26760 aagtcccgct cccaccactg tattacttcc tcgagacgcc caggccgaag tccaaatgac   26820
taatgcaggt gcgcagttag ctggcggctc caccctatgt cgtcacaggc ctcggcataa   26880
tataaaacgc ctgatgatca gaggccgagg tatccagctc aacgacgagt cggtgagctc   26940
tccgcttggt ctacgaccag acggaatctt tcagattgcc ggctgcggga gatcttcctt   27000 caccctcgt caggctgttc tgactttgga agttcgtct tcgcaacccc gctcgggcgg   27060
aatcgggacc gttcaatttg tagaggagtt tactccctct gtctacttca accccttctc   27120
cggatctcct gggcactacc cggacgagtt cataccgaac ttcgacgcga ttagcgagtc   27180
agtggacggc tacgattgat gtctggtgac gcggctgagc tatctcggct gcgacatcta   27240
gaccactgcc gccgctttcg ctgctttgcc cgggaactta ttgagttcat ctacttcgaa   27300
ctccccaagg atcaccctca aggtccggcc cacggagtgc ggattactat cgaaggcaaa   27360
atagactctc gcctgcaacg aattttctcc cagcggcccg tgctgatcga gcgagaccag   27420
ggaaacacca cggtttccat ctactgcatt tgtaatcacc ccggattgca tgaaagcctt   27480
tgctgtctta tgtgtactga gtttaataaa aactgaatta agactctcct acggactgcc   27540
gcttcttcaa cccggattt acaaccagaa gaacaaaact tttcctgtcg tccaggactc   27600
tgttaacttc acctttccta ctcacaaact agaagctcaa cgactacacc gcttttccag   27660
aagcattttc cctactaata ctactttcaa accggaggt gagctccacg gtctccctac   27720
agaaaaccct tgggtggaag cgggccttgt agtactagga attcttgcgg gtgggcttgt   27780
gattattctt tgctacctat acacaccttg cttcactttc ctagtggtgt tgtggtattg   27840
gtttaaaaaa tggggcccat actagtcttg cttgttttac tttcgctttt ggaaccgggt   27900
tctgccaatt acgatccatg tctagacttt gacccagaaa actgcacact tacttttgca   27960
cccgacacaa gccgcatctg tggagttctt attaagtgcg gatgggaatg caggtccgtt   28020
gaaattacac acaataacaa aacctggaac aataccttat ccaccacatg ggagccagga   28080
gttcccgagt ggtacactgt ctctgtccga ggtcctgacg gttccatccg cattagtaac   28140
aacactttca ttttttctga aatgtgcgat ctggccatgt tcatgagcaa acagtattct   28200
ctatggcctc ctagcaagga caacatcgta acgttctcca ttgcttattg cttgtgcgct   28260
tgccttctta ctgctttact gtgcgtatgc atacacctgc ttgtaaccac tcgcatcaaa   28320
aacgccaata acaaagaaaa aatgccttaa cctctttctg tttacagaca tggcttctct   28380
tacatctctc atatttgtca gcattgtcac tgccgctcac ggacaaacag tcgtctctat   28440
cccactagga cataattaca ctctcatagg acccccaatc acttcagagg tcatctggac   28500
caaactggga agcgttgatt actttgatat aatctgtaac aaaacaaaac caataatagt   28560
aacttgcaac atacaaaatc ttacattgat taatgttagc aaagtttaca gcggttacta   28620
ttatggttat gacagataca gtagtcaata tagaaattac ttggttcgtg ttacccagtt   28680
gaaaaccacg aaaatgccaa atatggcaaa gattcgatcc gatgacaatt ctctagaaac   28740
ttttacatct cccaccacac ccgacgaaaa aaacatccca gattcaatga ttgcaattgt   28800
```

-continued

```
tgcagcggtg gcagtggtga tggcactaat aataatatgc atgcttttat atgcttgtcg    28860
ctacaaaaag tttcatccta aaaacaaga tctcctacta aggcttaaca tttaatttct     28920
ttttatacag ccatggtttc cactaccaca ttccttatgc ttactagtct cgcaactctg    28980
acttctgctc gctcacacct cactgtaact ataggctcaa actgcacact aaaaggacct    29040
caaggtggtc atgtcttttg gtggagaata tatgacaatg gatggtttac aaaaccatgt    29100
gaccaacctg gtagatttt ctgcaacggc agagacctaa ccattatcaa cgtgacagca    29160
aatgacaaag gcttctatta tggaaccgac tataaaagta gtttagatta taacattatt   29220
gtactgccat ctaccactcc agcaccccgc acaactactt tctctagcag cagtgtcgct    29280
aacaatacaa tttccaatcc aacctttgcc gcgcttttaa aacgcactgt gaataattct    29340
acaacttcac atacaacaat ttccacttca acaatcagca tcatcgctgc agtgacaatt    29400
ggaatatcta ttcttgtttt taccataacc tactacgcct gctgctatag aaaagacaaa    29460
cataaaggtg atccattact tagatttgat atttaatttg ttcttttttt ttatttacag   29520
tatggtgaac accaatcatg gtacctagaa atttcttctt caccatactc atctgtgctt    29580
ttaatgtttg cgctactttc acagcagtag ccacagcaac cccagactgt ataggagcat    29640
ttgcttccta tgcactttt gcttttgtta cttgcatctg cgtatgtagc atagtctgcc    29700
tggttattaa tttttccaa cttctagact ggatccttgt gcgaattgcc tacctgcgcc    29760
accatcccga ataccgcaac caaaatatcg cggcacttct tagactcatc taaaaccatg    29820
caggctatac taccaatatt tttgcttcta ttgcttccct acgctgtctc aaccccagct    29880
gcctatagta ctccaccaga acaccttaga aaatgcaaat tccaacaacc gtggtcattt    29940
cttgcttgct atcgagaaaa atcagaaatc ccccaaatt taataatgat tgctggaata    30000
attaatataa tctgttgcac cataatttca tttttgatat accccctatt tgattttggc    30060
tggaatgctc ccaatgcaca tgatcatcca caagacccag aggaacacat tcccccacaa    30120
aacatgcaac atccaatagc gctaatagat tacgaaagtg aaccacaacc cccactactc    30180
cctgctatta gttacttcaa cctaaccggc ggagatgact gaaacactca ccacctccaa    30240
ttccgccgag gatctgctcg atatggacgg ccgcgtctca gaacaacgac ttgcccaact    30300
acgcatccgc cagcagcagg aacgcgtggc caaagagctc agagatgtca tccaaattca    30360
ccaatgcaaa aaaggcatat tctgtttggt aaaacaagcc aagatatcct acgagatcac    30420
cgctactgac catcgcctct cttacgaact tggcccccaa cgacaaaaat ttacctgcat    30480
ggtgggaatc aaccccatag ttatcaccca acaaagtgga gatactaagg gttgcattca    30540
ctgctcctgc gattccatcg agtgcaccta caccctgctg aagacccctat gcggcctaag    30600
agacctgcta ccaatgaatt aaaaaaaat gattaataaa aaatcactta cttgaaatca    30660
gcaataaggt ctctgttgaa atttttctccc agcagcacct cacttccctc ttcccaactc   30720
tggtattcta aaccccgttc agcggcatac tttctccata ctttaaaggg gatgtcaaat    30780
tttagctcct ctcctgtacc cacaatcttc atgtctttct tcccagatga ccaagagagt    30840
ccggctcagt gactccttca accctgtcta cccctatgaa gatgaaagca cctcccaaca    30900
cccctttata aacccagggt ttatttcccc aaatggcttc acacaaagcc cagacggagt   30960
tcttacttta aaatgtttaa ccccactaac aaccacaggc ggatctctac agctaaaagt    31020
gggaggggga cttacagtgg atgacactga tggtacctta caagaaaaca tacgtgctac    31080
agcacccatt actaaaaata atcactctgt agaactatcc attggaaatg gattagaaac    31140
tcaaaacaat aaactatgtg ccaaattggg aaatgggtta aaatttaaca acggtgacat    31200
```

```
ttgtataaag gatagtatta acaccttatg gactggaata aaccctccac ctaactgtca      31260
aattgtggaa acactaata caaatgatgg caaacttact ttagtattag taaaaaatgg      31320
agggcttgtt aatggctacg tgtctctagt tggtgtatca gacactgtga accaaatgtt      31380
cacacaaaag acagcaaaca tccaattaag attatatttt gactcttctg gaaatctatt      31440
aactgaggaa tcagacttaa aaattccact taaaaataaa tcttctacag cgaccagtga      31500
aactgtagcc agcagcaaag cctttatgcc aagtactaca gcttatccct tcaacaccac      31560
tactagggat agtgaaaact acattcatgg aatatgttac tacatgacta gttatgatag      31620
aagtctattt cccttgaaca tttctataat gctaaacagc cgtatgattt cttccaatgt      31680
tgcctatgcc atacaatttg aatggaatct aaatgcaagt gaatctccag aaagcaacat      31740
agctacgctg accacatccc ccttttttctt ttcttacatt acagaagacg acaactaaaa      31800
taaagtttaa gtgtttttat ttaaaatcac aaaattcgag tagttatttt gcctccacct      31860
tcccatttga cagaatacac caatctctcc ccacgcacag ctttaaacat ttggatacca      31920
ttagagatag acattgtttt agattccaca ttccaaacag tttcagagcg agccaatctg      31980
gggtcagtga tagataaaaa tccatcgcga tagtctttta aagcgctttc acagtccaac      32040
tgctgcggat gcgactccgg agtttggatc acggtcatct ggaagaagaa cgatgggaat      32100
cataatccga aaacggtatc ggacgattgt gtctcatcaa acccacaagc agccgctgtc      32160
tgcgtcgctc cgtgcgactg ctgtttatgg gatcagggtc cacagtttcc tgaagcatga      32220
ttttaatagc ccttaacatc aactttctgg tgcgatgcgc gcagcaacgc attctgattt      32280
cactcaaatc tttgcagtag gtacaacaca ttattacaat attgtttaat aaaccataat      32340
taaaagcgct ccagccaaaa ctcatatctg atataatcgc ccctgcatga ccatcatacc      32400
aaagtttaat ataattaaa tgacgttccc tcaaaaacac actacccaca tacatgatct      32460
cttttggcat gtgcatatta acaatctgtc tgtaccatgg acaacgttgg ttaatcatgc      32520
aacccaatat aaccttccgg aaccacactg ccaacaccgc tcccccagcc atgcattgaa      32580
gtgaaccctg ctgattacaa tgacaatgaa gaacccaatt ctctcgaccg tgaatcactt      32640
gagaatgaaa aatatctata gtggcacaac atagacataa atgcatgcat cttctcataa      32700
tttttaactc ctcaggattt agaaacatat cccagggaat aggaagctct tgcagaacag      32760
taaagctggc agaacaagga agaccacgaa cacaacttac actatgcata gtcatagtat      32820
cacaatctgg caacagcggg tggtcttcag tcatagaagc tcgggtttca ttttcctcac      32880
aacgtggtaa ctgggctctg tgtaagggt gatgtctggc gcatgatgtc gagcgtgcgc      32940
gcaaccttgt cataatggag ttgcttcctg acattctcgt attttgtata gcaaaacgcg      33000
gccctggcag aacacactct tcttcgcctt ctatcctgcc gcttagcgtg ttccgtgtga      33060
tagttcaagt acagccacac tcttaagttg gtcaaaagaa tgctggcttc agttgtaatc      33120
aaaactccat cgcatctaat tgttctgagg aaatcatcca cggtagcata tgcaaatccc      33180
aaccaagcaa tgcaactgga ttgcgtttca agcaggagag gagagggaag agacggaaga      33240
accatgttaa tttttattcc aaacgatctc gcagtacttc aaattgtaga tcgcgcagat      33300
ggcatctctc gccccactg tgttggtgaa aaagcacagc taaatcaaaa gaaatgcgat      33360
tttcaaggtg ctcaacggtg gcttccaaca aagcctccac gcgcacatcc aagaacaaaa      33420
gaataccaaa agaaggagca ttttctaact cctcaatcat catattacat tcctgcacca      33480
ttcccagata attttcagct ttccagcctt gaattattcg tgtcagttct tgtggtaaat      33540
```

-continued

```
ccaatccaca cattacaaac aggtcccgga gggcgccctc caccaccatt cttaaacaca  33600
ccctcataat gacaaaatat cttgctcctg tgtcacctgt agcgaattga gaatggcaac  33660
atcaattgac atgcccttgg ctctaagttc ttctttaagt tctagttgta aaaactctct  33720
catattatca ccaaactgct tagccagaag ccccccggga acaagagcag gggacgctac  33780
agtgcagtac aagcgcagac ctccccaatt ggctccagca aaaacaagat tggaataagc  33840
atattgggaa ccaccagtaa tatcatcgaa gttgctggaa atataatcag gcagagtttc  33900
ttgtagaaat tgaataaaag aaaaatttgc caaaaaaaca ttcaaaacct ctgggatgca  33960
aatgcaatag gttaccgcgc tgcgctccaa cattgttagt tttgaattag tctgcaaaaa  34020
taaaaaaaaa acaagcgtca tatcatagta gcctgacgaa caggtggata aatcagtctt  34080
tccatcacaa gacaagccac agggtctcca gctcgaccct cgtaaaacct gtcatcgtga  34140
ttaaacaaca gcaccgaaag ttcctcgcgg tgaccagcat gaataagtct tgatgaagca  34200
tacaatccag acatgttagc atcagttaag gagaaaaaac agccaacata gcctttgggt  34260
ataattatgc ttaatcgtaa gtatagcaaa gccacccctc gcggatacaa agtaaaaggc  34320
acaggagaat aaaaaatata attatttctc tgctgctgtt taggcaacgt cgcccccggt  34380
ccctctaaat acacatacaa agcctcatca gccatggctt accagagaaa gtacagcggg  34440
cacacaaacc acaagctcta aagtcactct ccaacctstc cacaatatat atacacaagc  34500
cctaaactga cgtaatggga ctaaagtgta aaaaatcccg ccaaacccaa cacacacccc  34560
gaaactgcgt caccagggaa aagtacagtt tcacttccgc aatcccaaca agcgtcactt  34620
cctctttctc acggtacgtc acatcccatt aacttacaac gtcattttcc cacggccgcg  34680
ccgccccttt taaccgttaa ccccacagcc aatcaccaca cggcccacac tttttaaaat  34740
cacctcattt acatattggc accattccat ctataaggta tattattgat gatg         34794
```

COMPLEMENTING CELL LINES

CROSS-REFERENCE TO RELATED APPLICATIONS

This application is a continuation-in-part of application Ser. No. 09/573,740, filed May 18, 2000, pending, which claims the benefit of the filing date of U.S. Provisional Application Serial No. 60/134,764 filed May 18, 1999.

TECHNICAL FIELD

The invention relates to the field of biotechnology generally, and more specifically to adenoviral-based complementing cell lines.

BACKGROUND

Typically, vector and packaging cells have to be adapted to one another so that they have all the necessary elements, but they do not have overlapping elements which lead to replication competent virus by recombination. Therefore, the sequences necessary for proper transcription of the packaging construct may be heterologous regulatory sequences derived from, for example, other human adenovirus (Ad) serotypes, non-human adenoviruses, other viruses like, but not limited to, SV40, hepatitis B virus (HBV), Rous Sarcoma Virus (RSV), cytomegalo virus (CMV), etc. or from higher eukaryotes such as mammals. In general, these sequences include a promoter, enhancer and polyadenylation sequences.

PER.C6 (ECACC deposit number 96022940) is an example of a cell line devoid of sequence overlap between the packaging construct and the adenoviral vector (Fallaux et al., 1998). Recombinant viruses based on subgroup C adenoviruses such as Ad5 and Ad2 can be propagated efficiently on these packaging cells. Generation and propagation of adenoviruses from other serotypes, like subgroup B viruses, has proven to be more difficult on PER.C6 cells. However, as described in European patent application 00201738.2, recombinant viruses based on subgroup B virus Ad35 can be made by co-transfection of an expression construct containing the Ad35 early region-1 sequences (Ad35-E1). Furthermore, Ad35-based viruses that are deleted for E1A sequences were shown to replicate efficiently on PER.C6 cells. Thus, the E1A proteins of Ad5 complement Ad35-E1A functions, whereas at least part of the E1B functions of Ad35 are necessary. This serotype specificity in E1B functions was recently also described for Ad7 recombinant viruses. In an attempt to generate recombinant adenoviruses derived from subgroup B virus Ad7, Abrahamsen et al. (1997) were not able to generate E1-deleted viruses on 293 cells without contamination of wild-type (wt) Ad7. Viruses that were picked after plaque purification on 293-ORF6 cells (Brough et al., 1996) were shown to have incorporated Ad7 E1B sequences by non-homologous recombination. Thus, efficient propagation of Ad7 recombinant viruses proved possible only in the presence of Ad7-E1B expression and Ad5-E4-ORF6 expression. The E1B proteins are known to interact with cellular as well as viral proteins (Bridge et al., 1993; White, 1995). Possibly, the complex formed between the E1B 55K protein and E4-ORF6 which is necessary to increase MRNA export of viral proteins and to inhibit export of most cellular mRNAs, is critical and in some way serotype specific.

DESCRIPTION OF THE INVENTION

The present invention provides new packaging cell lines capable of complementing recombinant adenoviruses based on serotypes other than subgroup C viruses, such as serotypes from subgroup B, like adenovirus type 35.

In one aspect of the invention, the new packaging cells are derived from primary, diploid human cells such as, but not limited to, primary human retinoblasts, primary human embryonic kidney cells or primary human amniocytes. Transfection of primary cells with the adenovirus E1A gene alone can induce unlimited proliferation (immortalisation), but does not result in complete transformation. However, expression of E1A in most cases results in induction of programmed cell death (apoptosis), and occasionally immortalisation is obtained (Jochemsen et al., 1987). Co-expression of the E1B gene is required to prevent induction of apoptosis and for complete morphological transformation to occur (reviewed in White, 1995). Therefore, in one aspect of the invention, primary human cells are transformed by expression of adenovirus E1 proteins of a subgroup other than subgroup C, preferably subgroup B, more preferably adenovirus type 35. The combined activity of the E1A and E1B proteins establishes indefinite growth of the cells and enables complementation of recombinant adenoviruses.

In another aspect of the invention, the transforming E1 sequences are derived from different serotypes. As disclosed in European Patent application 00201738.2, Ad35 E1 sequences are capable of transforming Baby Rat Kidney (BRK) cells, albeit with a lower efficiency than that seen with Ad5 E1 sequences. This was also observed for E1 sequences from Ad12 (Bernards et al., 1982). Therefore, in this aspect of the invention, primary diploid human cells are transformed with chimeric E1 constructs that consist of part of the E1 sequences of a serotype that enables efficient transformation of primary human cells and part of the E1 sequences of another serotype which E1 sequences provide the serotype-specific E1B function(s) that enable(s) efficient propagation of E1-deleted viruses of that serotype. In a preferred embodiment of this aspect of the invention, the E1A region is derived from a subgroup C adenovirus, like, but not limited to, Ad5, and the E1B sequences are derived from an alternative adenovirus more particularly from an adenovirus of subgroup B, more particularly from adenovirus type 35. In a more preferred embodiment, the E1A sequences and the E1B-21K sequences are derived from a subgroup C adenovirus, like, but not limited to, Ad5, and the E1B-55k sequences as far as not overlapping with the 21K sequences are derived from an adenovirus of subgroup B, more particular from adenovirus type 35. In an even more preferred embodiment, all E1 sequences are derived from a subgroup C adenovirus, like but not limited to Ad5, except for at least the part of the E1B-55K sequences that are necessary for serotype-specific complementation of an alternative adenovirus subgroup, more particular adenovirus subgroup B, more particular adenovirus type 35, the sequences being derived from the adenovirus.

The primary diploid human cells are transformed by adenovirus E1 sequences either operatively linked on one DNA molecule or located on two separate DNA molecules. In the latter case, one DNA molecule carries at least part of the E1 sequences of the serotype enabling efficient transformation and the second DNA molecule carries at least part of the sequences necessary for serotype-specific complementation. In all aspects, the sequences are operatively linked to regulatory sequences enabling transcription and translation of the encoded proteins.

In another aspect of the invention, new packaging cells are described that are derived from PER.C6 (ECACC deposit number 96022940; Fallaux et al., 1998) and contain Ad35-E1 sequences integrated into their genome. These Ad35-E1 sequences are present in a functional expression cassette, but preferably do not contain sequences overlapping with sequences present in the recombinant viral vector. Preferably, the functional expression cassette consists of a heterologous promoter and poly-adenylation signal functionally linked to Ad35-E1 sequences. More specifically, the Ad35-E1 sequences are functionally linked to the human phosphoglycerate gene promoter (hPGK) and hepatitis B virus poly-adenylation signal (HBV-pA). Preferably, Ad35-E1 sequences comprise the coding regions of the E1A proteins and the E1B promoter sequences linked to E1B coding sequences up to and including the stop codon of the E1B 55K protein. More preferably, the Ad35-E1 sequences comprise nucleotide 468 to nucleotide 3400 of the Ad35 wt sequence. To be able to select for transfected cells, a dominant selection marker like, but not limited to, the neor gene has to be incorporated on the expression vector or the Ad35 expression vector is co-transfected with a separate expression vector mediating expression of the selection marker. In both cases, the selection marker becomes integrated in the cellular genome. Other AdS-E1 transformed cell lines like 293 (Graham et al., 1977) and 911 (Fallaux et al., 1996) or established human cell lines like A549 cells may be used without departing from the present invention.

In another aspect of the invention, PER.C6-derived cells are described that express functional Ad35 E1B sequences. In one embodiment, the Ad35-E1B sequences are driven by the E1B promoter and terminated by a heterologous poly-adenylation signal like, but not limited to, the HBVpA. In a preferred embodiment, the Ad35-E1B sequences are driven by a heterologous promoter like, but not limited to, the hPGK promoter or Elongation Factor-1α (EF-1α) promoter and terminated by a heterologous pA signal like, but not limited to, the HBVpA. These Ad35-E1B sequences preferably comprise the coding regions of the E1B 21K and the E1B 55K proteins located between nucleotides 1611 and 3400 of the wild-type (wt) Ad35 sequence. More preferably, the Ad35-E1B sequences comprise nucleotides 1550 to 3400 of the wt Ad35 sequence. In an even more preferred embodiment, the E1B sequences comprise the coding sequences of the E1B-55K gene located between nucleotides 1916 and 3400 of the wt Ad35 sequence.

Cell lines subject of this invention are useful for, among other things, the production of recombinant adenoviruses designed for gene therapy and vaccination. The cell lines, being derived from cells of human origin, are also useful for the production of human recombinant therapeutic proteins like, but not limited to human growth factors, human antibodies. In addition the cell lines are useful for the production of human viruses other than adenovirus like, but not limited to, influenza virus, herpes simplex virus, rotavirus, measles virus.

BRIEF DESCRIPTION OF THE FIGURES

FIG. 3: Bar graph presenting the percentage sera samples that show neutralizing activity to a selection of adenovirus serotypes. Sera were derived from healthy volunteers from Belgium and the UK.

FIG. 4: Bar graph presenting the percentage sera samples that show neutralizing activity to adenovirus serotypes 5, 11, 26, 34, 35, 48 and 49. Sera were derived from five different locations in Europe and the United States.

FIG. 5: Sequence of human adenovirus type 35.

DETAILED DESCRIPTION OF THE INVENTION

Figure 1:
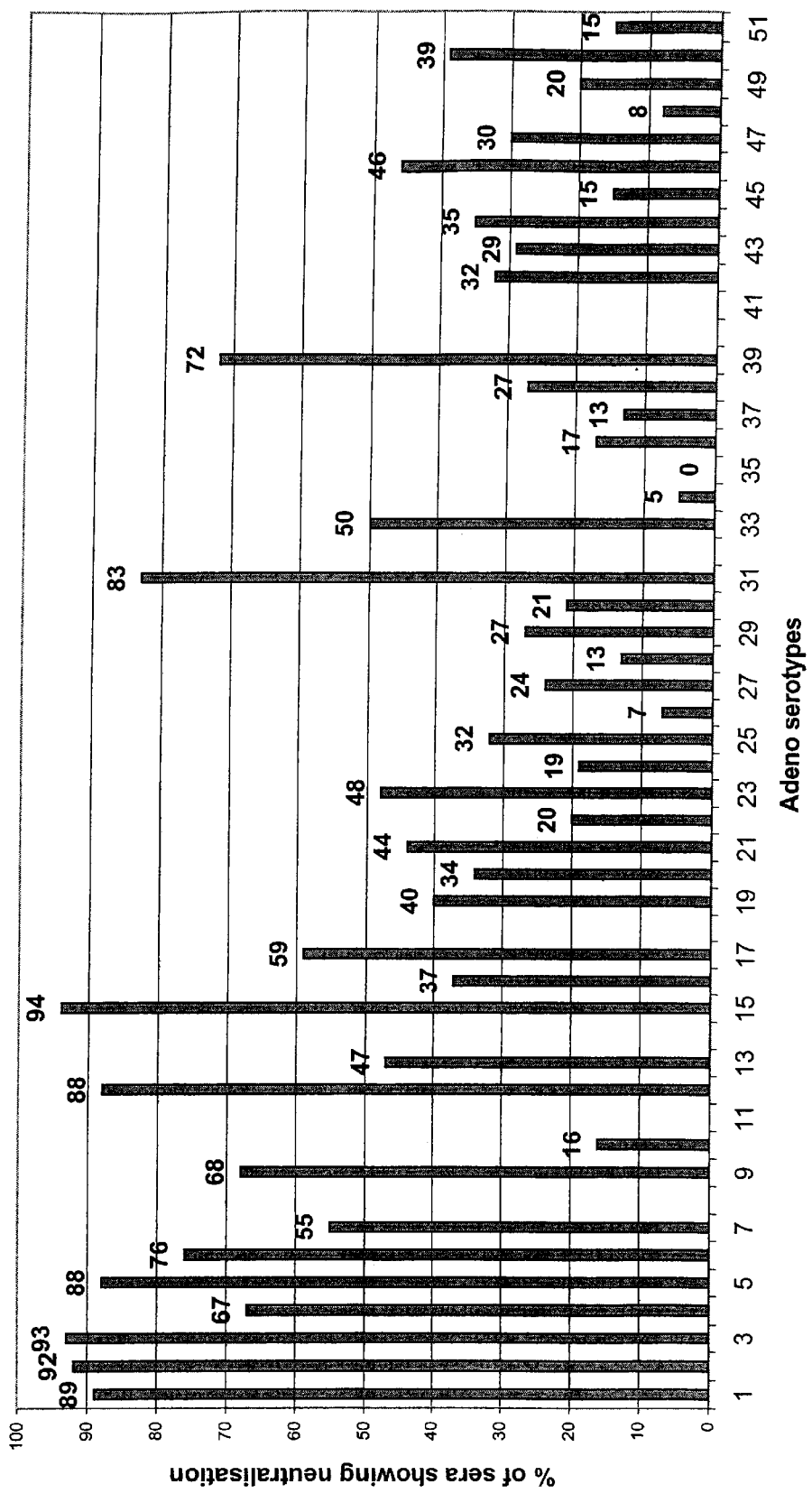
FIG. 1: Bar graph showing the percentage of serum samples positive for neutralization for each human wt adenovirus tested (see, Example for description of the neutralization assay).

The invention is further explained by the use of the following illustrative examples.

EXAMPLES

Example 1

A High Throughput Assay for the Detection of Neutralizing Activity in Human Serum To enable screening of a large amount of human sera for the presence of neutralizing antibodies against all adenovirus serotypes, an automated 96-wells assay was developed.

Human Sera

A panel of 100 individuals was selected. Volunteers (50% male, 50% female) were healthy individuals between ages 20 and 60 years old with no restriction for race. All volunteers signed an informed consent form. People professionally involved in adenovirus research were excluded.

Approximately 60 ml blood was drawn in dry tubes. Within two hours after sampling, the blood was centrifuged at 2500 rpm for 10 minutes. Approximately 30 ml serum was transferred to polypropylene tubes and stored frozen at −20° C. until further Serum was thawed and heat-inactivated at 56° C. for 10 minutes and then aliquoted to prevent repeated cycles of freeze/thawing. Part was used to make five steps of twofold dilutions in medium (DMEM, Gibco BRL) in a quantity enough to fill out approximately 70 96-well plates. Aliquots of undiluted and diluted sera were pipetted in deep well plates (96-well format) and using a programmed platemate dispensed in 100 µl aliquots into 96-well plates. This way the plates were loaded with eight different sera in (100 µl/well) according to the scheme below:

| S1/2 | S1/4 | S1/8 | S1/16 | S1/32 | S5/2 | S5/4 | S5/8 | S5/16 | S5/32 | — | — |
|------|------|------|-------|-------|------|------|------|-------|-------|---|---|
| S1/2 | S1/4 | S1/8 | S1/16 | S1/32 | S5/2 | S5/4 | S5/8 | S5/16 | S5/32 | — | — |
| S2/2 | S2/4 | S2/8 | S2/16 | S2/32 | S6/2 | S6/4 | S6/8 | S6/16 | S6/32 | — | — |
| S2/2 | S2/4 | S2/8 | S2/16 | S2/32 | S6/2 | S6/4 | S6/8 | S6/16 | S6/32 | — | — |
| S3/2 | S3/4 | S3/8 | S3/16 | S3/32 | S7/2 | S7/4 | S7/8 | S7/16 | S7/32 | — | — |
| S3/2 | S3/4 | S3/8 | S3/16 | S3/32 | S7/2 | S7/4 | S7/8 | S7/16 | S7/32 | — | — |
| S4/2 | S4/4 | S3/8 | S3/16 | S3/32 | S8/2 | S8/4 | S8/8 | S8/16 | S8/32 | — | — |
| S4/2 | S4/4 | S3/8 | S3/16 | S3/32 | S8/2 | S8/4 | S8/8 | S8/16 | S8/32 | — | — |

Where S1/2 to S8/2 in columns 1 and 6 represent 1× diluted sera and Sx/4, Sx/8, Sx/16 and Sx/32 the twofold serial dilutions. The last plates also contained four wells filled with 100 µl fetal calf serum as a negative control. Plates were kept at −20° C. until further use.

Preparation of Human Adenovirus Stocks

Prototypes of all known human adenoviruses were inoculated on T25 flasks seeded with PER.C6 cells (Fallaux et al., 1998) and harvested upon full CPE. After freeze/thawing 1–2 ml of the crude lysates was used to inoculate a T80 flask with PER.C6 and virus was harvested at full CPE. The timeframe between inoculation and occurrence of CPE as well as the amount of virus needed to re-infect a new culture, differed between serotypes. Adenovirus stocks were prepared by freeze/thawing and used to inoculate 3–4 T175 cm$^2$ three-layer flasks with PER.C6 cells. Upon occurrence of CPE, cells were harvested by tapping the flask, pelleted and virus was isolated and purified by a two-step CsCl gradient as follows. Cell pellets were dissolved in 50 ml 10 mM NaPO$_4$ buffer (pH 7.2) and frozen at −20° C. After thawing at 37° C., 5.6 ml sodium deoxycholate (5% w/v) was added. The solution was mixed gently and incubated for 5–15 minutes at 37° C. to completely lyse the cells. After homogenizing the solution, 1875 µl 1M MgCl$_2$ was added. After the addition of 375 µl DNAse (10 mg/ml) the solution was incubated for 30 minutes at 37° C. Cell debris was removed by centrifugation at 1880×g for 30 minutes at RT without brake. The supernatant was subsequently purified from proteins by extraction with FREON (3x). The cleared supernatant was loaded on a 1M Tris/HCl buffered cesium chloride block gradient (range: 1.2/1.4 g/ml) and centrifuged at 21000 rpm for 2.5 hours at 10° C. The virus band is isolated after which a second purification using a 1 M Tris/HCl buffered continues gradient of 1.33 g/ml of cesium chloride was performed. The virus was then centrifuged for 17 hours at 55000 rpm at 10° C. The virus band is isolated and sucrose (50% w/v) is added to a final concentration of 1%. Excess cesium chloride is removed by dialysis (three times 1 hr at RT) in dialysis slides (Slide-a-lizer, cut off 10000 kDa, Pierce, USA) against 1.5 liter PBS supplemented with CaCl$_2$ (0.9 mM), MgCl$_2$ (0.5 mM) and an increasing concentration of sucrose (1, 2, 5%). After dialysis, the virus is removed from the slide-a-lizer after which it is aliquoted in portions of 25 and 100 µl upon which the virus is stored at −85° C.

To determine the number of virus particles per milliliter, 50 µl of the virus batch is run on a high-pressure liquid chromatograph (HPLC) as described by Shabram et al (1997). Viruses were eluted using a NaCl gradient ranging from 0 to 600 mM. As depicted in table I, the NaCl concentration by which the viruses were eluted differed significantly among serotypes.

Most human adenoviruses replicated well on PER.C6 cells with a few exceptions. Adenovirus type 8 and 40 were grown on 911-E4 cells (He et al., 1998). Purified stocks contained between $5 \times 10^{10}$ and $5 \times 10^{12}$ virus particles/ml (VP/ml; see table I).

Titration of Purified Human Adenovirus Stocks

Adenoviruses were titrated on PER.C6 cells to determine the amount of virus necessary to obtain full CPE in five days, the length of the neutralization assay. Hereto, 100 µl medium was dispensed into each well of 96-well plates. 25 µl of adenovirus stocks pre-diluted $10^4$, $10^5$, $10^6$ or $10^7$ times were added to column 2 of a 96-well plate and mixed by pipetting up and down 10 times. Then 25 µl was brought from column 2 to column 3 and again mixed. This was repeated until column 1 1 after which 25 µl from column 11 was discarded. This way, serial dilutions in steps of 5 were obtained starting off from a pre-diluted stock. Then $3 \times 10^4$ PER.C6 cells (ECACC deposit number 96022940) were added in a 100 µl volume and the plates were incubated at 37° C., 5% CO$_2$ for five or six days. CPE was monitored microscopically. The method of Reed and Muensch was used to calculate the cell culture-inhibiting dose 50% (CCID50).

In parallel, identical plates were set up that were analyzed using the MTT assay (Promega). In this assay, living cells are quantified by calorimetric staining. Hereto, 20 µl MTT (7.5 mgr/ml in PBS) was added to the wells and incubated at 37° C., 5% CO$_2$ for two hours. The supernatant was removed and 100 µl of a 20:1 isopropanol/triton-X100 solution was added to the wells. The plates were put on a 96-well shaker for 3–5 minutes to solubilize the precipitated staining. Absorbance was measured at 540 nm and at 690 nm (background). By this assay, wells with proceeding CPE or full CPE can be distinguished.

Neutralization Assay 96-well plates with diluted human serum samples were thawed at 37° C., 5% CO$_2$. Adenovirus stocks diluted to 200 CCID50 per 50 µl were prepared and 50 µl aliquots were added to columns 1–11 of the plates with serum. Plates were incubated for 1 hour at 37° C., 5% CO$_2$. Then 50 µl PER.C6 cells at $6 \times 10^5$/ml were dispensed in all wells and incubated for 1 day at 37° C., 5% CO2. Supernatant was removed using fresh pipette tips for each row and 200 µl fresh medium was added to all wells to avoid toxic effects of the serum. Plates were incubated for another 4 days at 37° C., 5% CO$_2$. In addition, parallel control plates were set up in duplo with diluted positive control sera generated in rabbits and specific for each serotype to be tested in rows A and B and with negative control serum (FCS) in rows C and D. Also, in each of the rows E–H a titration was performed as described above with steps of five times dilutions starting with 200 CCID50 of each virus to be tested. On day 5, one of the control plates was analyzed microscopically and with the MTT assay. The experimental titer was calculated from the control titration plate observed microscopically. If CPE was found to be complete, i.e. the first dilution in the control titration experiment analyzed by MTT shows clear cell death, all assay plates were processed. If not, the assay was allowed to proceed for one or more days until full CPE was apparent after which all plates were processed. In most cases, the assay was terminated at day 5. For Ad1, 5, 33, 39, 42 and 43 the assay was left for six days and for Ad2 for eight days.

A serum sample is regarded as "non-neutralizing" when, at the highest serum concentration, a maximum protection of 40% is seen compared to controls without serum.

The results of the analysis of 44 prototype adenoviruses against serum from 100 healthy volunteers are shown in FIG. 1. As expected, the percentage of serum samples that contained neutralizing antibodies to Ad2 and Ad5 was very high. This was also true for most of the lower numbered adenoviruses. Surprisingly, none of the serum samples contained neutralizing antibodies to Ad35. Also, the number of individuals with neutralizing antibody titers to the serotypes 26, 34 and 48 was very low. Therefore, recombinant E1-deleted adenoviruses based on Ad35 or one of the other above mentioned serotypes have an important advantage compared to recombinant vectors based on Ad5 with respect to clearance of the viruses by neutralizing antibodies.

Also, Ad5-based vectors that have (parts of) the capsid proteins involved in immunogenic response of the host replaced by the corresponding (parts of) the capsid proteins of Ad35 or one of the other serotypes will be less, or even not, neutralized by the vast majority of human sera.

Figure 2:
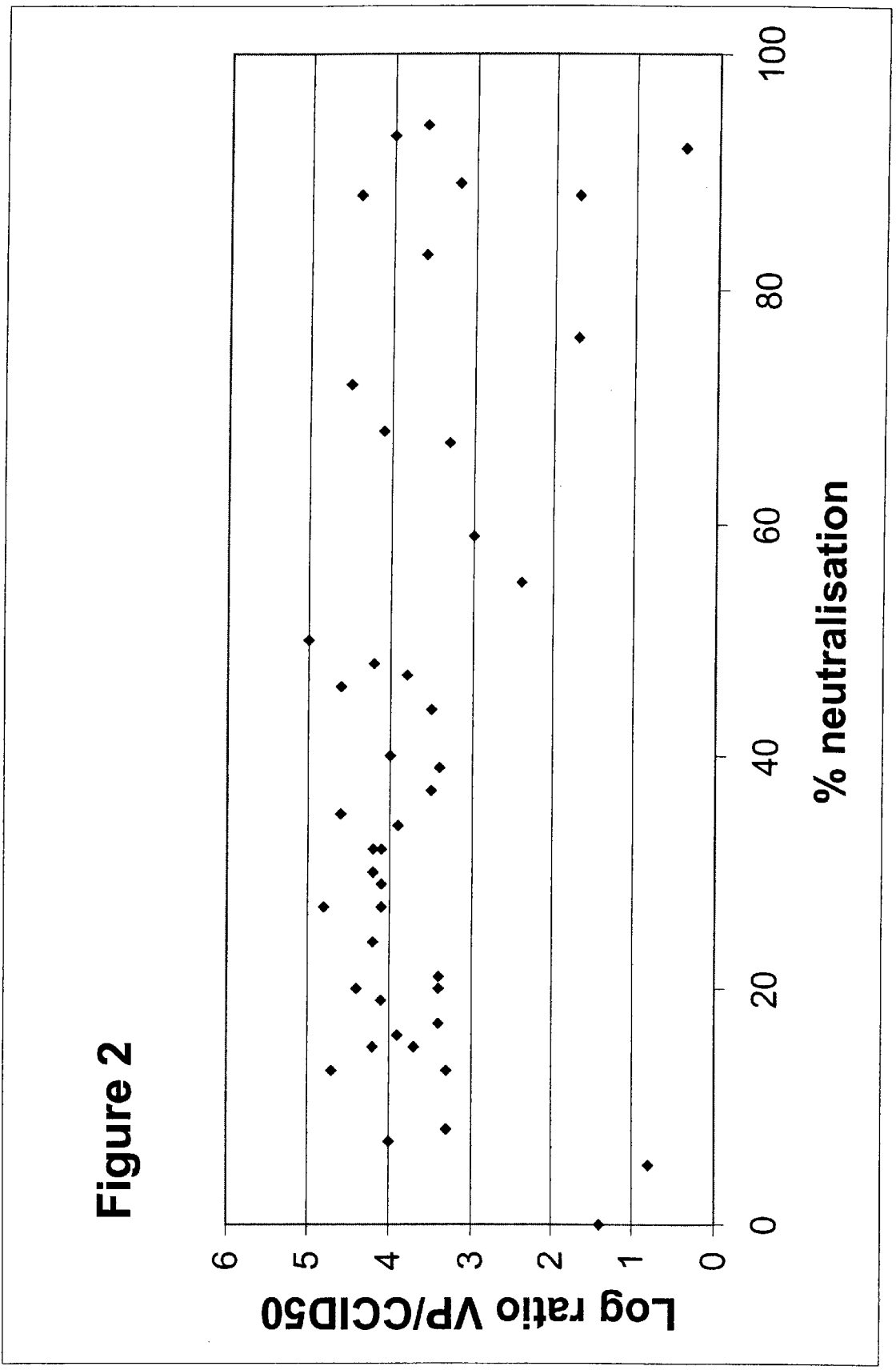
FIG. 2: Graph showing absence of correlation between the VP/CCID50 ratio and the percentage of neutralization.

As can be seen in Table I, the VP/CCID50 ratio calculated from the virus particles per ml and the CCID50 obtained for each virus in the experiments was highly variable, and ranged from 0.4 to 5 log. This is probably caused by different infection efficiencies of PER.C6 cells and by differences in replication efficiency of the viruses. Furthermore, differences in batch qualities may play a role. A high VP/CCID50 ratio means that more viruses were put in the wells to obtain CPE in 5 days. As a consequence, the outcome of the neutralization study might be biased since more (inactive) virus particles could shield the antibodies. To check whether this phenomenon had taken place, the VP/CCID50 ratio was plotted against the percentage of serum samples found positive in the assay (FIG. 2). The graph clearly shows that there is no negative correlation between the amount of viruses in the assay and neutralization in serum.

Example 2

The Prevalence of Neutralizing Activity (NA) to Ad35 is Low in Human Sera from Different Geographic Locations In Example 1 the analysis of neutralizing activity ("NA") in human sera from one location in Belgium was described. Strikingly, of a panel of 44 adenovirus serotypes tested, one serotype, Ad35, was not neutralized in any of the 100 sera assayed. In addition, a few serotypes, Ad26, Ad34 and Ad48 were found to be neutralized in 8%, or less, of the sera tested. This analysis was further extended to other serotypes of adenovirus not previously tested and, using a selection of serotypes from the first screen, was also extended to sera from different geographic locations.

Hereto, adenoviruses were propagated, purified and tested for neutralization in the CPE-inhibition assay as described in Example 1. Using the sera from the same batch as in Example 1, adenovirus serotypes 7B, 11, 14, 18 and 44/1876 were tested for neutralization. These viruses were found to be neutralized in, respectively, 59, 13, 30, 98 and 54% of the sera. Thus, of this series, Ad11 is neutralized with a relatively low frequency.

Since it is known that the frequency of isolation of adenovirus serotypes from human tissue as well as the prevalence of NA to adenovirus serotypes may differ on different geographic locations, we further tested a selection of the adenovirus serotypes against sera from different places. Human sera were obtained from two additional places in Europe (Bristol, UK and Leiden, NL) and from two places in the United States (Stanford, Calif. and Great Neck, N.Y.). Adenoviruses that were found to be neutralized in 20% or less of the sera in the first screen, as well as Ad2, Ad5, Ad27, Ad30, Ad38, Ad43, were tested for neutralization in sera from the UK. The results of these experiments are presented in FIG. 3. Adenovirus serotypes 2 and 5 were again neutralized in a high percentage of human sera. Furthermore, some of the serotypes that were neutralized in a low percentage of sera in the first screen are neutralized in a higher percentage of sera from the UK, for example, Ad26 (7% vs. 30%), Ad28 (13% vs. 50%), Ad34 (5% vs. 27%) and Ad48 (8% vs. 32%). Neutralizing activity against Ad11 and Ad49 that were found in a relatively low percentage of sera in the first screen, are found in an even lower percentage of sera in this second screen (13% vs. 5% and 20% vs. 11% respectively). Serotype Ad35 that was not neutralized in any of the sera in the first screen, was now found to be neutralized in a low percentage (8%) of sera from the UK. The prevalence of NA in human sera from the UK is the lowest to serotypes Ad11 and Ad35.

For further analysis, sera obtained from two locations in the US (Stanford, Calif. and Great Neck, N.Y.) and from The Netherlands (Leiden). FIG. 4 presents an overview of data obtained with these sera and the previous data. Not all viruses were tested in all sera, except for Ad5, Ad11 and Ad35. The overall conclusion from this comprehensive screen of human sera is that the prevalence of neutralizing activity to Ad35 is the lowest of all serotypes throughout the western countries: on average 7% of the human sera contain neutralizing activity (5 different locations). Another B-group adenovirus, Ad11 is also neutralized in a low percentage of human sera (average 11% in sera from 5 different locations). Adenovirus type 5 is neutralized in 56% of the human sera obtained from 5 different locations. Although not tested in all sera, D-group serotype 49 is also neutralized with relatively low frequency in samples from Europe and from one location of the US (average 14%).

In the herein described neutralization experiments, a serum is judged non-neutralizing when, in the well with the highest serum concentration, the maximum protection of CPE is 40% compared to the controls without serum. The protection is calculated as follows:

$$\% \text{ protection} = \frac{\text{OD corresponding well} - \text{OD virus control}}{\text{OD non-infected control} - \text{OD virus control}} \times 100\%$$

As described in Example 1, the serum is plated in five different dilutions ranging from 4× to 64× diluted. Therefore, it is possible to distinguish between low titers (i.e., neutralization only in the highest serum concentrations) and high titers of NA (i.e., also neutralization in wells with the lowest serum concentration). Of the human sera used in our screen that were found to contain neutralizing activity to Ad5, 70% turned out to have high titers whereas of the sera that contained NA to Ad35, only 15% had high titers. Of the sera that were positive for NA to Ad11 only 8% had high titers. For Ad49, this was 5%. Therefore, not only is the frequency of NA to Ad35, Ad11 and Ad49 much lower as compared to Ad5, but of the sera that do contain NA to these viruses, the vast majority has low titers. Adenoviral vectors based on Ad 11, Ad35 or Ad49 have therefore a clear advantage over Ad5 based vectors when used as gene therapy vehicles or vaccination vectors in vivo or in any application where infection efficiency is hampered by neutralizing activity.

In the following examples, the construction of a vector system for the generation of safe, RCA-free Ad35-based vectors is described.

Example 3

Sequence of the Human Adenovirus Type 35

Ad35 viruses were propagated on PER.C6 cells and DNA was isolated as follows: To 100 µl of virus stock (Ad35: $3.26 \times 10^{12}$ VP/mil), 10µl 10× DNAse buffer (130 mM Tris-HCl pH7.5; 1,2 M CaCl$_2$; 50 mM MgCl$_2$) was added. After addition of 10 µl 10 mgr/ml DNAse I (Roche Diagnostics), the mixture was incubated for 1 hr. at 37° C. Following addition of 2.5 µl 0.5M EDTA, 3.2 µl 20% SDS and 1.5µl ProteinaseK (Roche Diagnostics; 20 mgr/ml), samples were incubated at 50° C. for 1 hr. Next, the viral DNA was isolated using the GENECLEAN spin kit (Bio101 Inc.) according to the manufacturer's instructions. DNA was eluted from the spin column with 25 µl sterile MilliQ water. The total sequence was generated by Qiagen Sequence Services (Qiagen GmbH, Germany). Total viral DNA was sheared by sonification and the ends of the DNA were made blunt by T4 DNA polymerase. Sheared blunt fragments were size fractionated on agarose gels and gel slices corresponding to DNA fragments of 1.8 to 2.2 kb were obtained. DNA was purified from the gel slices by the QIAquick gel extraction protocol and subcloned into a shotgun library of pUC19 plasmid cloning vectors. An array of clones in 96-well plates covering the target DNA 8 (+/−2) times was used to generate the total sequence. Sequencing was performed on Perkin-Elmer 9700 thermocyclers using Big Dye Terminator chemistry and AmpliTaq FS DNA polymerase followed by purification of sequencing reactions using QIAGEN DyeEx 96 technology. Sequencing reaction products were then subjected to automated separation and detection of fragments on ABI 377 XL 96 lane sequencers. Initial sequence results were used to generate a contiguous sequence and gaps were filled in by primer walking reads on the target DNA or by direct sequencing of PCR products. The ends of the virus turned out to be absent in the shotgun library, most probably due to cloning difficulties resulting from the amino acids of pTP that remain bound to the ITR sequences after proteinase K digestion of the viral DNA. Additional sequence runs on viral DNA solved most of the sequence in those regions, however it was difficult to obtain a clear sequence of the most terminal nucleotides. At the 5' end the sequence portion obtained was 5'-CCAATAATATACCT-3' (SEQ ID NO: 1) while at the 3' end, the obtained sequence portion was 5'-AGGTATATTATTGATGATGGG-3' (SEQ ID NO: 2). Most human adenoviruses have a terminal sequence 5'-CATCATCAATAATATACC-3' (SEQ ID NO: 3). In addition, a clone representing the 3' end of the Ad35 DNA obtained after cloning the terminal 7 kb Ad35 EcoRI fragment into pBr322 also turned out to have the typical CAT-CATCAATAAT... sequence. Therefore, Ad35 may have the typical end sequence and the differences obtained in sequencing directly on the viral DNA are due to artefacts correlated with run-off sequence runs and the presence of residual amino acids of pTP.

The total sequence of Ad35 with corrected terminal sequences is given in FIG. 5 and identified as SEQ ID NO: 39 in the SEQUENCE LISTING. Based sequence homology with Ad5 (Genbank #M72360) and Ad7 (partial sequence Genbank #X03000) and on the location of open reading frames, the organization of the virus is identical to the general organization of most human adenoviruses, especially the subgroup B viruses. The total length of the genome is 34,794 basepairs.

Example 4

Construction of a Plasmid-based Vector System to Generate Recombinant Ad35-based Viruses A functional plasmid-based vector system to generate recombinant adenoviral vectors comprises the following components:

1. An adapter plasmid comprising a left ITR and packaging sequences derived from Ad35 and at least one restriction site for insertion of an heterologous expression cassette and lacking E1 sequences. Furthermore, the adapter plasmid contains Ad35 sequences 3' from the E1B coding region including the pIX promoter and coding sequences enough to mediate homologous recombination of the adapter plasmid with a second nucleic acid molecule.

2. A second nucleic acid molecule, comprising sequences homologous to the adapter plasmid, and Ad35 sequences necessary for the replication and packaging of the recombinant virus, that is early, intermediate and late genes that are not present in the packaging cell.

3. A packaging cell providing at least functional E1 proteins capable of complementing the E1 function of Ad35.

Other methods for generating recombinant adenoviruses on complementing packaging cells are known in the art, and may be applied to Ad35 viruses without departing from the invention. As an example, the construction of a plasmid-based system, as outlined above, is described in detail below.

1) Construction of Ad35 Adapter Plasmids.

The adapter plasmid pAdApt (described in International Patent Application WO99/55 132) was first modified to obtain adapter plasmids that contain extended polylinkers and that have convenient unique restriction sites flanking the left ITR and the adenovirus sequence at the 3' end to enable liberation of the adenovirus insert from plasmid vector sequences. Construction of these plasmids is described below in detail:

Adapter plasmid pAdApt was digested with SalI and treated with Shrimp Alkaline Phosphatase to reduce religation. A linker, composed of the following two phosphorylated and annealed oligos: ExSalPacF 5'-TCG ATG GCA AAC AGC TAT TAT GGG TAT TAT GGG TTC GAA TTA ATT AA-3' (SEQ ID NO: 4) and ExSalPacR 5'-TCG ATT AAT TAA TTC GAA CCC ATA ATA CCC ATA ATA GCT GTT TGC CA-3' (SEQ ID NO: 5) was directly ligated into the digested construct, thereby replacing the SalI restriction site by Pi-PspI, SwaI and PacI. This construct was designated pADAPT+ExSalPac linker. Furthermore, part of the left ITR of pAdApt was amplified by PCR using the following primers: PCLIPMSF: 5'-CCC CAA TTG GTC GAC CAT CAT CAA TAA TAT ACC TTA TTT TGG-3' (SEQ ID NO: 6) and pCLIPBSRGI: 5'-GCG AAA ATT GTC ACT TCC TGT G-3' (SEQ ID NO: 7). The amplified fragment was digested with MunI and BsrGI and cloned into pAd5/Clip (described in International Patent Application WO99/55132), which was partially digested with EcoRI and after purification digested with BsrGI, thereby re-inserting the left ITR and packaging signal. After restriction enzyme analysis, the construct was digested with ScaI and SgrAI and an 800 bp fragment was isolated from gel and ligated into ScaI/SgrAI digested pADAPT+ExSalPac linker. The resulting construct, designated pIPspSalAdapt, was digested with SalI, dephosphorylated, and ligated to the phosphorylated ExSalPacF/ExSalPacR double-stranded linker previously mentioned. A clone in which the PacI site was closest to the ITR was identified by restriction analysis and sequences were confirmed by sequence analysis. This novel pAdApt construct, termed pIPspAdapt thus harbours two ExSalPac linkers containing recognition sequences for PacI, PI-PspI and BstBI, which surround the adenoviral part of the adenoviral adapter construct, and which can be used to linearize the plasmid DNA prior to cotransfection with adenoviral helper fragments.

In order to further increase transgene cloning permutations, a number of polylinker variants were constructed based on pIPspAdapt. For this purpose, pIPspAdapt was first digested with EcoRI and dephosphorylated. A linker composed of the following two phosphorylated and annealed oligos: Ecolinker+: 5'-AAT TCG GCG CGC CGT CGA CGA TAT CGA TAG CGG CCG C-3'(SEQ ID NO: 8) and Ecolinker−: 5'-AAT TGC GGC CGC TAT CGA TAT CGT CGA CGG CGC GCC G-3' (SEQ ID NO: 9) was ligated into this construct, thereby creating restriction sites for AscI, SalI, EcoRV, ClaI and NotI. Both orientations of this linker were obtained, and sequences were confirmed by restriction analysis and sequence analysis. The plasmid containing the polylinker in the order 5' HindIII, KpnI, AgeI, EcoRI, AscI, SalI, EcoRV, ClaI, NotI, NheI, HpaI, BamHI and XbaI was termed pIPspAdapt1 while the plasmid containing the polylinker in the order HindIII, KpnI, AgeI, NotI, ClaI, EcoRV, SalI, AscI, EcoRI, NheI, HpaI, BamHI and XbaI was termed pIPspAdapt2.

To facilitate the cloning of other sense or antisense constructs, a linker composed of the following two oligonucleotides was designed, to reverse the polylinker of pIPspAdapt: HindXba+5'-AGC TCT AGA GGA TCC GTT AAC GCT AGC GAA TTC ACC GGT ACC AAG CTT A-3' (SEQ ID NO: 10); HindXba-5'-CTA GTA AGC TTG GTA CCG GTG AAT TCG CTA GCG TTA ACG GAT CCT CTA G-3' (SEQ ID NO: 11). This linker was ligated into HindIII/XbaI digested pIPspAdapt and the correct construct was isolated. Confirmation was done by restriction enzyme analysis and sequencing. This new construct, pIPspAdaptA, was digested with EcoRI and the previously mentioned Ecolinker was ligated into this construct. Both orientations of this linker were obtained, resulting in pIPspAdapt3, which contains the polylinker in the order XbaI, BamHI, HpaI, NheI, EcoRI, AscI, SalI, EcoRV, ClaI, NotI, AgeI, KpnI and HindIII. All sequences were confirmed by restriction enzyme analysis and sequencing.

Adapter plasmids based on Ad35 were then constructed as follows:
The left ITR and packaging sequence corresponding to Ad35 wt sequences nucleotides 1 to 464 (FIG. 5) were amplified by PCR on wtAd35 DNA using the following primers:
Primer 35F1:
  5'-CGG AAT TCT TAA TTA ATC GAC ATC ATC AAT AAT ATA CCT TAT AG-3' (SEQ ID NO: 12)
Primer 35R2:
  5'-GGT GGT CCT AGG CTG ACA CCT ACG TAA AAA CAG-3' (SEQ ID NO: 13)
Amplification introduces a PacI site at the 5' end and an AvrII site at the 3' end of the sequence.

For the amplification, Platinum Pfx DNA polymerase enzyme (LTI) was used according to manufacturer's instructions, but with primers at 0.6 µM and with DMSO added to a final concentration of 3%. Amplification program was as follows: 2 min. at 94° C., (30 sec. 94° C., 30 sec. at 56° C., 1 min. at 68° C.) for 30 cycles, followed by 10 min. at 68° C.

The PCR product was purified using a PCR purification kit (LTI) according to the manufacturer's instructions, and digested with PacI and AvrII. The digested fragment was then purified from gel using the GENECLEAN kit (Bio 101, Inc.). The Ad5-based adapter plasmid pIPspAdApt-3 was digested with AvrII and then partially with PacI and the 5762 bp fragment was isolated in an LMP agarose gel slice and ligated with the abovementioned PCR fragment digested with the same enzymes and transformed into electrocompetent DH10B cells (LTI). The resulting clone is designated pIPspAdApt3-Ad35ITR.

Figure 6:
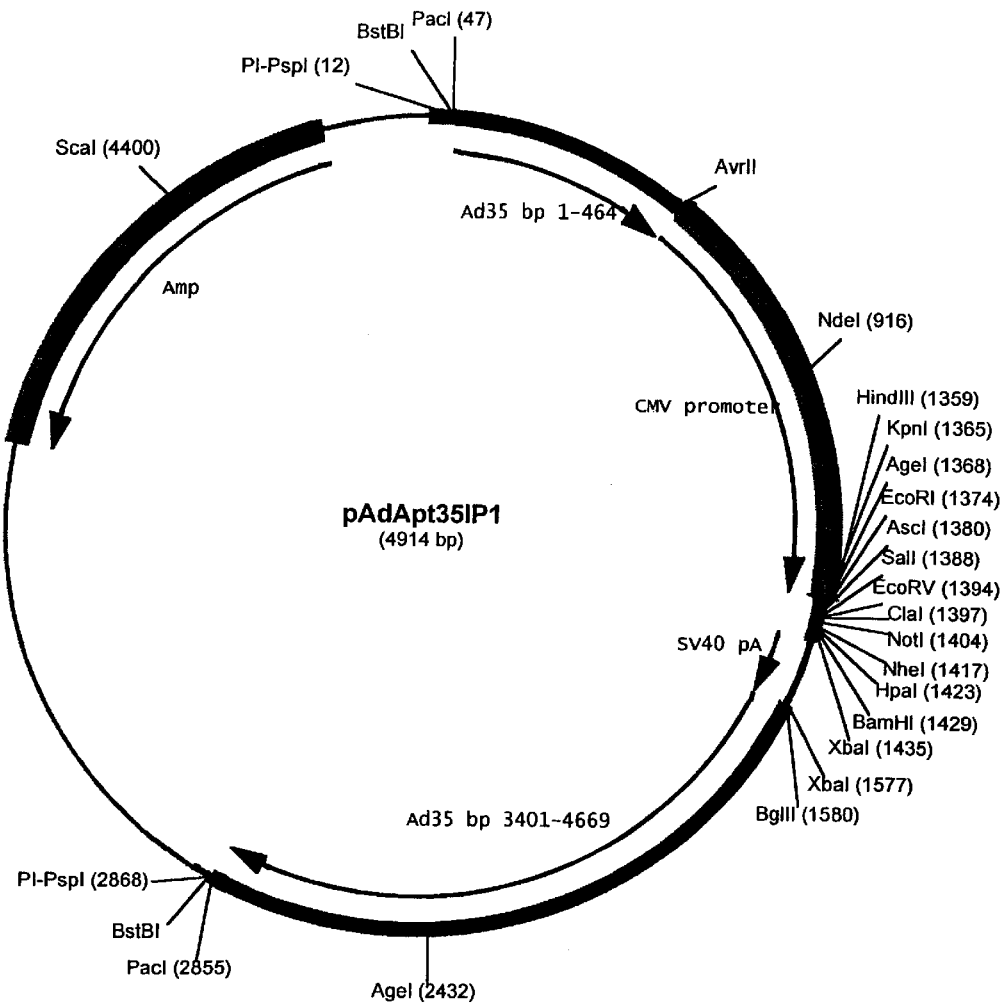
FIG. 6: Map of pAdApt35IP1.

In parallel, a second piece of Ad35 DNA was amplified using the following primers:
  35F3: 5'-TGG TGG AGA TCT GGT GAG TAT TGG GAA AAC-3' (SEQ ID NO: 14)
  35R4: 5'-CGG AAT TCT TAA TTA AGG GAA ATG CAA ATC TGT GAG G-3' (SEQ ID NO: 15)
The sequence of this fragment corresponds to nucleotides 3401 to 4669 of wtAd35 (FIG. 5) and contains 1.3 kb of sequences starting directly 3' from the E1B 55k coding sequence. Amplification and purification were done as previously described herein for the fragment containing the left ITR and packaging sequence. The PCR fragment was then digested with PacI and subcloned into pNEB 193 vector (New England Biolabs) digested with SmaI and PacI. The integrity of the sequence of the resulting clone was checked by sequence analysis. pNEB/Ad35pF3R4 was then digested with BglII and PacI and the Ad35 insert was isolated from gel using the QIAExII kit (Qiagen). pIPspAdApt3-Ad35ITR was digested with BglII and then partially with PacI. The 3624 bp fragment (containing vector sequences, the Ad35 ITR and packaging sequences as well as the CMV promoter, multiple cloning region and polyA signal) was also isolated using the QIAExII kit (Qiagen). Both fragments were ligated and transformed into competent DH10B cells (LTI). The resulting clone, pAdApt35IP3, has the expression cassette from pIPspAdApt3 but contains the Ad35 left ITR and packaging sequences and a second fragment corresponding to nucleotides 3401 to 4669 from Ad35. A second version of the Ad35 adapter plasmid having the multiple cloning site in the opposite orientation was made as follows:

pIPspAdapt1 was digested with NdeI and BglII and the 0.7 kbp band containing part of the CMV promoter, the MCS and SV40 polyA was isolated and inserted in the corresponding sites of pAdApt35IP3 generating pAdApt35IP1 (FIG. 6).

pAdApt35.LacZ and pAdApt35.Luc adapter plasmids were then generated by inserting the transgenes from pcDNA.LacZ (digested with KpnI and BamHI) and pAdApt.Luc (digested with HindIII and BamHI) into the corresponding sites in pAdApt35IP1. The generation of pcDNA.LacZ and pAdApt.Luc is described in International Patent Application WO99/55132.

Figure 7:
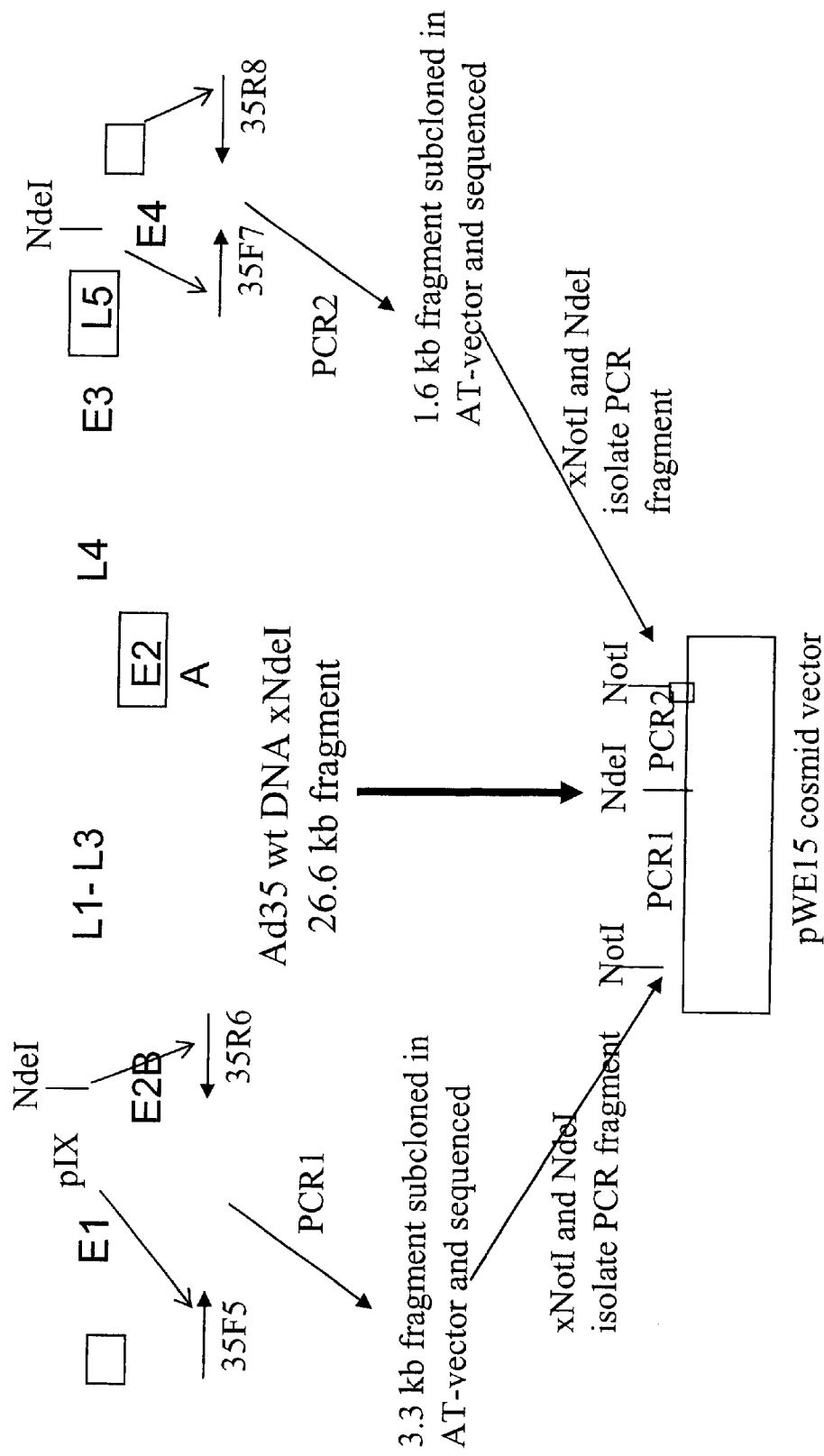
FIG. 7: Schematic representation of the steps undertaken to construct pWE.Ad35.pIX-rITR.

2) Construction of Cosmid pWE.Ad35.pIX-rITR
FIG. 7 presents the various steps undertaken to construct the cosmid clone containing Ad35 sequences from bp 3401 to 34794 (end of the right ITR) that are described in detail below.

A first PCR fragment (pIX-NdeI) was generated using the following primer set:
  35F5: 5'-CGG AAT TCG CGG CCG CGG TGA GTA TTG GGA AAA C-3' (SEQ ID NO: 16)

35R6: 5'-COC CAG ATC GTC TAC AGA ACA G-3' (SEQ ID NO: 17)

DNA polymerase Pwo (Roche) was used according to manufacturer's instructions, however, with an end concentration of 0.6 pM of both primers and using 50 ngr wt Ad35 DNA as template. Amplification was done as follows: 2 min. at 94° C., 30 cycles of 30 sec. at 94° C., 30 sec. at 65° C. and 1 min. 45 sec. at 72° C., follow at 68° C. To enable cloning in the TA cloning vector PCR2.1, a last incubation with 1 unit superTaq polymerase (HT Biotechnology LTD) for 10 min. at 72° C. was performed.

The 3370 bp amplified fragment contains Ad35 sequences from bp 3401 to 6772 with a NotI site added to the 5' end. Fragments were purified using the PCR purification kit (LTI).

A second PCR fragment (NdeI-rITR) was generated using the following primers:

35F7: 5'-GAA TGC TGG CTT CAG TTG TAA TC-3' (SEQ ID NO: 18)

35R8: 5'-CGG AAT TCG CGG CCG CAT TTA AAT CAT CAT CAA TAA TAT ACC-3' (SEQ ID NO: 19)

Amplification was done with pfx DNA polymerase (LTI) according to manufacturer's instructions but with 0.6 lM of both primers and 3% DMSO using 10 ngr. of wtAd35 DNA as template. The program was as follows: 3 min. at 94° C. and 5 cycles of 30 sec. at 94° C., 45 sec. at 40° C., 2 min.45 sec. at 68° C. followed by 25 cycles of 30 sec. at 94° C., 30 sec. at 60° C., 2 min.45 sec. at 68° C. To enable cloning in the TA-cloning vector PCR2.1, a last incubation with 1 unit superTaq polymerase for 10 min. at 72° C. was performed. The 1.6 kb amplified fragment ranging from nucleotides 33178 to the end of the right ITR of Ad35, was purified using the PCR purification kit (LTI).

Figure 8:
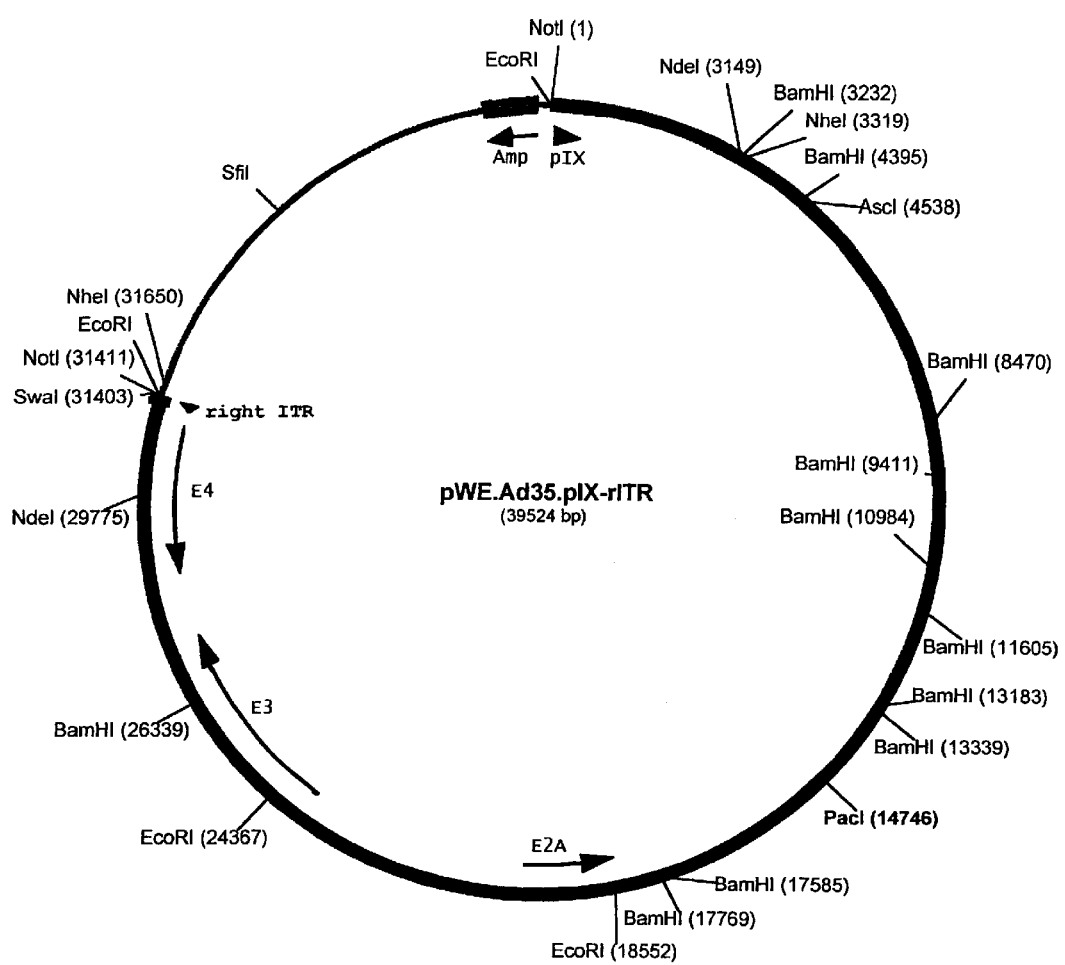
FIG. 8: Map of pWE.Ad35.pIX-rITR.

Both purified PCR fragments were ligated into the PCR2.1 vector of the TA-cloning kit (Invitrogen) and transformed into STBL-2 competent cells (LTD). Clones containing the expected insert were sequenced to confirm correct amplification. Next, both fragments were excised from the vector by digestion with NotI and NdeI and purified from gel using the GENECLEAN kit (BIO 101, Inc.). Cosmid vector pWE15 (Clontech) was digested with NotI, dephosphorylated and also purified from gel. These three fragments were ligated and transformed into STBL2 competent cells (LTI). One of the correct clones that contained both PCR fragments was then digested with NdeI, and the linear fragment was purified from gel using the GENECLEAN kit. Ad35 wt DNA was digested with NdeI and the 26.6 kb fragment was purified from LMP gel using agarase enzyme (Roche) according to the manufacturer's instructions. These fragments were ligated together and packaged using λ1 phage packaging extracts (Stratagene) according to the manufacturer's protocol. After infection into STBL-2 cells, colonies were grown on plates and analysed for presence of the complete insert. One clone with the large fragment inserted in the correct orientation and having the correct restriction patterns after independent digestions with three enzymes (NcoI, PvuII and ScaI) was selected. This clone is designated pWE.Ad35.pIX-rITR. It contains the Ad35 sequences from bp 3401 to the end and is flanked by NotI sites (FIG. 8).

3) Generation of Ad35 Based Recombinant Viruses on PER.C6.

Wild type Ad35 virus can be grown on PER.C6 packaging cells to very high titers. However, whether the Ad5-E1 region that is present in PER.C6 is able to complement E1-deleted Ad35 recombinant viruses is unknown. To test this, PER.C6 cells were cotransfected with the above described adapter plasmid pAdApt35.LacZ and the large backbone fragment pWE.Ad35.pIX-rITR. First, pAdApt35.LacZ was digested with PacI and pWE.Ad35.pIX-rITR was digested with NotI. Without further purification, 4 μgr of each construct was mixed with DMEM (LTI) and transfected into PER.C6 cells, seeded at a density of 5×10$^6$ cells in a T25 flask the day before, using Lipofectamin (LTI) according to the manufacturer's instructions. As a positive control, 6μgr of PacI digested pWE.Ad35.pIX-rITR DNA was cotransfected with a 6.7 kb NheI fragment isolated from Ad35 wt DNA containing the left end of the viral genome including the E1 region. The next day, medium (DMEM with 10% FBS and 10 mM MgCl$_2$) was refreshed and cells were further incubated. At day 2 following the transfection, cells were trypsinized and transferred to T80 flasks. The positive control flask showed CPE at five days following transfection, showing that the pWE.Ad35.pIX-rITR construct is functional at least in the presence of Ad35-E1 proteins. The transfection with the Ad35 LacZ adapter plasmid and pWE.Ad35.pIX-rITR did not give rise to CPE. These cells were harvested in the medium at day 10 and freeze/thawed once to release virus from the cells. 4 ml of the harvested material was added to a T80 flask with PER.C6 cells (at 80% confluency) and incubated for another five days. This harvest/re-infection was repeated for two times but there was no evidence for virus associated CPE.

From this experiment, it seems that the Ad5-E1 proteins are not, or not well enough, capable of complementing Ad35 recombinant viruses, however, it may be that the sequence overlap of the adapter plasmid and the pWE.Ad35.pIX-rITR backbone plasmid is not large enough to efficiently recombine and give rise to a recombinant virus genome. The positive control transfection was done with a 6.7 kb left end fragment and therefore the sequence overlap was about 3.5 kb. The adapter plasmid and the pWE.Ad35.pIX-rITR fragment have a sequence overlap of 1.3 kb. To check whether the sequence overlap of 1.3 kb is too small for efficient homologous recombination, a cotransfection was done with PacI digested pWE.Ad35.pIX-rITR and a PCR fragment of Ad35 wt DNA generated with the above mentioned 35F1 and 35R4 using the same procedures as previously described herein. The PCR fragment thus contains left end sequences up to bp 4669 and, therefore, has the same overlap sequences with pWE.Ad35.pIX-rITR as the adapter plasmid pAdApt35.LacZ, but has Ad35 E1 sequences. Following PCR column purification, the DNA was digested with SalI to remove possible intact template sequences. A transfection with the digested PCR product alone served as a negative control. Four days after the transfection, CPE occurred in the cells transfected with the PCR product and the Ad35 pIX-rITR fragment, and not in the negative control. This result shows that a 1.3 kb overlapping sequence is sufficient to generate viruses in the presence of Ad35 E1 proteins. From these experiments, we conclude that the presence of at least one of the Ad3 5.E1 proteins is necessary to generate recombinant Ad35 based vectors from plasmid DNA on Ad5 complementing cell lines.

Example 5

1) Construction of Ad35.E1 Expression Plasmids

Since Ad5-E1 proteins in PER.C6 are incapable of complementing Ad35 recombinant viruses efficiently, Ad35 E1 proteins have to be expressed in Ad5 complementing cells (e.g., PER.C6). Alternatively, a new packaging cell line expressing Ad35 E1 proteins has to be made, starting from either diploid primary human cells or established cell lines not expressing adenovirus E1 proteins. To address the first possibility, the Ad35 E1 region was cloned in expression plasmids as described below.

First, the Ad35 E1 region from bp 468 to bp 3400 was amplified from wtAd35 DNA using the following primer set:

35F11: 5'-GGG GTA CCG AAT TCT CGC TAG GGT ATT TAT ACC-3' (SEQ ID NO: 20)

35F10: 5'-GCT CTA GAC CTG CAG GTT AGT CAG TTT CTT CTC CAC TG-3' (SEQ ID NO: 21)

This PCR introduces a KpnI and EcoRI site at the 5' end and an SbfI and XbaI site at the 3' end.

Figure 9:
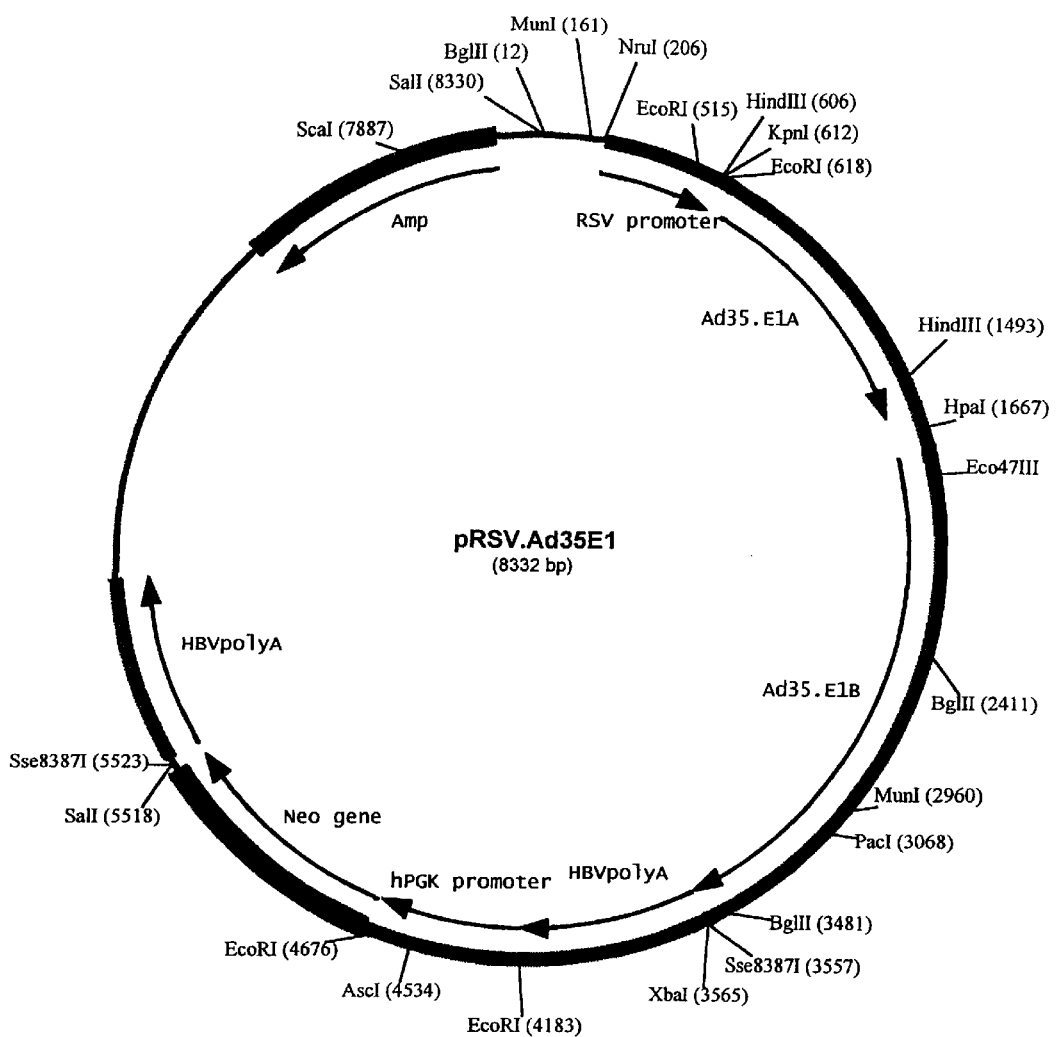
FIG. 9: Map of pRSV.Ad35-E1.
Figure 10:
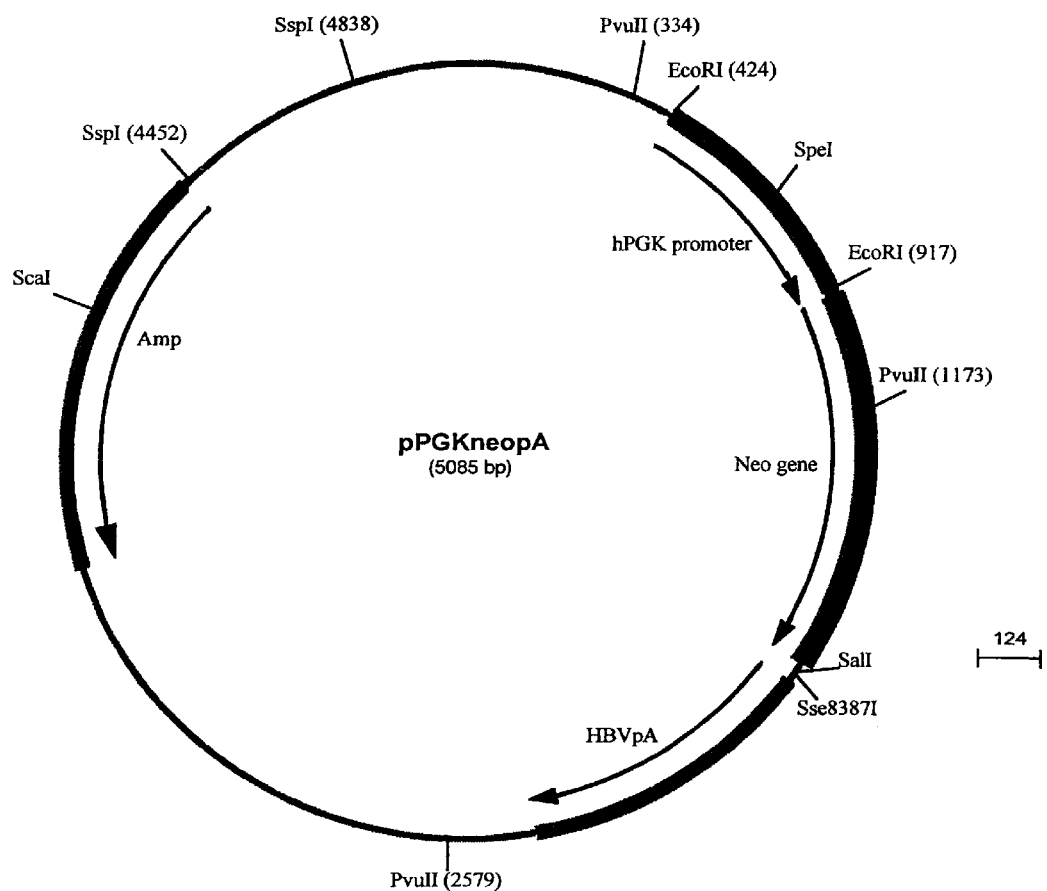
FIG. 10: Map of PGKneopA.
Figure 11:
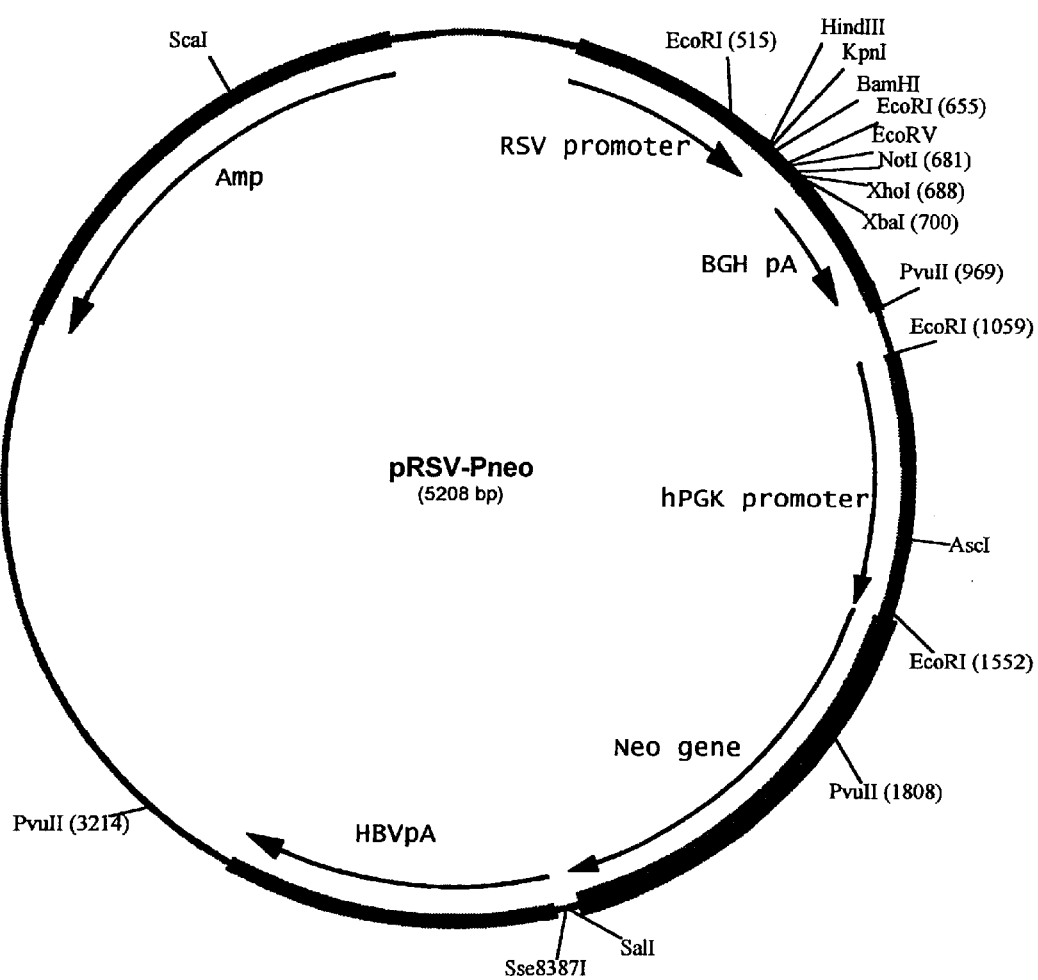
FIG. 11: Map of pRSVpNeo.

Amplification on 5 ngr. template DNA was done with Pwo DNA polymerase (Roche) using the manufacturer's instructions, however, with both primers at a final concentration of 0.6 µM. The program was as follows: 2 min. at 94° C., 5 cycles of 30 sec. at 94° C., 30 sec. at 56° C. and 2 min. at 72° C., followed by 25 cycles of 94° C., 30 sec. at 60° C. and 2 min. at 72° C., followed by 10 min. at 72° C. PCR product was purified by a PCR purification kit (LTI) and digested with KpnI and XbaI. The digested PCR fragment was then ligated to the expression vector pRSVhbvNeo (see below) also digested with KpnI and XbaI. Ligations were transformed into competent STBL-2 cells (LTI) according to manufacturer's instructions and colonies were analysed for the correct insertion of Ad35E1 sequences into the polylinker in between the RSV promoter and HBV polyA. The resulting clone was designated pRSV.Ad35-E1 (FIG. 9). The Ad35 sequences in pRSV.Ad35-E1 were checked by sequence analysis.

pRSVhbvNeo was generated as follows: pRc-RSV (Invitrogen) was digested with PvuII, dephosphorylated with TSAP enzyme (LTI), and the 3 kb vector fragment was isolated in low melting point agarose (LMP). Plasmid pPGKneopA (FIG. 10; described in International Patent Application WO96/35798) was digested with SspI completely to linearize the plasmid and facilitate partial digestion with PvuII. Following the partial digestion with PvuII, the resulting fragments were separated on a LMP agarose gel and the 2245 bp PvuII fragment, containing the PGK promoter, neomycin-resistance gene and HBVpolyA, was isolated. Both isolated fragments were ligated to give the expression vector pRSV-pNeo that now has the original SV40prom-neo-SV40polyA expression cassette replaced by a PGKprom-neo-HBVpolyA cassette (FIG. 11). This plasmid was further modified to replace the BGHpA with the HBVpA as follows: pRSVpNeo was linearised with ScaI and further digested with XbaI. The 1145 bp fragment, containing part of the Amp gene and the RSV promoter sequences and polylinker sequence, was isolated from gel using the GeneClean kit (Bio Inc. 101). Next, pRSVpNeo was linearised with ScaI and further digested with EcoRI partially and the 3704 bp fragment containing the PGKneo cassette and the vector sequences were isolated from gel as above. A third fragment, containing the HBV polyA sequence flanked by XbaI and EcoRI at the 5' and 3' end respectively, was then generated by PCR amplification on pRSVpNeo using the following primer set:

HBV-F: 5'-GGC TCT AGA GAT CCT TCG CGG GAC GTC-3' (SEQ ID NO: 22) and

HBV-R: 5'-GGC GAA TTC ACT GCC TTC CAC CAA GC-3' (SEQ ID NO: 23).

Figure 12:
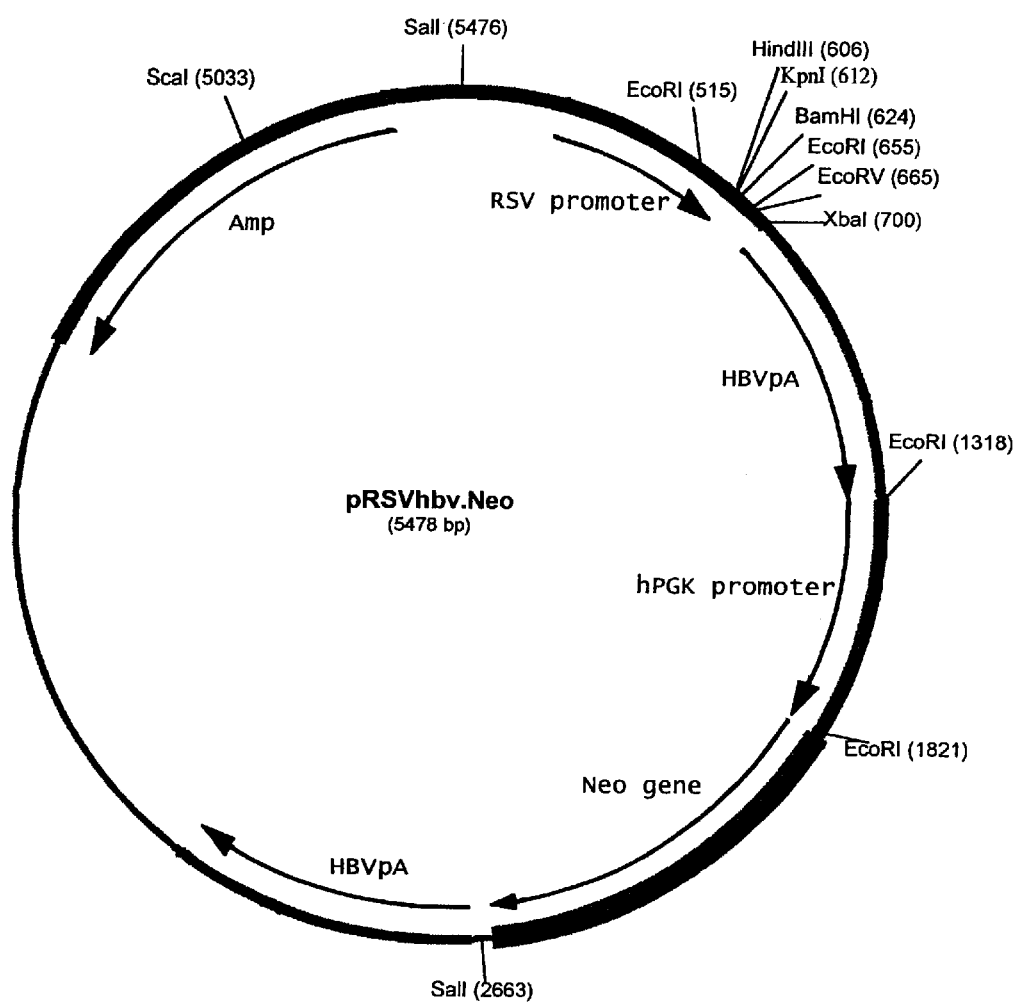
FIG. 12: Map of pRSVhbvNeo.

Amplification was done with Elongase enzyme (LTI) according to the manufacturer's instructions with the following conditions: 30 seconds at 94° C., then 5 cycles of 45 seconds at 94° C., 1 minute at 42° C. and 1 minute 68° C., followed by 30 cycles of 45 seconds at 94° C., 1 minute at 65° C. and 1 minute at 68° C., followed by 10 minutes at 68° C. The 625 bp PCR fragment was then purified using the Qiaquick PCR purification kit, digested with EcoRI and XbaI and purified from gel using the GENECLEAN kit. The three isolated fragments were ligated and transformed into DH5α competent cells (LTI) to give the construct pRSVh-bvNeo (FIG. 12). In this construct, the transcription regulatory regions of the RSV expression cassette and the neomycin selection marker are modified to reduce overlap with adenoviral vectors that often contain CMV and SV40 transcription regulatory sequences.

2) Generation of Ad35 Recombinant Viruses on PER.C6 Cells Cotransfected with an Ad35-E1 Expression Construct.

PER.C6 cells were seeded at a density of $5 \times 10^6$ cells in a T25 flask and, the next day, transfected with a DNA mixture containing:

1 µg pAdApt35.LacZ digested with PacI

1 µg pAdApt35.LacZ digested with PacI

5 µg pRSV.Ad35E1 undigested

2 µg pWE.Ad35.pIX-aITR digested with NotI

Transfection was done using Lipofectamine according to the manufacturer's instructions. Five hours after addition of the transfection mixture to the cells, medium was removed and replaced by fresh medium. After two days, cells were transferred to T80 flasks and further cultured. One week post-transfection, 1 ml of the medium was added to A549 cells and, the following day, cells were stained for LacZ expression. Blue cells were clearly visible after two hours of staining indicating that recombinant LacZ expressing viruses were produced. The cells were further cultured, but no clear appearance of CPE was noted. However, after 12 days, clumps of cells appeared in the monolayer and 18 days following transfection, cells were detached. Cells and medium were then harvested, freeze-thawed once, and 1 ml of the crude lysate was used to infect PER.C6 cells in a 6-well plate. Two days after infection, cells were stained for LacZ activity. After two hours, 15% of the cells were stained blue. To test for the presence of wt and/or replicating competent viruses, A549 cells were infected with these virused and further cultures. No signs of CPE were stained blue. To test for the replication competent viruses. These experiments show that recombinant AdApt35.LacZ viruses were made on PER.C6 cells cotransfected with an Ad35-E1 expression construct.

Ad35 recombinant viruses escape neutralization in human serum containing neutralizing activity to Ad5 viruses.

The AdApt35.LacZ viruses were then used to investigate infection in the presence of serum that contains neutralizing activity to Ad5 viruses. Purified Ad5-based LacZ virus served as a positive control for NA. Hereto, PER.C6 cells were seeded in a wells plate at a density of $2 \times 10^5$ cells/well. The next day, a human serum sample with high neutralizing activity to Ad5 was diluted in culture medium in five steps of five times dilutions. 0.5 ml of diluted serum was then mixed with $4 \times 10^6$ virus particles AdApt5.LacZ virus in 0.5 ml medium and after 30 minutes of incubation at 37° C., 0.5 ml of the mixture was added to PER.C6 cells in duplicate. For the AdApt35.LacZ viruses, 0.5 ml of the diluted serum samples were mixed with 0.5 ml crude lysate containing AdApt35.LacZ virus and after incubation 0.5 ml of this mixture was added to PER.C6 cells in duplo. Virus samples incubated in medium without serum were used as positive controls for infection. After two hours of infection at 37° C., medium was added to reach a final volume of 1 ml and cells were further incubated. Two days after infection, cells were stained for LacZ activity. The results are shown in Table II. From these results, it is clear that whereas AdApt5.LasZ viruses are efficiently neutralized, AdApt35.LasZ viruses remain infectious irrespective of the presence of human serum. This proves that recombinant Ad3 5-based viruses escape neutralization in human sera that contain NA to Ad5-based viruses.

Example 6

Generation of Cell Lines Capable of Complementing E1-deleted Ad35 Viruses Generation of pIG135 and pIG270

Figure 13:
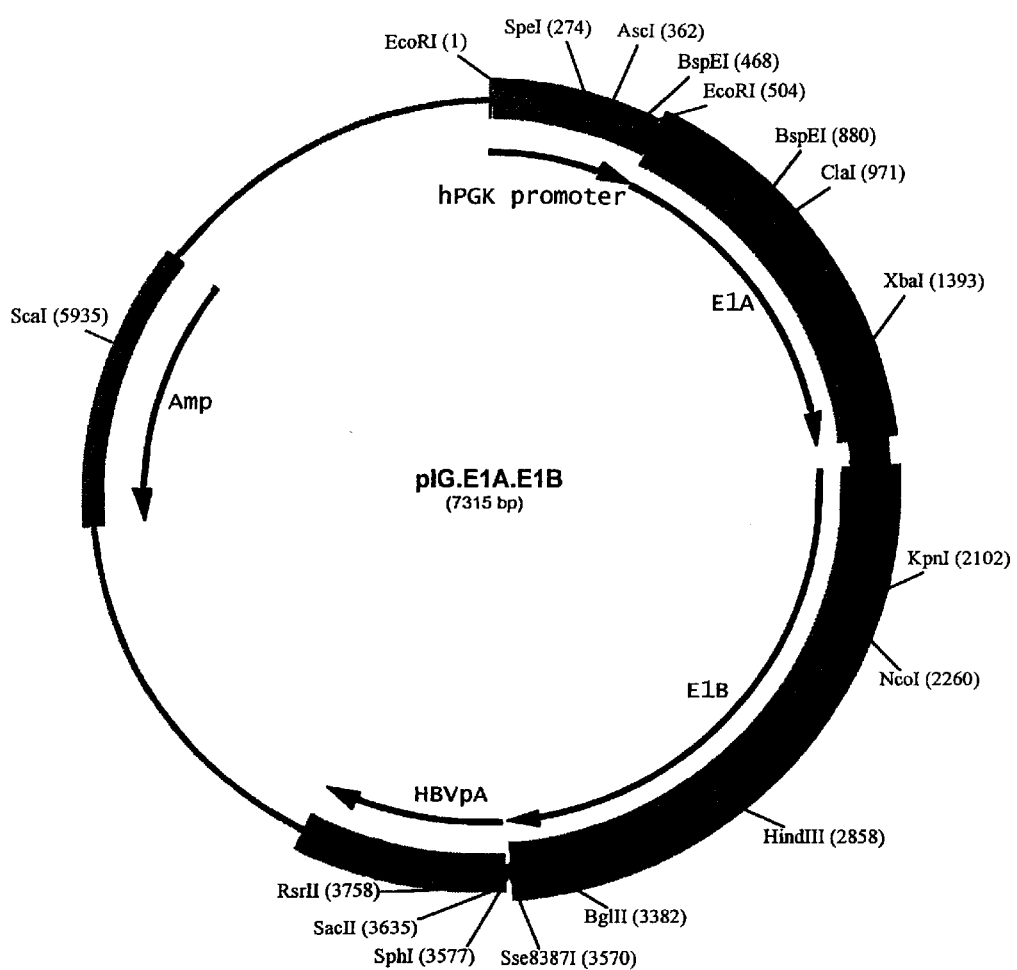
FIG. 13: Map of pIG.E1A.E1B.

Construct pIG.E1A.E1B (FIG. 13) contains E1 region sequences of Ad5 corresponding to nucleotides 459 to 3510 of the wt Ad5 sequence (Genbank accession number M72360) operatively linked to the human phosphoglycerate kinase promoter ("PGK") and the Hepatitis B Virus polyA sequences. The generation of this construct is described in International Patent Application No. WO97/00326. The E1 sequences of Ad5 were replaced by corresponding sequences of Ad35 as follows. pRSV.Ad35-E1 (described in Example 5) was digested with EcoRI and Sse8387I and the 3 kb fragment corresponding to the Ad35 E1 sequences was isolated from gel. Construct pIG.E1A.E1B was digested with Sse8387I completely and partially with EcoRI. The 4.2 kb fragment corresponding to vector sequences without the Ad5 E1 region but retaining the PGK promoter were separated from other fragments on LMP agarose gel and the correct band was excised from gel. Both obtained fragments were ligated resulting in pIG.Ad35-E1.

This vector was further modified to remove the LacZ sequences present in the pUC119 vector backbone. Hereto, the vector was digested with BsaAI and BstXI and the large fragment was isolated from gel. A double stranded oligo was prepared by annealing the following two oligos:

BB1: 5'-GTG CCT AGG CCA CGG GG-3' (SEQ ID NO: 24) and

BB2: 5'-GTG GCC TAG GCA C-3' (SEQ ID NO: 25).

Figure 14:
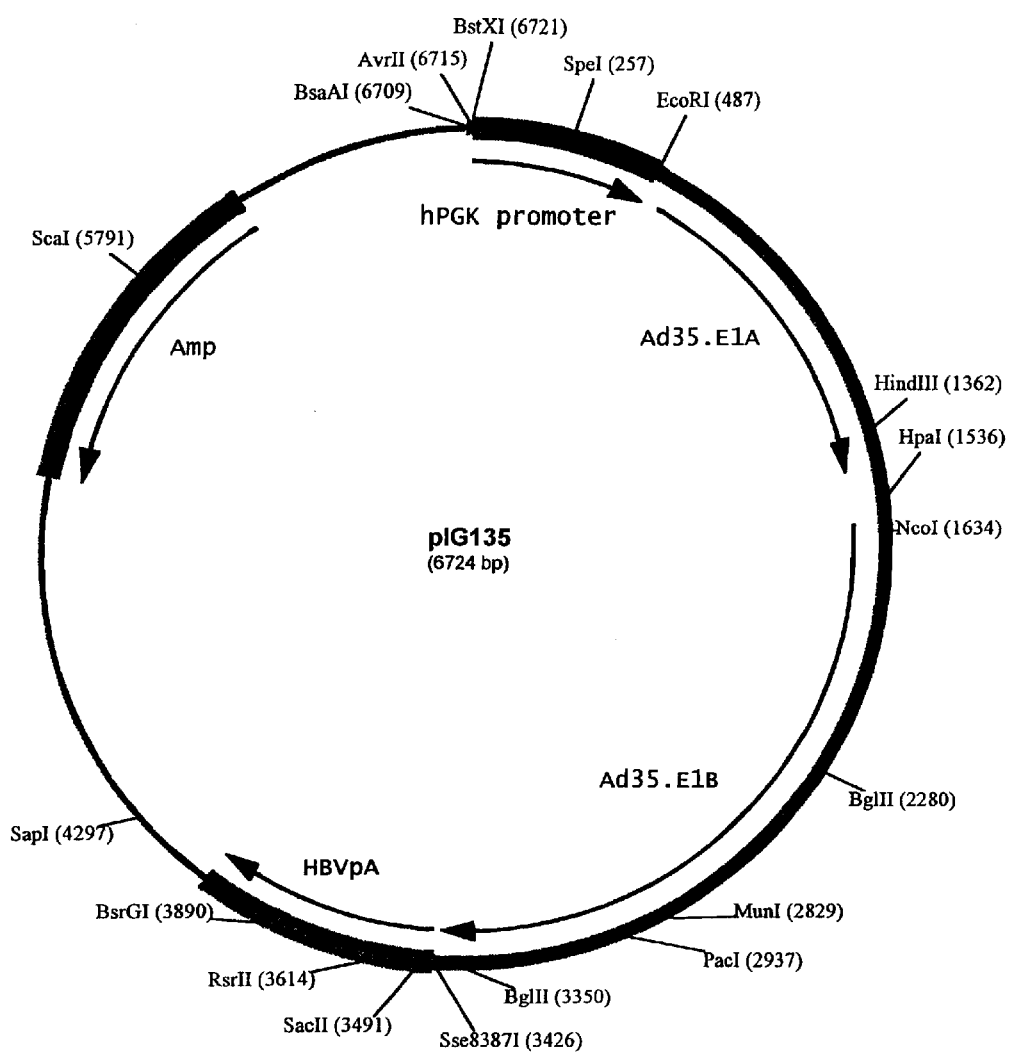
FIG. 14: Map of pIG135.

Ligation of the oligo and the vector fragment resulted in construct pIG135 (FIG. 14). Correct insertion of the oligo restores the BsaAI and BstXI sites and introduces a unique AvrII site. Next, we introduced a unique site at the 3' end of the Ad35-E1 expression cassette in pIG135. Hereto, the construct was digested with Sapi and the 3' protruding ends were made blunt by treatment with T4 DNA polymerase. The thus treated linear plasmid was further digested with BsrGI and the large vector-containing fragment was isolated from gel. To restore the 3' end of the HBVpolyA sequence and to introduce a unique site, a PCR fragment was generated using the following primers:

270F: 5'-CAC CTC TGC CTA ATC ATC TC-3' (SEQ ID NO: 26) and

270R: 5'-GCT CTA GAA ATT CCA CTG CCT TCC ACC-3' (SEQ ID NO: 27).

Figure 15:
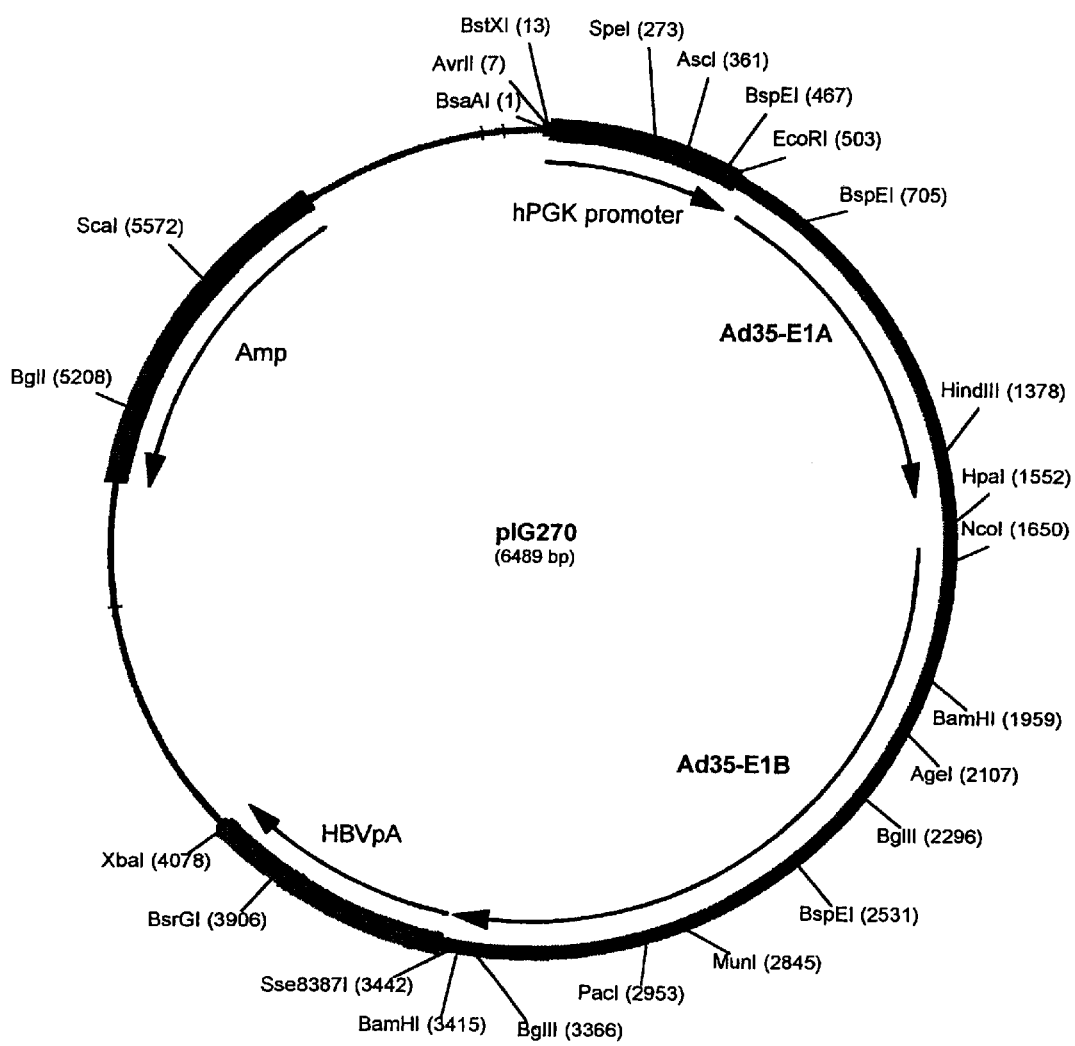
FIG. 15: Map of pIG270.

The PCR was performed on pIG.Ad35.E1 DNA using Pwo polymerase (Roche) according to the manufacturer's instructions. The obtained PCR product was digested with BsrGI and dephosphorylated using Tsap enzyme (LTI), the latter to prevent insert dimerization on the BsrGI site. The PCR fragment and the vector fragment were ligated to yield construct pIG270 (FIG. 15).

Ad35 E1 Sequences are Capable of Transforming Rat Primary Cells

New born WAG/RIJ rats were sacrificed at 1 week of gestation and kidneys were isolated. After careful removal of the capsule, kidneys were disintegrated into a single cell suspension by multiple rounds of incubation in trypsin/EDTA (LTI) at 37° C. and collection of floating cells in cold PBS containing 1% FBS. When most of the kidney was trypsinized all cells were re-suspended in DMEM supplemented with 10% FBS and filtered through a sterile cheesecloth. Baby Rat Kidney (BRK) cells obtained from one kidney were plated in 5 dishes (Greiner, 6 cm). When a confluency of 70–80% was reached, the cells were transfected with 1 or 5 μgr DNA/dish using the $CaPO_4$ precipitation kit (LTI) according to the manufacturer's instructions. The following constructs were used in separate transfections: pIG.E1A.E1B (expressing the Ad5-E1 region), pRSV.Ad35-E1, pIG.Ad35-E1 and pIG270 (expressing the Ad35-E1 region). Cells were incubated at 37° C., 5% $CO_2$ until foci of transformed cells appeared. Table III shows the number of foci that resulted from several transfection experiments using circular or linear DNA. As expected, the Ad5-E1 region efficiently transformed BRK cells. Foci also appeared in the Ad35-E1 transfected cell layer although with lower efficiency. The Ad35 transformed foci appeared at a later time point: ~2 weeks post transfection compared with 7–10 days for Ad5-E1. These experiments clearly show that the E1 genes of the B group virus Ad35 are capable of transforming primary rodent cells. This proves the functionality of the Ad35-E1 expression constructs and confirms earlier findings of the transforming capacity of the B-group viruses Ad3 and Ad7 (Dijkema, 1979). To test whether the cells in the foci were really transformed a few foci were picked and expanded. From the 7 picked foci at least 5 turned out to grow as established cell lines.

Generation of New Packaging Cells Derivedfrom Primary Human Amniocytes

Amniotic fluid obtained after amniocentesis was centrifuged and cells were re-suspended in AmnioMax medium (LTI) and cultured in tissue culture flasks at 37° C. and 10% $CO_2$. When cells were growing nicely (approximately one cell division/24 hrs.), the medium was replaced with a 1:1 mixture of AmnioMax complete medium and DMEM low glucose medium (LTI) supplemented with Glutamax I (end concentration 4 mM, LTI) and glucose (end concentration 4.5 gr/L, LTI) and 10% FBS (LTI). For transfection ~$5 \times 10^5$ cells were plated in 10 cm tissue culture dishes. The day after, cells were transfected with 20 lgr of circular pIG270/dish using the $CaPO_4$ transfection kit (LTI) according to manufacturer's instructions and cells were incubated overnight with the DNA precipitate. The following day, cells were washed 4 times with PBS to remove the precipitate and further incubated for over three weeks until foci of transformed cells appeared. Once a week the medium was replaced by fresh medium. Other transfection agents like, but not limited to, LipofectAmine (LTI) or PEI (Polyethylenimine, high molecular weight, water-free, Aldrich) were used. Of these three agents PEI reached the best transfection efficiency on primary human amniocytes: ~1% blue cells 48 hrs. Following transfection of pAdApt35.LacZ.

Foci are isolated as follows. The medium is removed and replaced by PBS after which foci are isolated by gently scraping the cells using a 50–200 μl Gilson pipette with a disposable filter tip. Cells contained in ~10 μl PBS were brought in a 96 well plate containing 15 μl trypsin/EDTA (LTI) and a single cell suspension was obtained by pipetting up and down and a short incubation at room temperature. After addition of 200 μl of the above described 1:1 mixture of AmnioMax complete medium and DMEM with supplements and 10% FBS, cells were further incubated. Clones that continued to grow were expanded and analysed their ability to complement growth of E1-deleted adenoviral vectors of different sub-groups, specifically ones derived from B-group viruses specifically from Ad35 or Ad11.

Generation of New Packaging Cell Lines from HER Cells

HER cells are isolated and cultured in DMEM medium supplemented with 10% FBS (LTI). The day before transfection, ~5×10$^5$ cells are plated in 6 cm dishes and cultured overnight at 37° C. and 10% $CO_2$. Transfection is done using the $CaPO_4$ precipitation kit (LTI) according to the manufacturer's instructions. Each dish is transfected with 8–10 μmgr pIG270DNA, either as a circular plasmid or as a purified fragment. To obtain the purified fragment, pIG270 was digested with AvrII and XbaI and the 4 kb fragment corresponding to the Ad35 E1 expression cassette was isolated from gel by agarase treatment (Roche). The following day, the precipitate is washed away carefully by four washes with sterile PBS. Then fresh medium is added and transfected cells are further cultured until foci of transformed cells appear. When large enough (>100 cells) foci are picked and brought into 96-wells as described above. Clones of transformed HER cells that continue to grow, are expanded and tested for their ability to complement growth of E1-deleted adenoviral vectors of different sub-groups specifically ones derived from B-group viruses specifically from Ad35 or Ad11.

New Packaging Cell Lines Derived from PER.C6

As described in Example 5, it is possible to generate and grow Ad35 E1-deleted viruses on PER.C6 cells with cotransfection of an Ad35-E1 expression construct, e.g. pRSV.Ad35.E1. However, large-scale production of recombinant adenoviruses using this method is cumbersome because, for each amplification step, a transfection of the Ad35-E1 construct is needed. In addition, this method increases the risk of non-homologous recombination between the plasmid and the virus genome with high chances of generation of recombinant viruses that incorporate E1 sequences resulting in replication competent viruses. To avoid this, the expression of Ad35-E1 proteins in PER.C6 has to be mediated by integrated copies of the expression plasmid in the genome. Since PER.C6 cells are already transformed and express Ad5-E1 proteins, addition of extra Ad35-E1 expression may be toxic for the cells, however, it is not impossible to stably transfect transformed cells with E1 proteins since Ad5-E1 expressing A549 cells have been generated.

Figure 16:
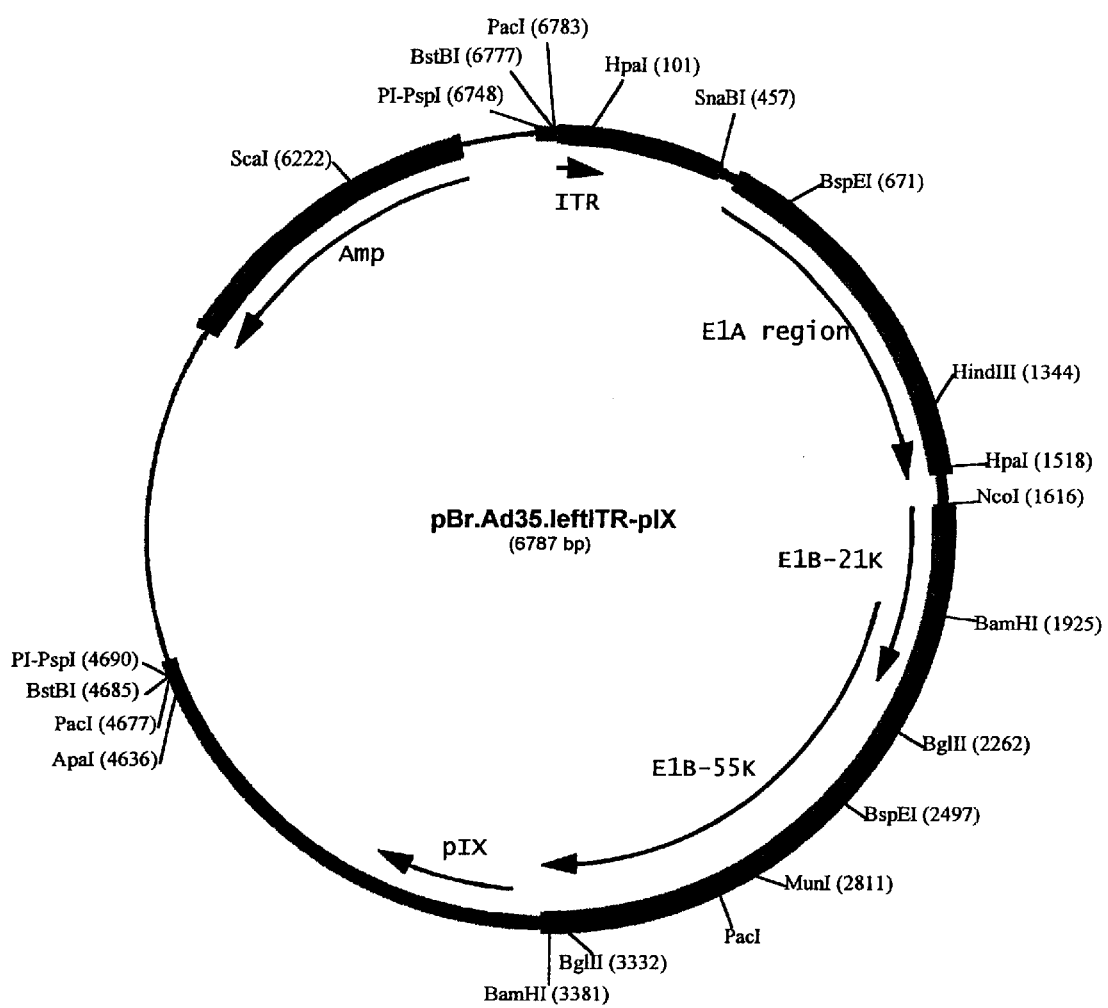
FIG. 16: Map of pBr.Ad35.leftITR-pIX.
Figure 17:
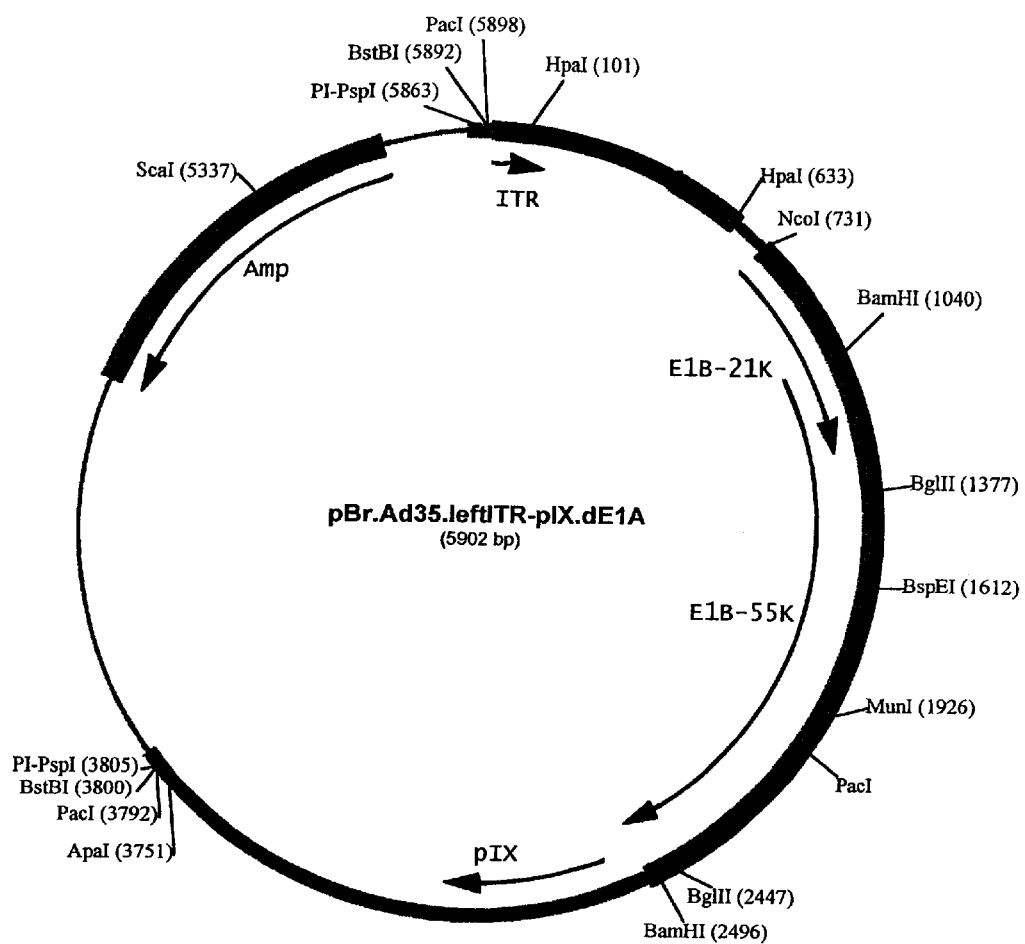
FIG. 17: Map of pBr.Ad35.leftITR-pIXΔE1A.

In an attempt to generate recombinant adenoviruses derived from subgroup B virus Ad7, Abrahamsen et al. (1997) were not able to generate E1-deleted viruses on 293 cells without contamination of wt Ad7. Viruses that were picked after plaque purification on 293-ORF6 cells (Brough et al., 1996) were shown to have incorporated Ad7 E1B sequences by non-homologous recombination. Thus, efficient propagation of Ad7 recombinant viruses proved possible only in the presence of Ad7-E1B expression and Ad5-E4-ORF6 expression. The E1B proteins are known to interact with cellular as well as viral proteins (Bridge et al., 1993; White, 1995). Possibly, the complex formed between the E1B 55K protein and E4-ORF6 which is necessary to increase mRNA export of viral proteins and to inhibit export of most cellular mRNAs, is critical and in some way serotype specific. The above experiments suggest that the E1A proteins of Ad5 are capable of complementing an Ad7-E1A deletion and that Ad7-E1B expression in adenovirus packaging cells on itself is not enough to generate a stable complementing cell line. To test whether one or both of the Ad35-E1B proteins is/are the limiting factor in efficient Ad35 vector propagation on PER.C6 cells, we have generated an Ad35 adapter plasmid that does contain the E1B promoter and E1B sequences but lacks the promoter and the coding region for E1A. Hereto, the left end of wtAd35 DNA was amplified using the primers 35F1 and 35R4 (both described in Example 4) with Pwo DNA polymerase (Roche) according to the manufacturer's instructions. The 4.6 kb PCR product was purified using the PCR purification kit (LTI) and digested with SnaBI and ApaI enzymes. The resulting 4.2 kb fragment was then purified from gel using the QIAExII kit (Qiagen). Next, pAdApt35IP1 (Example 4) was digested with SnaBI and ApaI and the 2.6 kb vector-containing fragment was isolated from gel using the GeneClean kit (BIO 101, Inc). Both isolated fragments were ligated to give pBr/Ad35.leftITR-pIX (FIG. 16). Correct amplification during PCR was verified by a functionality test as follows: The DNA was digested with BstBI to liberate the Ad35 insert from vector sequences and 4 μg of this DNA was co-transfected with 4 μg of NotI digested pWE/Ad35.pIX-rITR (Example 4) into PER.C6 cells. The transfected cells were passaged to T80 flasks at day 2 and again two days later CPE had formed showing that the new pBr/Ad35.leftITR-pIX construct contains functional E1 sequences. The pBr/Ad35.leftITR-pIX construct was then further modified as follows. The DNA was digested with SnaBI and HindII and the 5' HindII overhang was filled in using Klenow enzyme. Religation of the digested DNA and transformation into competent cells (LTI) gave construct pBr/Ad35leftITR-pIXΔDE1A (FIG. 17). This latter construct contains the left end 4.6 kb of Ad35 except for E1A sequences between bp 450 and 1341 (numbering according to wtAd35, FIG. 5) and thus lacks the E1A promoter and most of the E1A coding sequences. pBr/Ad35.leftITR-pIXΔDE1A was then digested with BstBI and 2 μg of this construct was co-transfected with 6 μmgr of NotI digested pWE/Ad35.pIX-rITR (Example4) into PER.C6 cells. One week following transfection full CPE had formed in the transfected flasks.

This experiment shows that the Ad35-E1A proteins are functionally complemented by Ad5-E1A expression in PER.C6 cells and that at least one of the Ad35-E1B proteins cannot be complemented by Ad5-E1 expression in PER.C6. It further shows that it is possible to make a complementing cell line for Ad35 E1-deleted viruses by expressing Ad35-E1B proteins in PER.C6. Stable expression of Ad35-E1B sequences from integrated copies in the genome of PER.C6 cells may be driven by the E1B promoter and terminated by a heterologous poly-adenylation signal like, but not limited to, the HBVpA. The heterologous pA signal is necessary to avoid overlap between the E1B insert and the recombinant vector, since the natural E1B termination is located in the pIX transcription unit that has to be present on the adenoviral vector. Alternatively, the E1B sequences may be driven by a heterologous promoter like, but not limited to the human PGK promoter or by an inducible promoter like, but not limited to the 7xtetO promoter (Gossen and Bujard, 1992). Also in these cases the transcription termination is mediated by a heterologous pA sequence, e.g. the HBV pA. The Ad35-E1B sequences at least comprise one of the coding regions of the E1B 21K and the E1B 55K proteins located between nucleotides 1611 and 3400 of the wt Ad35 sequence. The insert may also include (part of the) Ad35-E1B sequences between nucleotides 1550 and 1611 of the wt Ad35 sequence.

Example 7

Ad35-based Viruses Deleted for E1A and E1B-21K Genes Efficiently Propagate on Ad5 Complementing Cell Lines The generation of Ad35-based viruses that are deleted for E1A and retain the full E1B region is described in Example 6 of this application. Such viruses can be generated and propagated on the Ad5 complementing cell line PER.C6. The E1B region comprises partially overlapping coding sequences for the two major proteins 21K and 55K (Bos et al., 1981). Whereas during productive wt adenoviral infection both 21K and 55K are involved in counteracting the apoptose-inducing effects of E1A proteins, the E1B 55K protein has been suggested to have additional functions during the late phase of virus infection. These include the accumulation of viral mRNAs, the control of late viral gene expression and the shutoff of most host mRNAs at the level of mRNA transport (Babiss et al., 1984, 1985; Pilder et al., 1986). A complex formed between E1B-55K and the ORF6 protein encoded by the adenovirus early region 4 (Leppard and Shenk, 1989; Bridge and Ketner, 1990) exerts at least part of these functions.

To analyze which of the E1B proteins is required for propagation of Ad35-E1A deleted recombinant viruses on PER.C6 packaging cells, the E1B region in construct pBr.Ad35.leftITR-pIXΔE1A (see Example 6 and FIG. 17) was further deleted. A first construct, pBr.Ad35Δ21K, retains the full E1B-55K sequence and is deleted for E1A and E1B-21K. Hereto. pBr.Ad35.leftITR-pIXΔE1A was digested with NcoI and BspEI and the 5 KB vector fragment was isolated from agarose gel using the geneclean kit (BIO 101, Inc.) according to the manufacturer's instructions. Then a PCR fragment was generated with pBr.Ad35.leftITR-pIXΔE1A as template DNA using the following primers:

35D21: 5'-TTA GAT CCA TGG ATC CCG CAG ACT C-3' (SEQ ID NO: 28) and

35B3: 5'-CCT CAG CCC CAT TTC CAG-3' (SEQ ID NO: 29).

Amplifacation was done using Pwo DNA polymerase (Roche) according to manufacturer's recommendations with the addition of DMSO (fmal concentration 3%) in the reaction mixture. The PCR program was as follows: 94° C. for 2', then 30 cycles of 94° C. for 30", 58° C. for and 72° C. for 45"and a final step at 68° C. for 8' to ensure blunt ends.

Figure 18:
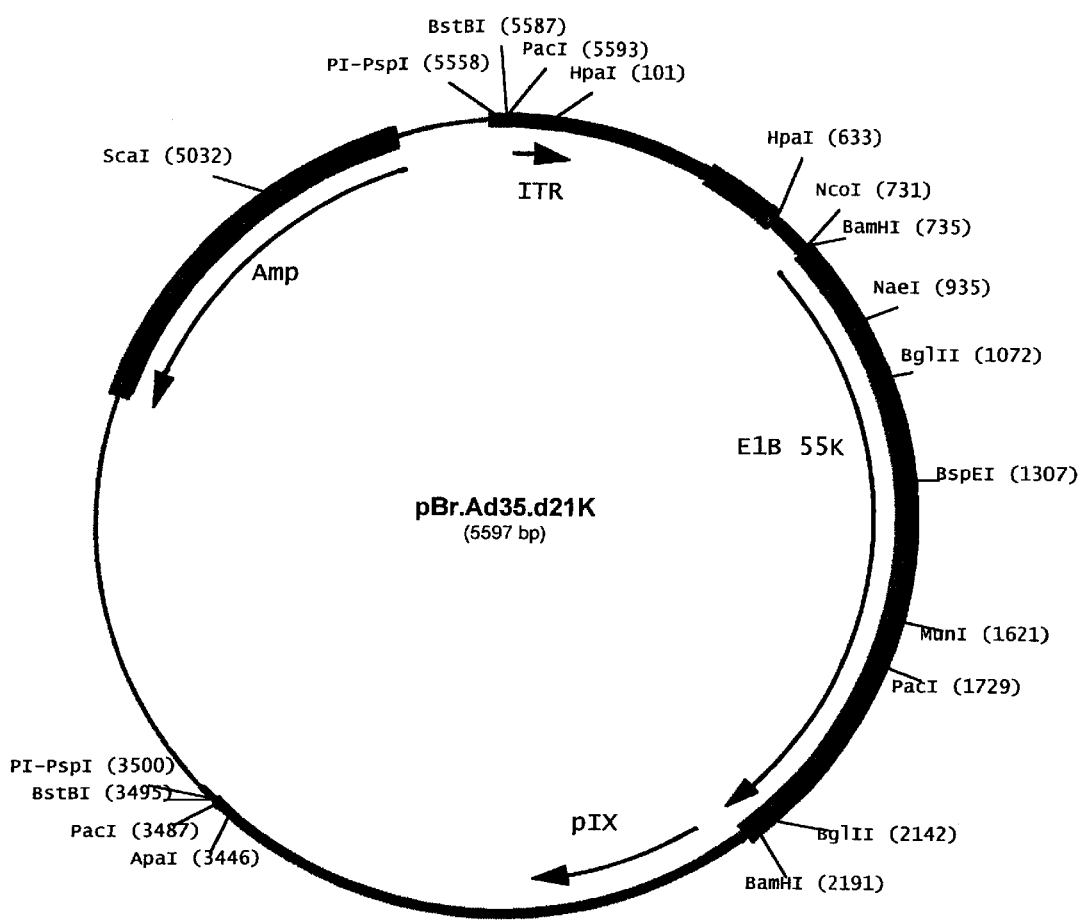
FIG. 18: Map of pBr.Ad35.Δ21K.

This PCR amplifies Ad35-E1B sequences from nucl. 1908 to 2528 (sequence Ad35, FIG. 5) and introduces an NcoI site at the start codon of the E1B-55K coding sequence (bold in primer 35D21). The 620 bp PCR fragment was purified using the PCR purification kit (Qiagen) and then digested with NcoI and BspEI, purified from agarose gel as above and ligated to the above described NcoI/BspEI digested vector fragment to give pBr.Ad35Δ21K (FIG. 18).

Figure 19:
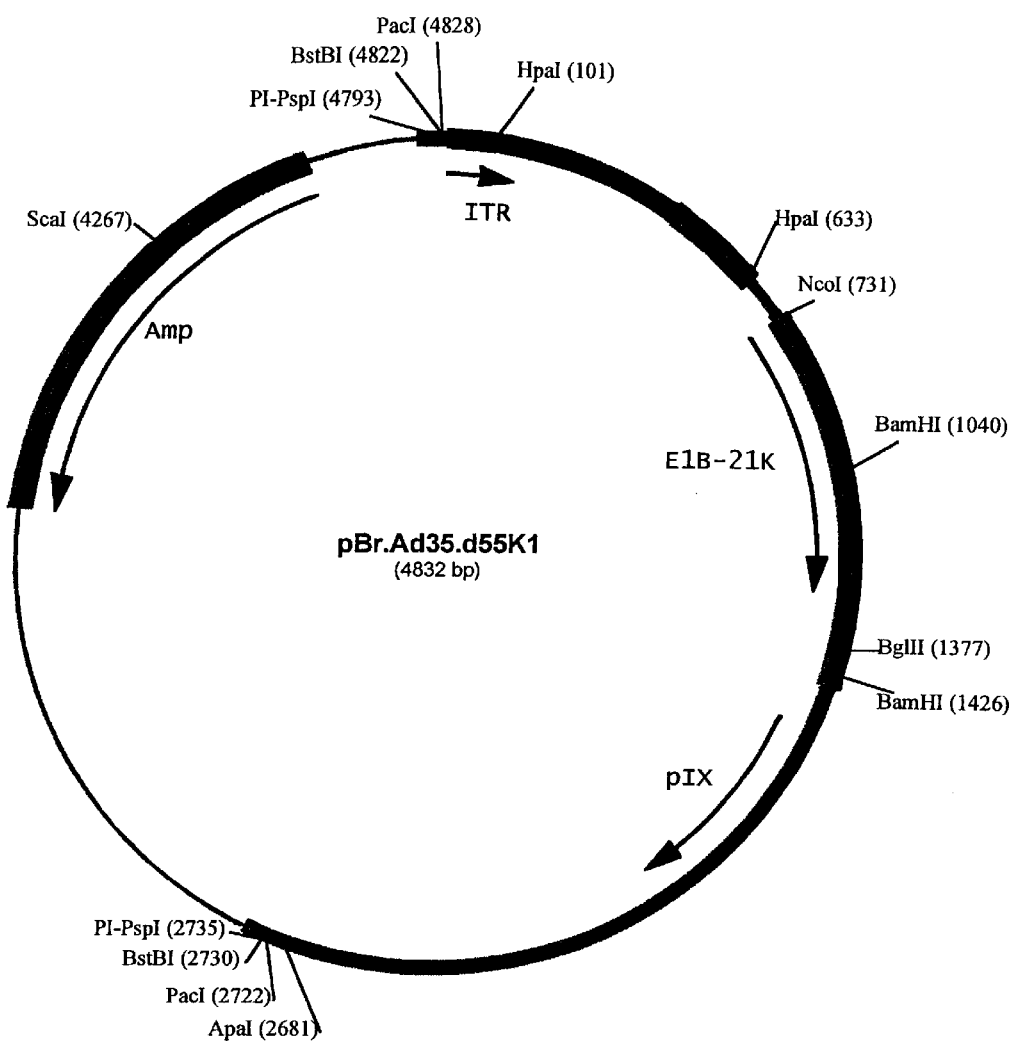
FIG. 19: Map of pBr.Ad35.Δ55K1.

Since the coding regions of the 21K and 55K proteins overlap, it is only possible delete part of the 55K coding sequences while retaining 21K. Hereto, pBr.Ad35.leftITR-pIXΔTE1A was digested with BglII and the vector fragment was religated to give pBr.Ad35Δ55K1 (FIG. 19). This deletion removes E1B coding sequences from nucl. 2261 to 3330 (Ad35 sequence in FIG. 5). In this construct the N-terminal 115 amino acids are retained and become fused to 21 additional amino acids out of the proper reading frame before a stop codon is encountered. The 21K coding region is intact in construct pBr.Ad35Δ55K1.

Figure 20:
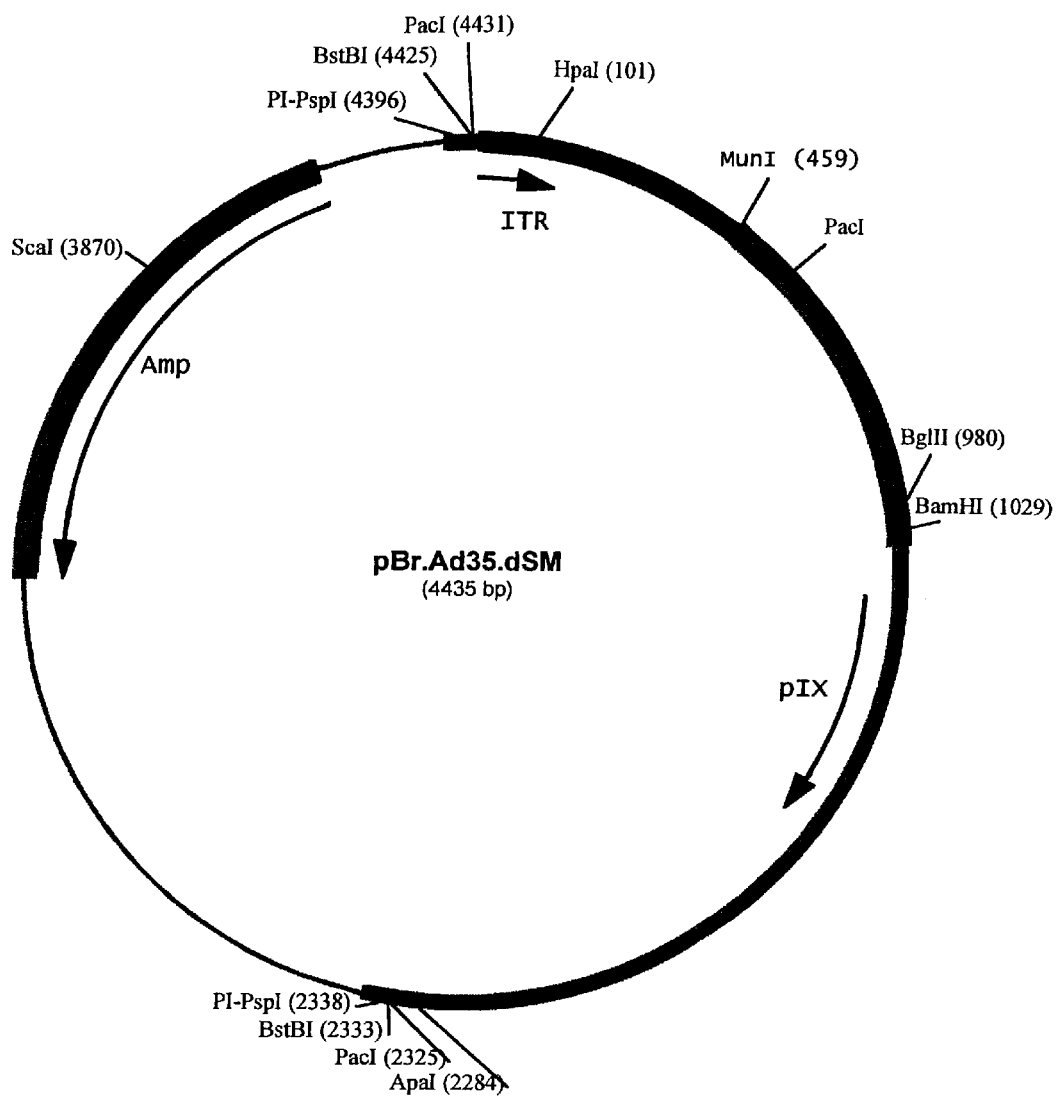
FIG. 20: Map of pBrAd35ΔSM
Figure 21:
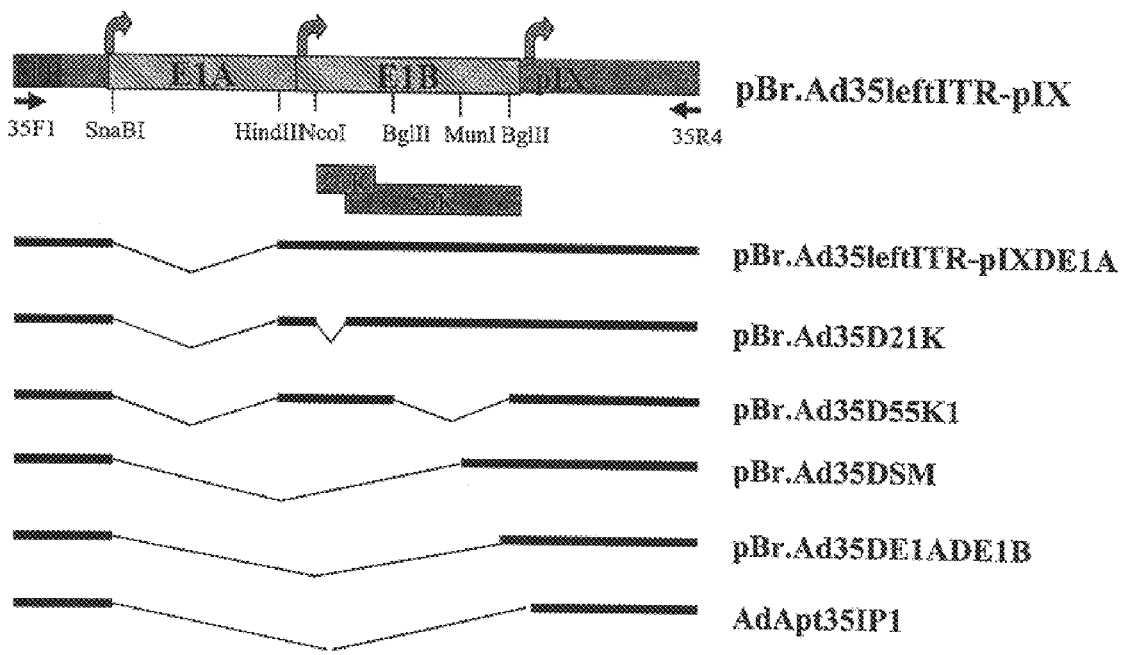
FIG. 21: Schematic representation of Ad35-E1A/E1B deletion constructs.

A third construct that has a deletion of E1A, 21K and most of the 55K sequences was generated as follows. pBr.Ad35.leftITR-pIX (FIG. 16) was digested with SnaBI and MfeI (isoschizomer of MunI) and the 5' overhang resulting from the MfeI digestion was filled in using Klenow enzyme. The 4.4 kb vector fragment was isolated from gel using the geneclean kit (Bio 101, Inc.) according to the manufacturer's instructions and religated to give construct pBr.Ad35AsM (FIG. 20). In this construct, the Ad35 sequences between nucl. 453 and 2804 are deleted thus 596 nucl. of the 3' end of E1b-55K are retained. A further deletion of 55K sequences was made in construct pBr.Ad35AE1A. AE1B by digestion of pBr.Ad35.leftITR-pIX with SnaBI and BglII, Klenow treatment to fill in the BglII cohesive ends, and religation. FIG. 21 shows a schematic representation of the above mentioned constructs.

To test whether Ad35-based viruses can be generated with these constructs, each of the constructs was cotransfected with NotI digested pWE.Ad35pIX-rITR (see Example 4) onto PER.C6 cells. Hereto, the respective fragments were PCR amplified using primers 35F1 and 35R4 (see, Example 4). This PCR amplification was done since some of the constructs were difficult to isolate in large enough quantities. In this way, equal quality of the different adapter fragments was ensured. For the amplification Pwo DNA polymerase (Roche) was used according to the manufacturer's instructions but with DMSO (3% final concentration)added to the PCR mixture. Of each template ~50 ng DNA was used. The conditions for the PCR were as follows: 94° C. for 2', then 5 cycles of 94° C. for 30", 48° C. for 45" and 72° C. for 4' followed by 25 cycles of 94° C. for 30", 60° C. for 30" and 72° C. for 4' and a final step at 68° C. for 8'. PCR fragments were generated from pBr.Ad35leftITR-pIX, pBr.Ad35.leftITR-pIXΔE1A, pBr.Ad35Δ21K, pBr.Ad35Δ55K1, pBr.Ad35ASM and pBr.Ad35ΔE1AΔE1B. All fragments were using the PCR purification kit (Qiagen) according to manufacturer's instructions and final concentrations were estimated on EtBr stained agarose gel using the Eagle Eye II Still Video system and EagleSight software (Stratagene) with the SmartLadder molecular weight marker (Eurogentec) as reference.

PER.C6 cells were seeded at a density of $2.5 \times 10^6$ cells in a T25 culturing flask in DMEM containing 10% fetal calf serum (FCS) and 10 mM $MgSO_4$ and cultured in a humidified stove at 37° C., 10% $CO_2$. The next day, 3 mg of each of the PCR fragments was cotransfected with 5 μgr NotI digested pWE.Ad35pIX-rITR using LipofectAmine (GIBCO, Life Technologies Inc.) according to the manufacturer's instructions. Two days after the transfection, all cells were passed to a T80 flask and further cultured. Cultures were then monitored for the appearance of CPE. In line with the outcome of previous experiments described in Examples 4 and 6, pBr.Ad35.leftITR-pIX and pBr.Ad35.leftITR-pIXΔE1A showed almost full CPE within one week following transfection. Of the fragments with different E1B deletions only pBr.Ad35Δ21K showed CPE at the same time as the above two fragments. Constructs pBr.Ad35Δ55K1, pBr.Ad35ΔSM and pEr.Ad35ΔE1AΔE1B did not give CPE at all, also not after harvesting by freeze-thawing and re-infection of the crude lysate onto fresh PER.C6 cells.

From these experiments, it can be concluded that Ad35-E1B-55K, and not E1B-21K, is necessary for generation and propagation of Ad35-based viruses on Ad5 complementing cell lines. Therefore, Ad35-based viruses having a deletion of the E1A and E1B 21K genes and having the E1B-55K gene or a functional fragment thereof, can be grown on Ad5 complementing cell lines. Alternatively, Ad35-based viruses can be grown on PER.C6 cells that stably express the full E1B region or the E1B-55K gene or a functional fragment thereof The Ad35 E1B-55K gene or functional parts thereof may be expressed from a heterologous promoter, like, but not limited to, the human PGK promoter, the human cytomegalovirus immediate early promoter (CMV), Rous sarcoma virus promoter, etc. and terminated by a heterologous poly adenylation sequence (pA), like but not limited to the hepatitis B virus poly adenylation sequence (HBVpA), the Simian Virus 40 poly adenylation sequence (SV40pA), etc.

As non-limiting examples PER.C6 cells that express the Ad35-E1B region driven by the E1B promoter and HBVpA, PER.C6 cells that express the Ad35-E1B region driven by the human PGK promoter and HBVpA and PER.C6 cells that express a functional fragment of Ad35 E1B-55K driven by the human PGK promoter and HBVpA are described below.

Generation of pIG35BL and pIG35BS

Figure 22:
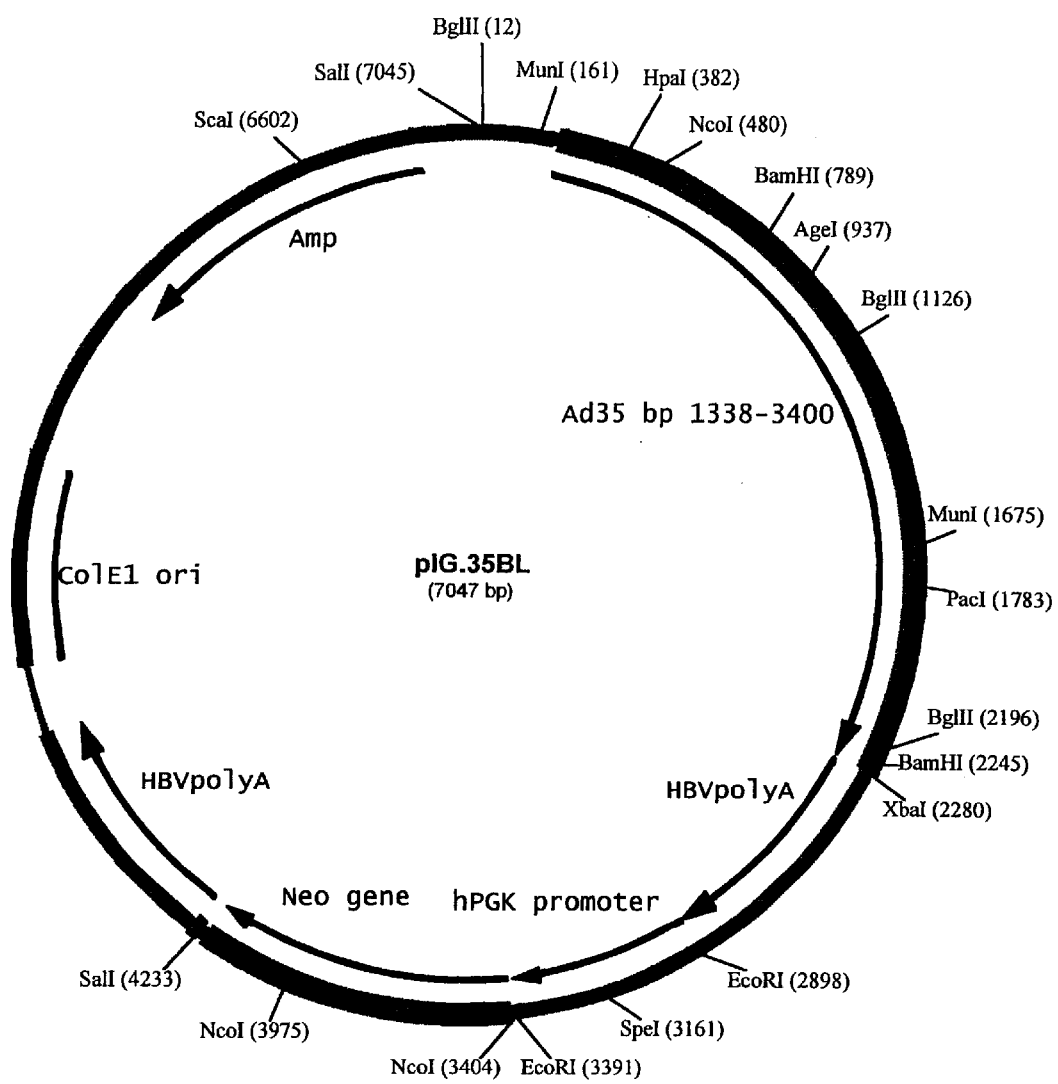
FIG. 22: Map of pIG.35BL.

We describe the generation of two expression constructs, pIG.35BS and pIG.35BL, that both carry the Ad35-E1B genes and a neomycin selection marker. The two constructs differ in the length of the fragment containing the E1B promoter. In 35BL the promoter fragment is longer and includes the 3' end of the E1A region (103 nucl. coding sequence and pA). The E1B region is terminated by the HBVpolyA, the neor gene fragment on gel and isolated using the geneclean kit (BIO 101, Inc.). After religation of pIG.35BL was made as follows. Construct pRSV.Ad35E1 (described in Example 5, FIG. 9) was digested with NruI and HindII and the protruding ends were filled in by Klenow treatment. The 7 kb vector fragment was separated from the smaller fragment on gel and isolated using the geneclean kit (BIO 101, Inc.). After religation of the DNA and transformation into competent STBL2 cells (Gibco, LTI) correct clones were isolated. pIG.35BL (FIG. 22) contains 273 nucl. upstream of the start site of the E1B-21K coding region.

pIG.35BS was made in the same way as pIG.35BL except that pRSV.Ad35E1 was digested with NruI and HpaI (both enzymes leave blunt ends), resulting in a shorter fragment upstream of the coding region of E1B-21K: 97 nucleotides.

To generate Ad35-E1B expressing cells, PER.C6 cells were seeded in 10 cm dishes at 1×10⁶ cells/dish. Two days later cells were transfected with ScaI linearised constructs. Four dishes were transfected with 1 and four with 2 μg DNA (total of 16 dishes; Lipofectamine (Gibco, LTI), no carrier DNA used) according to the manufacturer's instructions. The next day, transfected cells received G418-containing medium (0.75 mg/ml). Control transfections using LacZ expression constructs (2 μg) were stained after 48 hrs and showed a transfection efficiency of ~25%. Four days following addition of selection medium untransfected cells started to die and again three days leater clones were becoming visible. A week later, the first clones wew picked. Transfection with 1 μg resulted in less and also initially smaller clones (total ~20 clones/dish against >50 clones/dish for the transfection with 2 μg DNA). The positive control transfection using 2 μg pcDNA3 (Invitrogen) resulted in ~50 clones.

In total, 120 clones were picked and 107 were succesfully established (55 from pIG35BS and 52 from pIG35BL).

Figure 23:
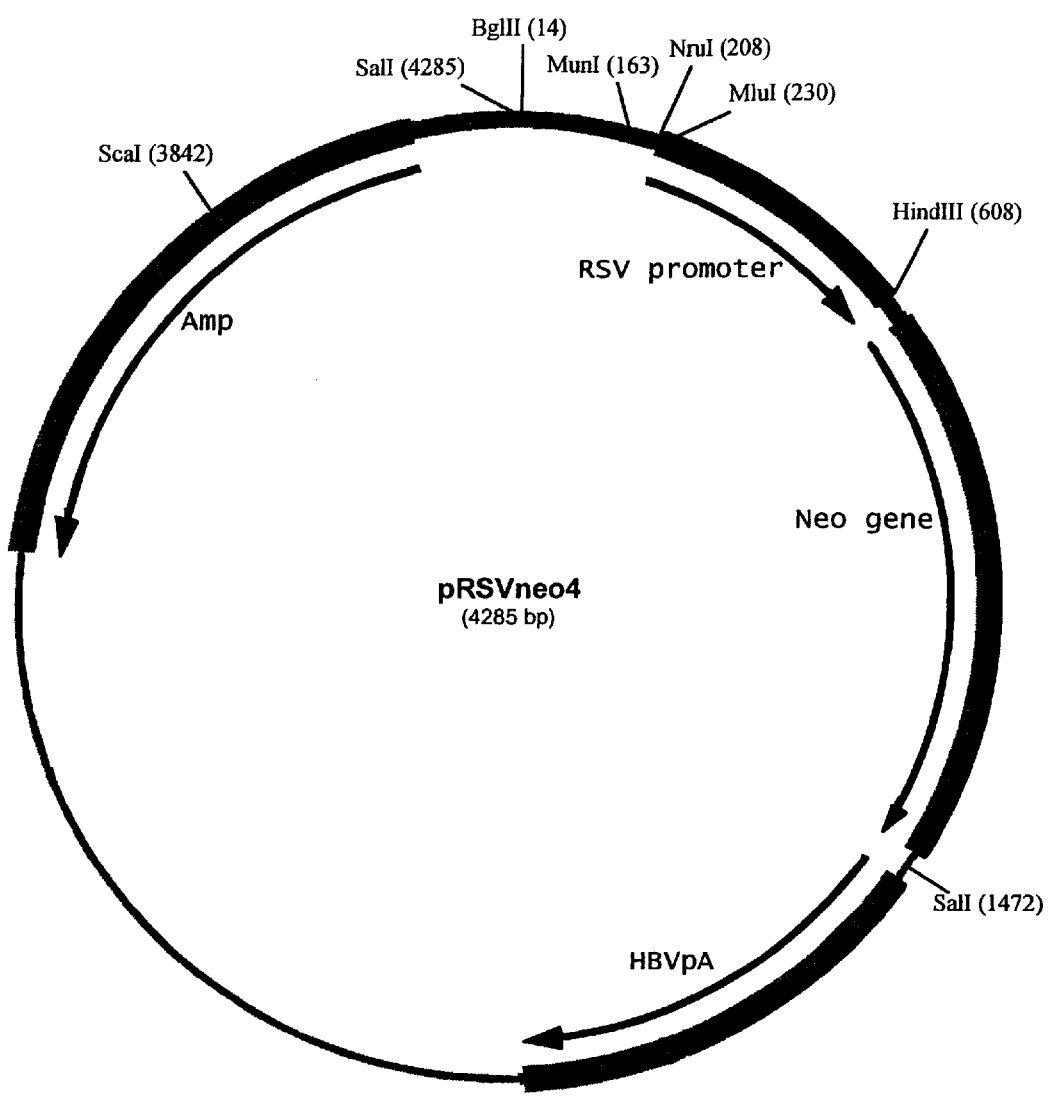
FIG. 23: Map of pRSVneo4.
Figure 24:
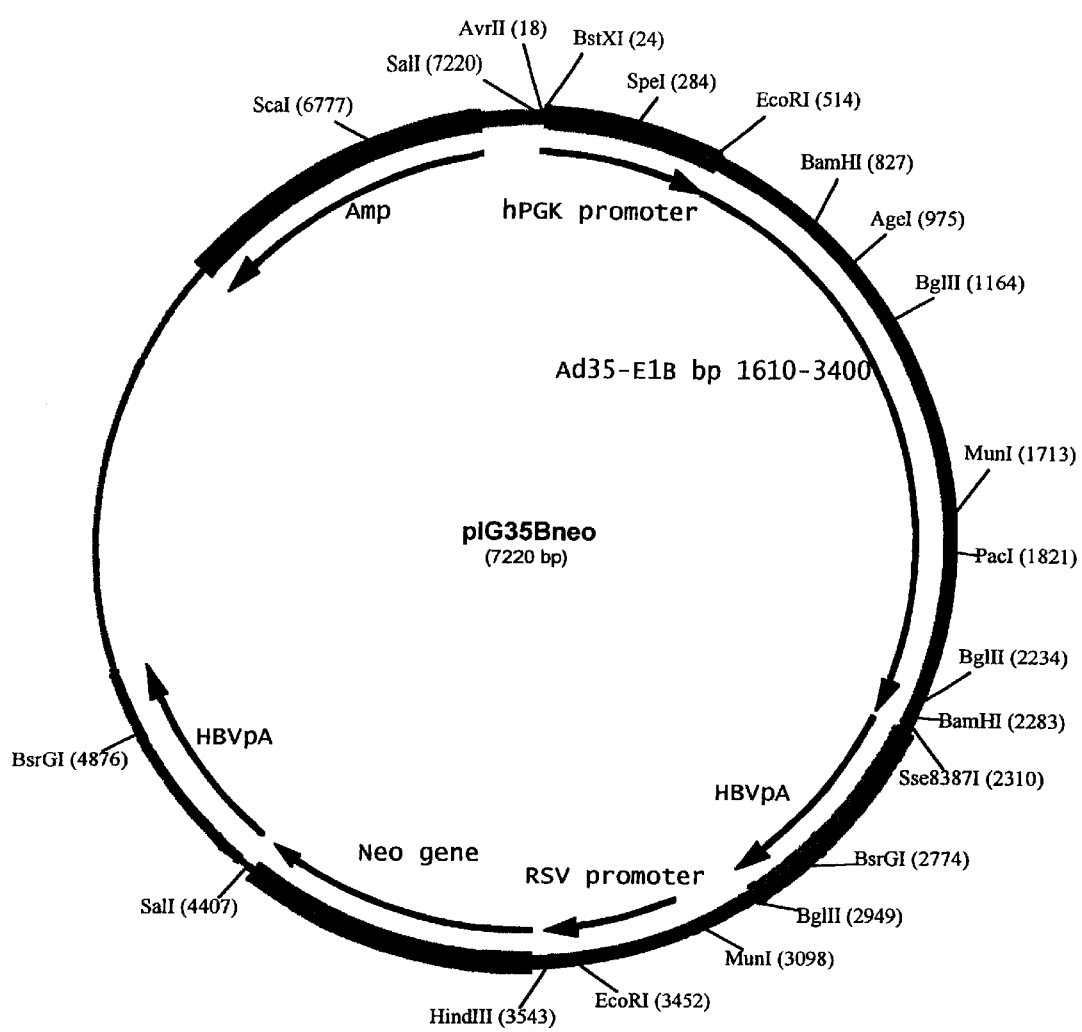
FIG. 24: Map of pIG35Bneo.

Generation of pIG35Bneo pIG35Bneo is an Ad35-E1B expression plasmid from which the E1B with ScaI and BamHI and protruding ends were filled in using Klenow enzyme. The 1070 bp fragment containing part of the Ampicilin gene and the RSV promoter was isolated from gel using the geneclean kit (BIO 101, Inc.). Next, pRSVhbvNeo was digested with To achieve this, construct pRSVhbv.Neo (described in Example 5, FIG. 12) was digested with ScaI and BamHI and protruding ends were filled in using Klenow enzyme. The 1070 were then ligated to give pRSVneo4 (FIG. 23). Construct pIG270 (FIG. 15, described in from gel using the geneclean kit (BIO 101, Inc.). Next, pRSVhbvNeo was digested with ScaI and EcoRI, blunted with Klenow and the 3.2 kb fragment containing the neo gene, above and religated to give pIG270delE1A. This construct was digested with AvrII and were then ligated to give pRSVneo4 (FIG. 23). Construct pIG270 (FIG. 15, described in Example 6) was then digested with EcoRI and NcoI and sticky ends were blunted with Next, pRSVneo4 was digested with BglII, blunted with Klenow enzyme, above and religated to give pIG270delE1A. This construct was digested with AvrII and XbaI and protruding ends were filled in using Klenow enzyme. The 2.9 kb fragment containing the hPGK promoter and Ad35.E1B sequences was isolated from gel as above. Next, pRSVneo4 was digested with BglII, blunted with Klenow enzyme, dephosphorylated and isolated from gel. The blunted AvrII/XbaI Ad35.E1B fragment was then ligated with the above prepared pRSVneo4 vector fragment and resulting clones site at nucl 2949 in FIG. 24). was choosen and named pIG35Bneo (FIG. 24). Detailed analysis of this clone revealed coding region of Ad35.E1B-21K. Hereto, both the E1A and E1B-21K sequences are first site at nucl 2949 in FIG. 24).

Generation of pIG35.55K

Construct pIG35.55K is similar to pIG35Bneo, however, it lacks the coding region of Ad35.E1B-21K. Hereto, both the E1A and E1B-21K sequences are first deleted from pIG270 as follows:

Construct pIG270 is digested with EcoRI, treated with Klenow enzyme and purified using the PCR purification kit (Qiagen) according to the manufacturer's instructions. The recovered DNA is then digested with AgeI and the ~5 kb vector fragment was isolated from gel as above. Next, Ad35 E1B-55K sequences sre amplified by PCR on pIG270 template DNA using the following primers:

35D21: 5'-TTA GAT CCA TGG ATC CCG CAG ACT C-3' (SEQ ID NO: 30) and

35B3: 5'-CCT CAG CCC CAT TTC CAG-3' (SEQ ID NO: 31).

Figure 25:
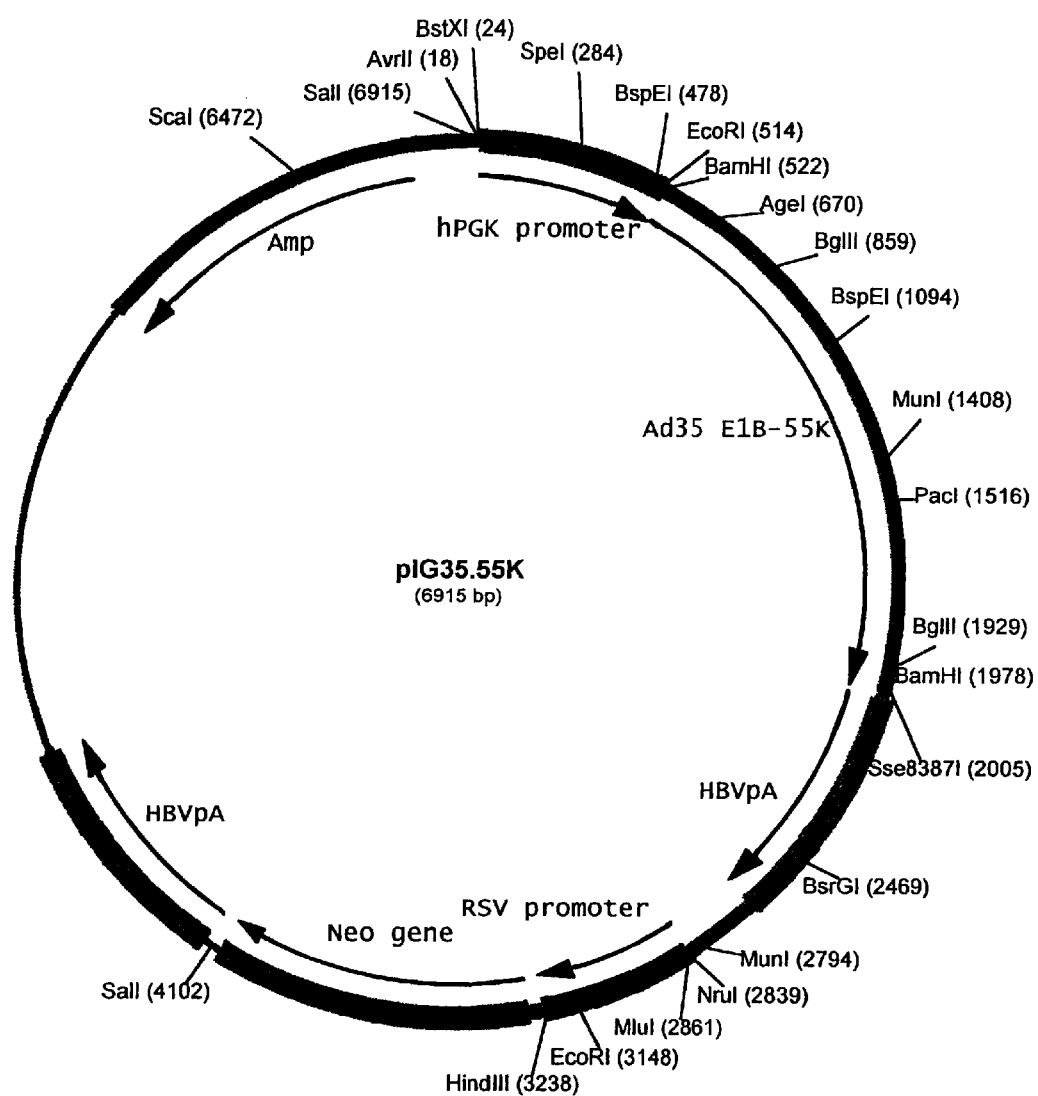
FIG. 25: Map of pIG35.55K

The conditions used for the amplification are as previously described. The PCR fragment is purified using the PCR purification kit (Qiagen) and digested with NcoI. Following Klenow treatment to fill in the protruding ends, the DNA is forther sigested with AgeI and again column purified. The thus treated PRC fragment is then cloned into the above prepared EcoRI/AgeI digested vector fragment to give pIG270.ΔE1AΔ21K. The last steps to obtain pIG35.55K (FIG. 25) are equivalent to the last steps described above for the generation of pIG35Bneo starting with pIG270.ΔE1AΔ21K instead of pIG270.ΔE1A.

pIG35.55K is then linearized with ScaI and used to transfect PER.C6 cells as described above. Clones that are resistent to G418 selection are picked and analysed for their ability to complement the propagation of E1-deleted Ad35 viruses.

Example 8

New packaging cell lines for the generation and propagation of E1-deleted Ad35-based vectors derived from primary human cells.

The complete morphological transformation of primary cells by adenovirus E1 genes is the result of the combined activities of the proteins encoded by the E1A and E1B regions. The roles of the differint E1 proteins encoded by the transformation have been studied extensively (reviewed in Zantema and van der Ed, 1995; White, 1995, 1996). The adenovirus E1A proteins are essential for transformation of primary cells. The E1A proteins exert this effect through direct interaction with a number of cellular proteins that are involved in regulation of transcription. These include the pRB family of proteins, p300/CBP and TATA binding protein. In addition to this E1A increases the level of p53 protein in the cells. In the absence of adenovirus E1B activity the rise in p53 levels leads to the induction of apoptosis. Both proteins encoded by the E1B region counteract the induction of apoptosis although by different mechanisms. E1B-21K seems to counteract apoptosis in a manner similar to Bcl-2 via interaction with the effector proteins downstream in the apoptosis pathway (Han et al., 1996), whereas E1B-55K fuictions through direct interaction with p53. Importantly, the molecular mechanism by which the E1B-55K proteins of Ad2 and 5 (subgroup C) and Ad12 (subgroup A) function in the ability to neutralise p53 may differ. Whereas Ad5 E1B-55K binds p53 strongly and the complex localises to the cytoplasm, Ad12 E1B-55K binds p53 weakly and both proteins are localised in the nucleus (Zantema et al., 1985; Grand et al., 1999). Both proteins, however, inhibit the transactivation of other genes by p53 (Yew and Berk, 1992).

In rodent cells, the activity of E1A together with either E1B-21K or 55K is sufficient for full transformation although expression of both E1B proteins together is twice as efficient (Rao et al., 1992;). In human cells however, the activity of the E1B-55K protein seems to be more important given the observation that E1B-55K is indispensible for the establishment of transformed cells (Gallimore, 1986).

Example 6 hereof describes the generation of pIG270. In this construct the Ad35-E1 genes are expressed from the hPGK promoter and transcription is terminated by fragment of the Hepatitis B virus genome (Simonsen and Levinson, 1983; see also sequence described by Singer-Sam et al. (1984). The HBVpA is located in a BamHI-BglII fragment of the Hepatitis B virus genome (Simonsen and Levinson, 1983; see also Genbank HBV-AF090841). As mentioned before, the promoter and polyadenylation sequences of the E1 expression constructs described in this invention may be derived from other sources without departing from the invention. Also, other functional fragments of the hPGK and HbVpA sequences mentioned above may be used.

The functionality of pIG270 was shown by transformation of primary Baby Rat Kidney cells (BRK). Comparison with an equivalent Ad5-E1 expression construct learned that Ad35-E1 genes were less efficient in transforming these cells. The same has been found for the E1 genes of Ad12 (Bemards et al., 1982).

It is unclear which E1 protein(s) determine(s) the difference in subgroups. In the case of Ad12, transfection studies with chimeric E1A/E1B genes proteins (Bemards et al., 1982). The E1B-55K protein is shown infra to contain serotype-specific functions necessary for complementation of E1-deleted adenoviruses. If function, it is unlikely that these are involved in the transformation efficiency.

Analysis of functional domains in the Ad2 or Ad5 E1B-55K proteins using insertion mutants have revealed that functions related to viral replication, late protein synthesis and host protein shut-off are not confined to specific domains but are distributed along the protein (Yew et al., 1990). Using the same set of mutants, the domains important for interaction with p53 and E4-Orf6 were found to be more restricted. In addition to one common binding region (amino acids 262 to 326), p53 binding was affected by mutations at aa 180 and E4-Orf6 binding was affected by mutations at aa 143 (Yew and Berk, 1992; Rubenwolf et al., 1997).

Altogether these results indicate that it is difficult to separate the E1B-55K functions related to transformation (p53 binding) and late protein synthesis (Orf6

Here is described new E1 constructs that combine the high efficiency of transformation of one serotype with the serotype-specific complementation function of another serotype. These new constructs are used to transform primary human embryonic retinobladt cells and human amniocytes.

The Generation of pIG535, pIG635 and pIG735

Construct pIG535 contains the Ad5 E1A region and E1B promoter sequences linked to the Ad35 E1B sequences. Hereto, pIG270 (FIG. 15; see example 6) was digested with EcoRI and NcoI. The 5.3 kb vector fragment was then isolated from gel using the geneclean kit (BIO Inc. 101) according to the instructions of the manufacturer. Next, construct pIG.E1A.E1B (FIG. 13; see example 6) was digested with EcoRI and XbaI and the resulting 890 bp fragment was isolsted as above. A third fragment was generated by PRC amplification on pIG.E1A.E1B using the following primers:

5E1A-F: 5'-GAG ACG CCC GAC ATC ACC TG-3' (SEQ ID NO: 33).

5E1B-R: 5'-CAA GCC TCC ATG GGG TCA GAT GTA AC-3' (SEQ ID NO: 33).

The following PCR program was used: 94° C. for 2' followed by 30 cycles of 94° C. for 30", 60° C. for 30"and 72° C. for 1', and a final step at 72° C. for 10' to ensure blunt ends.

Figure 26:
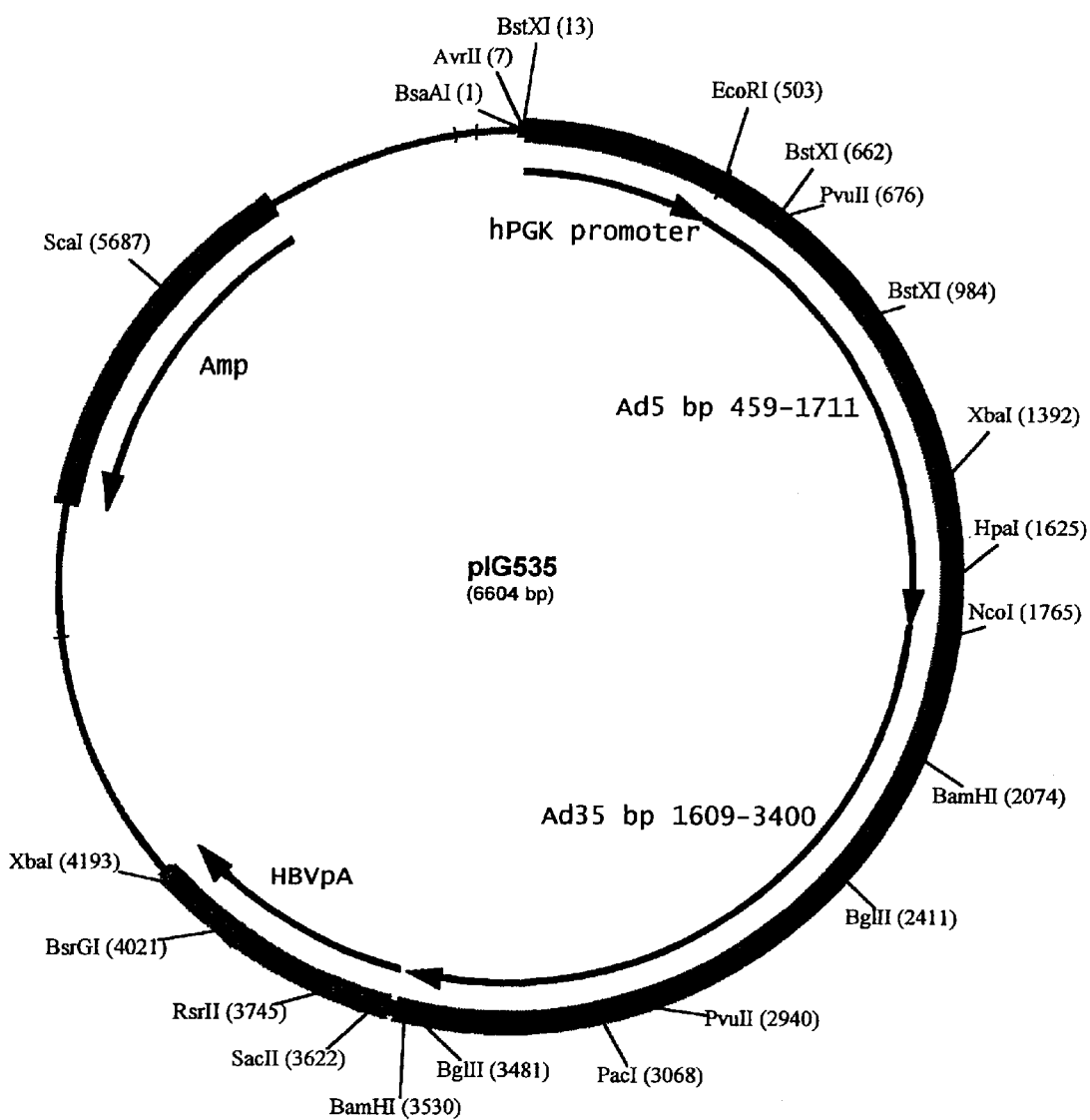
FIG. 26: Map of pIG535

The resulting 400 bp PCR fragment was digested with XbaI and NcoI. After gel isolation as above, the three fragments were ligated snd transformed into STBL-2bacteris. One colony containing all three fragments in the correct order was selected and designated pIG535 (FIG. 26).

Construct pIG635 contains the Ad5 E1A and a chimeric Ad5-Ad35 E1B region such that the 21K sequence is essentially from Ad5 and linked to the Ad35 E1B-55K sequences as far as not overlapping with the 21K sequences. First, part of the Ad5 E1 sequences are amplified by PCR using pIG.E1A.E1B as template and the following primers:

5AK: 5'-GAG CGA AGA AAC CCA TCT GAG-3' (SEQ ID NO: 34) and

2155R: 5'-GGT CCA GGC CGG CTC TCG G-3' (SEQ ID NO: 35).

Amplification is accomplished with Pwo DNA polymerase (Roche) according to manufacturer's instruction. The 210 bp fragments is then purified from the primer sequences using the PCR purification kit (Qiagen).

A second PCR fragment is amplified from pIG270 DNA as described above but with the following primers:

2155F: 5'-CCG AGA GCC GGC CTG GAC-3' (SEQ ID NO: 36) and

35F10: 5'-GCT CTA GAC CTG CAG GTT AGT CAG TTT CTT CTC CAC TG-3' (SEQ ID NO: 37).

The 1.3 kb amplified fragment is purified as above and mixed in a 1:1 molar ratio with the first PCR fragments. The mixture is then first subjected to a PCR reaction without the solution of primers using Pwo DNA polymerase and the following program: 94° C. for 2' and then 5 cycles of 94° C. for 30', 60° C. for 30', 72° C. for 90". Subsequently, primers 5AK and 35F10 are added at 0.6 μM concentration after which a last PCR amplifies a 1.5 kb fragment. Hereto, temperature was set as follows: 94° C. for 2', then 30 cycles of 94° C. for 30', 60° C. for 30' and 72° C. for 90', followed by a final step at 72° C. for 10' to ensure blunt ends. The resulting product is purified using the PCR purification kit (Qiagen) as above and digested with KpnI and SbfI (isoschixomer of Sse8387I). The digested DNA is then isolated from gel using the geneclean kit (BIO Inc., 101).

Figure 27:
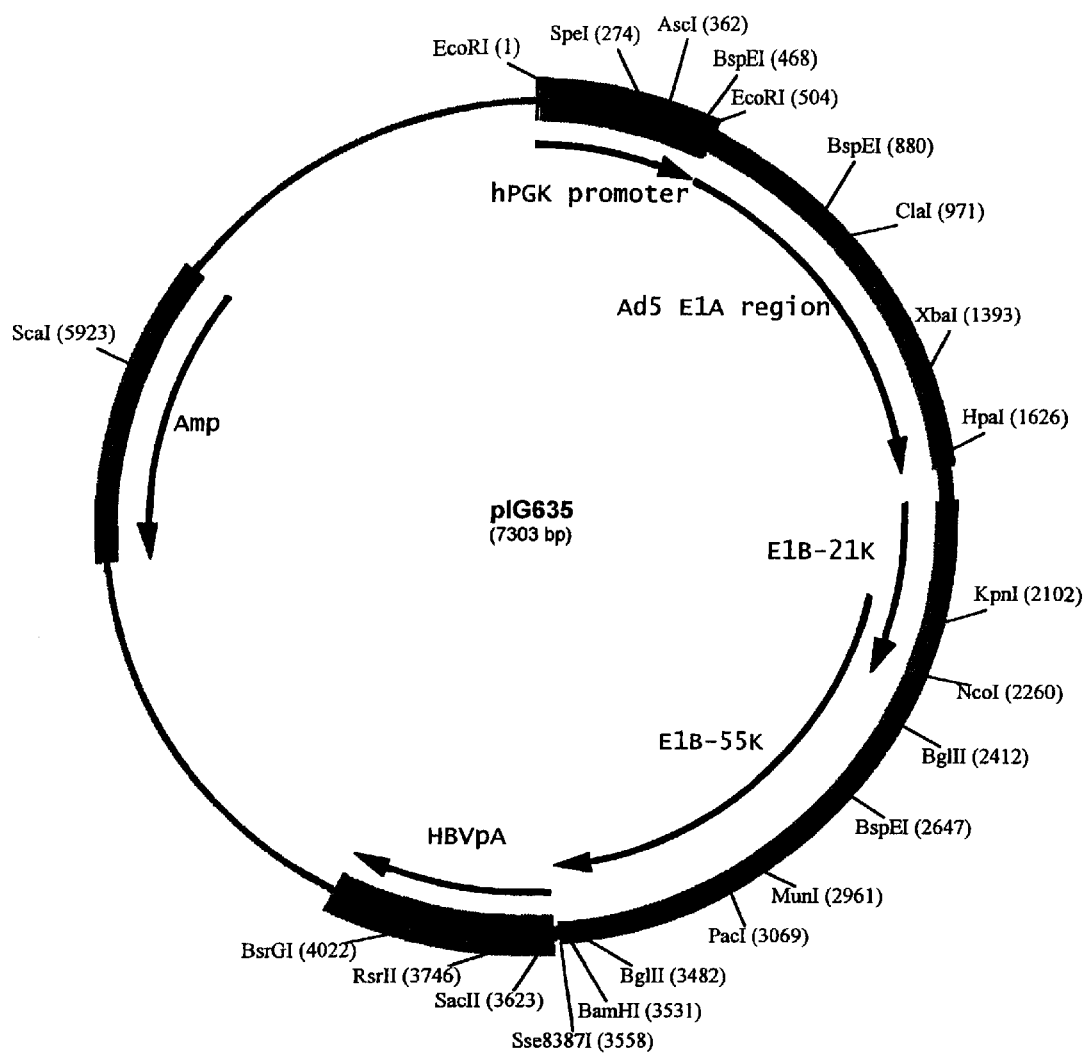
FIG. 27: Map of pIG635

Construct pIG.E1A.E1B is digested with KpnI and SbfI and the vector-containing fragment is isolated from gel as above. This fragment is ligated to the above prepared final PCR product and the ligation mixture is transformed into STBL-2 cells (Gibco, LTI) according to manufacturer's instructions. This gives construct pIG635 (FIG. 27).

Figure 28:
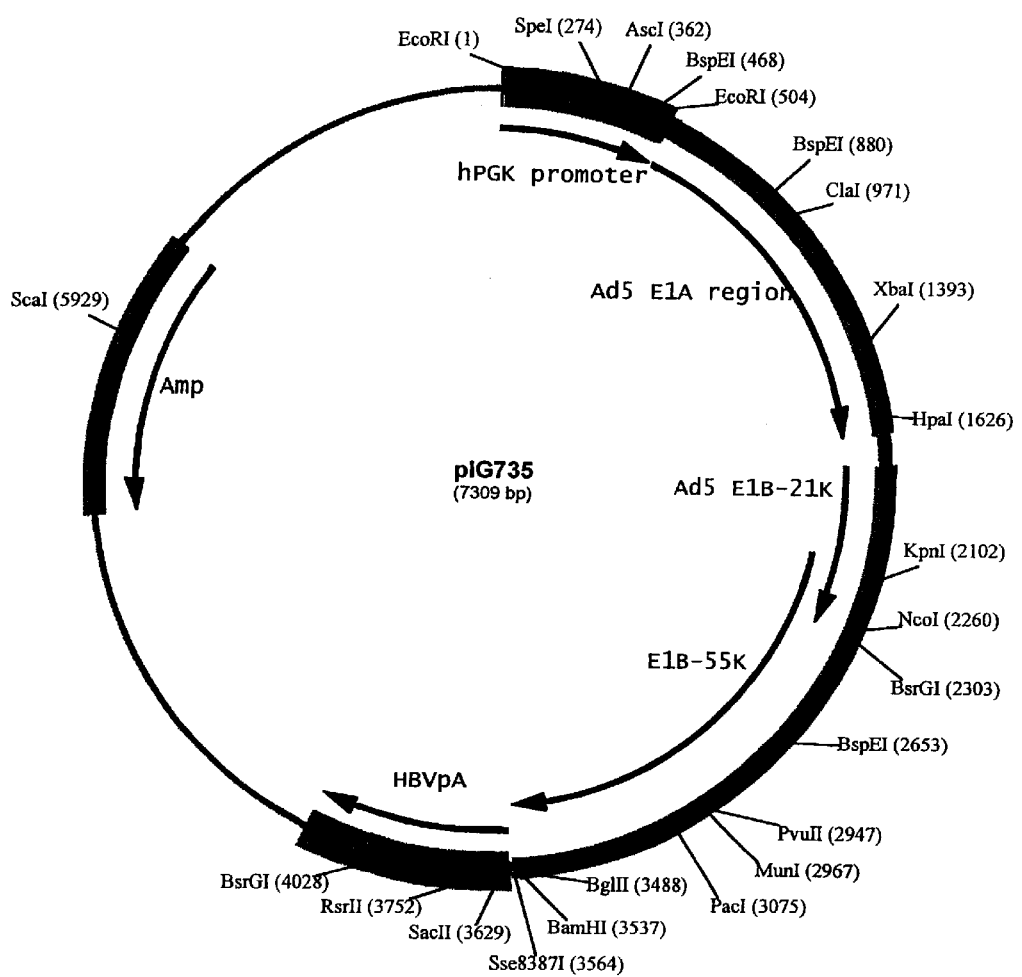
FIG. 28: Map of pIG735

In construct pIG735, the border between Ad5 derived sequences and Ad35 derived sequences is located more 3' than in construct pIG635. First, a BspEI site is introduced in the Ad5 sequence of construct pIg.E1A.E1B without changing the amino acid sequence. Hereto, Ad5 sequences from pIG.E1A.E1B are amplified using the following PCR primers: 5AK: (SEQ ID NO: 34) see above, and Bsp-R: 5'-GCT CTA GAC CTG CAG GGT AGC AAC AAT TCC GGA TAT TTA CAA G-3' (SEQ ID NO: 38). Amplification is accomplished using Pwo DNA polymerase (Roche) according to the manufacturer's instruction. The following PCR program is used: 94° C. for 2' followed by 30 cycles of 94° C. for 30', 60° C. for 30" and 72° C. for 30", and a final step at 72° C. for 10' to ensure blunt ends. The resulting 0.6 kb fragment is purified as above and digested with KpnI and SbfI and ligated to the above described KpnI/SbfI digested pIG.E1A.E1B vector fragment. Selection of colonies after transformation of STBL-2 bacteria (Life Techn. Inc.) gives construct pIG.E1Δ55K. pIG. E1Δ55K is then digested with SbfI and partially with BspEI. The 6.4 kb SbfI-partial BspEI digested vector fragment is then isolated from gel using the geneclean kit (BIO 101, Inc.). Next, pIG270 is digested with BspEI and SbfI and the resulting 915 bp fragment is isolated from gel as above. This fragment is then ligated to the above prepared SbfI/partial BspEI digested pIG.E1Δ55K vector fragment and transformed into STBL-2 competent cells. This gives construct pIG735 (FIG. 28). Clones are analysed by restriction enzyme digestion and sequencing to ensure correct ligation of the fragments. Constructs pIG535, pIG635 and pIG735 can be used to generate complementing cell lines from primary human cells as described in Example 6.

TABLE I

| Serotype | Elution [NaCl] mM | VP/ml | CCID50 | log$_{10}$ VP/CCID50 ratio |
|---|---|---|---|---|
| 1 | 597 | $8.66 \times 10^{10}$ | $5.00 \times 10^{7}$ | 3.2 |
| 2 | 574 | $1.04 \times 10^{12}$ | $3.66 \times 10^{11}$ | 0.4 |
| 3 | 131 | $1.19 \times 10^{11}$ | $1.28 \times 10^{7}$ | 4.0 |
| 4 | 260 | $4.84 \times 10^{11}$ | $2.50 \times 10^{8}$ | 3.3 |
| 5 | 533 | $5.40 \times 10^{11}$ | $1.12 \times 10^{10}$ | 1.7 |
| 6 | 477 | $1.05 \times 10^{12}$ | $2.14 \times 10^{10}$ | 1.7 |
| 7 | 328 | $1.68 \times 10^{12}$ | $2.73 \times 10^{9}$ | 2.4 |
| 9 | 379 | $4.99 \times 10^{11}$ | $3.75 \times 10^{7}$ | 4.1 |
| 10 | 387 | $8.32 \times 10^{12}$ | $1.12 \times 10^{9}$ | 3.9 |
| 12 | 305 | $3.64 \times 10^{11}$ | $1.46 \times 10^{7}$ | 4.4 |
| 13 | 231 | $4.37 \times 10^{12}$ | $7.31 \times 10^{8}$ | 3.8 |
| 15 | 443 | $5.33 \times 10^{12}$ | $1.25 \times 10^{9}$ | 3.6 |
| 16 | 312 | $1.75 \times 10^{12}$ | $5.59 \times 10^{8}$ | 3.5 |
| 17 | 478 | $1.39 \times 10^{12}$ | $1.45 \times 10^{9}$ | 3.0 |
| 19 | 430 | $8.44 \times 10^{11}$ | $8.55 \times 10^{7}$ | 4.0 |
| 20 | 156 | $1.41 \times 10^{11}$ | $1.68 \times 10^{7}$ | 3.9 |
| 21 | 437 | $3.21 \times 10^{11}$ | $1.12 \times 10^{8}$ | 3.5 |
| 22 | 365 | $1.43 \times 10^{12}$ | $5.59 \times 10^{7}$ | 3.4 |
| 23 | 132 | $2.33 \times 10^{11}$ | $1.57 \times 10^{7}$ | 4.2 |
| 24 | 405 | $5.12 \times 10^{12}$ | $4.27 \times 10^{8}$ | 4.1 |
| 25 | 405 | $7.24 \times 10^{11}$ | $5.59 \times 10^{7}$ | 4.1 |
| 26 | 356 | $1.13 \times 10^{12}$ | $1.12 \times 10^{8}$ | 4.0 |
| 27 | 342 | $2.00 \times 10^{12}$ | $1.28 \times 10^{8}$ | 4.2 |
| 28 | 347 | $2.77 \times 10^{12}$ | $5.00 \times 10^{7}$ | 4.7 |
| 29 | 386 | $2.78 \times 10^{11}$ | $2.00 \times 10^{7}$ | 4.1 |
| 30 | 409 | $1.33 \times 10^{12}$ | $5.59 \times 10^{8}$ | 3.4 |
| 31 | 303 | $8.48 \times 10^{10}$ | $2.19 \times 10^{7}$ | 3.6 |

TABLE I-continued

| Serotype | Elution [NaCl] mM | VP/ml | CCID50 | log$_{10}$ VP/CCID50 ratio |
|---|---|---|---|---|
| 33 | 302 | $1.02 \times 10^{12}$ | $1.12 \times 10^{7}$ | 5.0 |
| 34 | 425 | $1.08 \times 10^{12}$ | $1.63 \times 10^{11}$ | 0.8 |
| 35 | 446 | $3.26 \times 10^{12}$ | $1.25 \times 10^{11}$ | 1.4 |
| 36 | 325 | $9.26 \times 10^{12}$ | $3.62 \times 10^{9}$ | 3.4 |
| 37 | 257 | $5.86 \times 10^{12}$ | $2.8 \times 10^{9}$ | 3.3 |
| 38 | 337 | $3.61 \times 10^{12}$ | $5.59 \times 10^{7}$ | 4.8 |
| 39 | 241 | $3.34 \times 10^{11}$ | $1.17 \times 10^{7}$ | 4.5 |
| 42 | 370 | $1.95 \times 10^{12}$ | $1.12 \times 10^{8}$ | 4.2 |
| 43 | 284 | $2.42 \times 10^{12}$ | $1.81 \times 10^{8}$ | 4.1 |
| 44 | 295 | $8.45 \times 10^{11}$ | $2.00 \times 10^{7}$ | 4.6 |
| 45 | 283 | $5.20 \times 10^{11}$ | $2.99 \times 10^{7}$ | 4.2 |
| 46 | 282 | $9.73 \times 10^{12}$ | $2.50 \times 10^{8}$ | 4.6 |
| 47 | 271 | $5.69 \times 10^{11}$ | $3.42 \times 10^{7}$ | 4.2 |
| 48 | 264 | $1.68 \times 10^{12}$ | $9.56 \times 10^{8}$ | 3.3 |
| 49 | 332 | $2.20 \times 10^{12}$ | $8.55 \times 10^{7}$ | 4.4 |
| 50 | 459 | $7.38 \times 10^{12}$ | $2.80 \times 10^{9}$ | 3.4 |
| 51 | 450 | $8.41 \times 10^{11}$ | $1.88 \times 10^{8}$ | 3.7 |

Legend to Table I:

All human adenoviruses used in the neutralization experiments were produced on PER.C6 cells (Fallaux et al., 1998) and purified on CsCl as described in example 1. The CCID50 is shown for the 44 viruses used in this study and reflects the HPLC column is shown. Virus particles/ml (VP/ml) were calculated from an Ad5 standard. The titer in the experiment (CCID50) was determined on PER.C6 cells as described in Example 1 by titrations performed in parallel with the neutralization experiment. The CCID50 is shown for the 44 viruses used in this study and reflects the dilution of the virus needed to obtain CPE in 50% of the wells after 5 days. The ratio of VP/CCID50 is depicted in log$_{10}$ and is a measurement of the infectively of the different batches on PER.C6 cells.

TABLE II

AdApt35.LacZ viruses escape neutralization by human serum.

| | Human serum dilution | | | | | |
|---|---|---|---|---|---|---|
| Virus | no serum | 10x | 50x | 250x | 1250x | 6250x |
| AdApt5.LacZ moi: 5 VP/cell | 100% | 0% | 0% | 1% | 40% | 80% |
| AdApt35.LacZ 250 μl crude lysate | 100% | 100% | 100% | 100% | 100% | 100% |

TABLE III

The numbers of foci obtained with the different E1 expression constructs in BRK transformation experiments.
Average of # of foci/dish:

| Construct | 1 μgr | 5 μgr |
|---|---|---|
| Experiment 1 | | |
| pIG.E1A.E1B | nd | 60 |
| pIG.E1A.E1B | nd | 35 |
| pRSVAd35E1 | 0 | 3 |
| pIG.Ad35.E1 | 3 | 7 |
| Experiment 2 | | |
| pIG.E1A.E1B | 37 | nd |
| pIG.Ad35.E1 | nd | 2 |

TABLE III-continued

The numbers of foci obtained with the different E1 expression constructs in BRK transformation experiments.
Average of # of foci/dish:

| Construct | 1 μgr | 5 μgr |
|---|---|---|
| Experiment 3 | nd | 140 |
| pIG.Ad35.E1 | nd | 20 |
| pIG270 | nd | 30 |

References

Abrahamsen, K., Kong, H-L., Mastrangeli, A., Brough, D., Lizonova, A., Crystal, R. G. and Falck-Pedersen, E. (1997). Construction of an adenoovirus type 7a E1A⁻ vector. J. Virol. 71, 11, p8946–8951.

Babiss, L. E. and Ginsberg, H. S. (1984). Adenovirus type 5 early region 1b gene product is required for efficient shutoff of host protein synthesis. J. Virol. 50, p202–2122

Babiss, L. E., Ginsberg, H. S. and Darnell, J. J. (1985). Adenovirus E1B proteins are required for accumulation of late viral mRNA and for effects on cellular mRNA translation and transport. Mol. Cell. Biol. 5, p2552–2558.

Bemards,R., Houweling, A. Schrier, P. I., Bos, J. L. and van der Eb, A. j. (1982). Characterization of cells transformed by Ad5/Ad12 hybrid early region 1 plasmids. Virology 120, p422–432.

Bos, J. L., Polder, L. J., Bemards, R., Schrier, P., van den Elsen, P. J., van der Eb, A. J. and van Ormondt, H. (1981). The 2.2 kb mRNA of the E1B region of human adenovirus type 12 and 5 directs the synthesis of two major tumor antigens from different AUG triplets. Cell 12, p721–732.

Bridge, E. and Ketner, G. (1990). Interaction of adenoviral E4 and E1B products in late gene expression. Virology 174, p345–353.

Bridge, E., Medghalchi, S., Ubol, S., Leesong, M. and Ketner, G. (1993). Adenovirus early region 4 and viral DNA synthesis. Virology 193, p794–80.

Brough, D. E., Lizonova, A., Hsu, C., Kulesa, V. A. and Kovesdi, I. (1996). A gene tersfer vector-cell line system for complete functional complementation of of adenovirus early regions 1 and 4. J. Virol. 70, p6497–6501.

Fallaux, F. J., Kranenburg, O., Cramer, S. J., Houweling, A., van Ormondt, H., Hoeben, R. C. and van der Eb, A. J. (1996). Characterization of 911: a new helper cell line for the titration and propagation of early region 1-deleted adenoviral vectors. Hum. Gene Ther. 7 (2), p215–222.

Fallaux, F. J., Bout, A., van der Velde, I., van den Wollenberg, D. J., Hehir, K. M., Keegan, J., Auger, C., Cramer, S. J., van Ormondt, H., van der Ed, A. J., Valerio, D. and Hoeben, R. C. (1998). New helper cells and matched early region 1-deleted adenovirus vectors prevent generation of replication competent adenoviruses. *Hum. Gene Ther.* 9, 1909–1917.

Gallimore, P. H., Grand, R. J. A. and Byrd, P. J. (1986). Transformation of human embryo retinoblasts with simian virus 40, adenovirus and ras oncogenes. AntiCancer Res. 6, p499–508.

Gossen, M., and H. Bujard (1992) Tight control of gene expression in mammalian cells by tetracycline-responsive promoters. Proc. Natl. Acad. Sci. USA 89; 5547–5551.

Graham, F. O., Smiley, J., Russell, W. and Naim, R. (19770. Characteristics of a human cell line transformed by DNA from human adenovirus type 5. J. Gen. Virol. 36, p59–72.

Grand, R. J. A., Parkhill, J., Szestak, T., Rookes, S. M., Roberts, S. and Gallimore, P. H. (1999). Definition of a major p53 binding site on Ad2E1B58K protein and a possible nuclear localization signal on the Ad12E1B54K protein. Oncogene 18, p955–965.

Han, J., Sabbatini, P., Perez, D., Rao, L., Modha, D. and White, E. (1996). The E1B 19K protein blocks apoptosis by interacting with and inhibiting the p53-inducible and death-promoting Bax protein. Genes Dev. 10 (4), p461–477.

Jochemsen, A. G., Peltenburg L. T., te Pas, M. F., de Wit, C. M., Bos, J. L. and van der Eb, A. J. (1987). Activation of adenovirus 5 E1A transcription by region E1B in transformed primary rat cells. EMBO J. 6 (11), p3399–3405.

Leppard, K. N. and Shenk, T. (1989). The adenovirus E1B 55kd protein influences mRNA tranport via an intranuclear effect on RNA metabolism. EMBO J. 8, p2329–2336.

Pilder, S., Moore, M., Logan, J. and Shenk, T. (1986). The adenovirus E1B 55K transforming polyeptide modulates transport or cytopladmic stabilization of viral and host cell mRNAs. Mol. Cell. Biol. 6, p470–476.

Rao, L., Debbas, M., Sabbatini, P., Hockenbery, D., Korsmeyer, S. and White, E. (1992). The adenovirus E1A proteins induce apoptosis, which is inhibited by the E1B 19-kDa and Bcl-2 proteins. Proc. Natl. Acad. Sci. USA 89, p7742–7746.

Rubenwolf, S., Schütt, H., Nevels, M., Wolf, H. and Dobner, T. (1997). Structural analysis of the adenovirus type 5 E1B 55-kilodalton-E4orf6 protein complex. J. Virol. 71, p1115–1123.

Singer-Sam, J., Keith, D. H., Tani, K., Simmer, R. L., Shively, L., Lindsay, S., Yoshida, A. and Riggs, A. D. (1984). Sequence of the promoter region of the gene for human X-linked 3-phosphoglycerate kinase. Gene 32 (3), p409–417.

White, E. and Cipriani, R. (1990). Role of adenovirus E1B proteins in trandformation: Altered organization of intermediate filaments if transformed cells that express the 19-kilodalton protein. Mol. Cell. Biol. 10, p120–130.

White, E. (1995). Regulation of p53-dependent apoptosis by E1A and E1B. In: The molecular repertoire of adenoviruses III. Eds. Doerfler, W. and Böhm, P. Springer-Verlag Berlin Heidelberg 1995, p33–58.

White, E. (1996). Life, death, and the pursuit of apoptosis. Genes Dev. 10 (1), p1–15.

Yew, P. R., Kao, C. C. and Berk, A. J. (1990). Dissection of functional domains in the adenovirus 2 early region 1B 55K polypeptide by suppressor-linker insertional mutagenesis. Virology 179, p795–805.

Yew, P. R. and Berk, A. J. (1992). Inhibition of p53 transactivation required for transformation by adenovirus early region 1B protein. Nature 357, p82–85.

Simonsen, C. C. and Levinson, A.D. (1983). Analysis of processing and polyadenylation signal of the hepatites B virus surface antigen gene by using simian virus 40-hepatitis B virus chimeric plasmids. Mol. and Cell. Biol. 3 (12), p2250–2258.

Zantema, A., Fransen, J. A., Davis, O. A., Ramaekers, F. C., Vooijs, G. P., DeLeys, B. and van der Eb, A. J. (1985). Localization of the E1B proteins of adenovirus 5 in transformed cells, as revealed by interaction with monoclonal antibodies. Virology 142, p44–58.

Zantema, A. and van der Eb, A. J. (1995). Modulation of gene expression by adenovirus transformation, In: The moleculat repertoire of adenoviruses III. Eds. Doerfler, W. and Böhm, P. Springer-Verlag Berlin Heidelberg 1995, p1–23.

What is claimed is:

1. A packaging cell lene capable of complementing recombinant adenoviruses based on adenovirus serotype 35.

2. A packaging cell line capable of complementing recombinant adenoviruses bases on serotypes from Subgroup B, wherein said cell line is derived from primary, diploid human cells, said primary, diploid human cells being transformed by adenovirus serotype 35 E1 sequences either operatively linked on one DNA molecule or located on two separate DNA molecules, said sdequerces being operatively linked to regulatory seguences enabling transcription and translation of encoded proteins.

3. A packaging cell line capable of complementing recombinant adenoviruses bases on serotypes from Subgroup B, wherein said cell line is derived from primary, diploid human cells, said primary, diploid human cells being transformed by adenovirus E1 sequences either operatively linked on one DNA molecule or located on two separate DNA molecules, said sequences being operatively linked to regulatory seguences enabling transcription and translation of encoded proteins, wherein the primary, diploid human cells are transformed with chimeric E1 constructs comprising E1A and E1B sequences, wherein said chimeric E1 constructs consist of E1 sequences of a serotype that enables efficient transformation of primary human cells and E1B-55K sequences of any serotype of subgroup B and E1B-21K sequences from any serotype, which E1-deleted viruses of theat serotype, and wherein said E1B sequences comprise E1B-21K and E1B-55K sequences to propagate chimeric subgroup B adenoviruses.

4. The packaging cell line of claim 3 wherein the E1A region is derived from a subgroup C adenovirus and the E1B sequences are derived from adenovirus of subgroup B, more particular from adenovirus type 35.

5. The packaging cell line of claim 3 wherein the E1A sequences and the E1B-21K sequences are derived from a subgroup C adenovirus, and the E1B-55K sequences that do not overlap with the E1B-21K sequences are derived from an adenovirus of subgroup B.

6. The packaging cell line of claim 5 wherein the subgroup B adenovirus is type.

7. The packaging cell line of claim 3 wherein all E1 sequences are derived from a subgroup C adenovirus, except fro a part of the E1B-55K sequences that is necessary for serotype-specific complementation of an adenovirus subgroup B, said sequences being derived from said adenovirus subgroup B.

\* \* \* \* \*

UNITED STATES PATENT AND TRADEMARK OFFICE
CERTIFICATE OF CORRECTION

PATENT NO. : 6,492,169 B1
DATED : December 10, 2002
INVENTOR(S) : Ronald Vogels, Menzo Havenga and Majid Mehtali It is certified that error appears in the above-identified patent and that said Letters Patent is hereby corrected as shown below:

Title page,
Item [75] Inventors, after "Vogels," change "Linschoren" to -- Linschoten --; and after "Havenga," change "Alphen aas den Rijn" to -- Alphen aan den Rijn --
Item [57], ABSTRACT,
Line 1, change "complemention" to -- complementing --
Lines 3-4, after "preferably" at end of line 3 and before "human" at beginning of line 4, insert -- derived from primary, diploid human cells (e.g., primary human retinoblasts, primary --
Line 9, after "proteins." insert -- Also disclosed is a cell line derived from PER.C6 (ECACC deposit number 96022940), which cell expresses functional Ad35 E1B sequences. The Ad35-E1B sequences are driven by the E1B promoter and terminated by heterologous poly- adenylation signal. The new cell lines are useful for producing recombinant adenoviruses designed for gene therapy and vaccination. The cell lines can also be used for producing human recombinant therapeutic proteins such as human growth factors and human antibodies. In addition, the cell lines are useful for producing human viruses other than adenovirus such as influenza virus, herpes simplex virus, rotavirus, measles virus. --

Column 1,
Line 61, change "MRNA" to -- mRNA --

Column 2,
Lines 47, 52 and 53, change "particular" to -- particularly --

Column 3,
Line 17, change "neor" to -- $neo^r$ --
Line 22, change "AdS-E1" to -- Ad5-E1 --
Line 58, after "Example" and before "for" insert -- 1 --

Column 4,
Line 45, change "96-wells" to -- 96-well --
Line 58, after "further" insert -- use. --

Column 5,
Line 3, after "in" and before "(100" insert -- duplo --

UNITED STATES PATENT AND TRADEMARK OFFICE
CERTIFICATE OF CORRECTION

PATENT NO.    : 6,492,169 B1
DATED         : December 10, 2002
INVENTOR(S)   : Ronald Vogels, Menzo Havenga and Majid Mehtali It is certified that error appears in the above-identified patent and that said Letters Patent is hereby corrected as shown below:

Column 6,
Line 22, change "1 1" to -- 11 --
Line 33, change "calorimetric" to -- colorimetric --

Column 8,
Line 26, after "sera" and before "obtained" insert -- were --

Column 9,
Line 15, change "VP/mil)" to -- VP/ml --
Line 19, change "2.5 $\mu$l" to -- 2.5$\mu$l -- and change "3.2 $\mu$l" to -- 3.2$\mu$l --
Line 34, change "(+/-2)" to -- (+/- 2) --

Column 10,
Line 40, change "WO99/55 132" to -- WO99/55132 --

Column 11,
Lines 29 and 50, change "Agel" to -- AgeI --

Column 13,
Line 1, change "COC" to -- CGC --
Line 8, change "follow" to -- followed by 8 min. --
Line 23, change "0.6 lM" to -- 0.6 $\mu$M --
Line 36, change "(LTD)" to -- (LTI) --

Column 14,
Line 56, change "Ad3 5.E1" to -- Ad35.E1 --

Column 15,
Line 16, after "of" and before "94°" insert -- 30 sec. at --

Column 16,
Line 16, delete "1 $\mu$g pAdApt35.LacZ digested with PacI"
Line 38, change "virused" to -- viruses -- and change "cultures" to -- cultured --
Line 38, after "CPE" change "stained blue. To test for the" to -- found indicating the absence of --
Line 48, change "24-wells" to -- 24-well --
Line 49, change "wells" to -- 24-wells --
Lines 65 and 66, change "AdApt5.LasZ" to -- AdApt5.LacZ --

UNITED STATES PATENT AND TRADEMARK OFFICE
CERTIFICATE OF CORRECTION

PATENT NO. : 6,492,169 B1
DATED : December 10, 2002
INVENTOR(S) : Ronald Vogels, Menzo Havenga and Majid Mehtali It is certified that error appears in the above-identified patent and that said Letters Patent is hereby corrected as shown below:

Column 17,
Line 1, change "Ad3 5-based" to -- Ad35-based --
Line 41, change "Sapi" to -- SapI --

Column 18,
Line 30, change "Derivedfrom" to -- Derived From --
Line 43, change "lgr" to -- $\mu$gr --
Line 55, change "Following" to -- following --

Column 19,
Line 13, change "$\mu$mgr" to -- $\mu$gr --
Line 29, change "Derivedfrom" to -- Derived From --

Column 20,
Line 28, change "HindII" to -- HindIII --
Lines 31 and 36, change "pIX$\Delta$DE1A" to -- pIX$\Delta$E1A --
Line 37, change "6 $\mu$mgr" to -- 6 $\mu$gr --

Column 21,
Line 23, change "Hereto." to -- Hereto, --
Line 24, change "KB" to -- kb --
Line 35, change "(fmal" to -- (final --
Line 37, after "for" and before "and" insert -- 30" --
Line 41, delete "bold"
Line 48, after "possible" and before "delete" insert -- to --
Line 50, change "pIX$\Delta$TE1A" to -- pIX$\Delta$E1A --
Line 66, change "pBr.Ad35AsM" to -- pBr.Ad35$\Delta$sM --

Column 22,
Line 3, change "pBr.Ad35AE1A.AE1B" to -- pBr.Ad35$\Delta$ElA.$\Delta$E1B --
Line 25, change "pBr.Ad35ASM" to -- pBr.Ad35$\Delta$SM --
Line 60, change "thereof" to -- thereof. --

UNITED STATES PATENT AND TRADEMARK OFFICE
CERTIFICATE OF CORRECTION

PATENT NO. : 6,492,169 B1
DATED : December 10, 2002
INVENTOR(S) : Ronald Vogels, Menzo Havenga and Majid Mehtali It is certified that error appears in the above-identified patent and that said Letters Patent is hereby corrected as shown below:

Column 23,
Line 18, change "neor" to -- neo$^r$ --
Lines 18-19, after "gene" change "fragment on gel and isolated using the geneclean kit (BIO 101, Inc.). After religation of" to -- is driven by a hPGK promoter/HBVpA cassette. --
Line 22, change "HindII" to -- HindIII --
Line 44, change "lateer" to -- later --
Line 45, change "wew" to -- were --
Line 56, after "E1B" and before "with ScaI" insert -- genes are expressed from a heterologous promoter (hPGK) and that also contains a neomycin resistance expression cassette. To avoid instability of the plasmid due to recombination events on homologous sequences, the RSV promoter drives the neo$^r$ gene. To achieve this, construct pRSVhbv.Neo (described in Example 5, FIG. 12) was digested --
Lines 60-66, after "with" delete "To achieve this,"
Lines 61-65 delete lines in their entirety
Line 66, delete "101, Inc.). Next, pRSVhbvNeo was digested with"

Column 24,
Lines 1-2, change "above and religated to give pIG270delEIA. This construct was digested with AvrII and" to -- HBVpA, vector and part of the Ampicilin gene was isolated as above. The two fragments --
Line 6, delete "Next, pRSVneo4 was digested with BglII, blunted with"
Line 7, change "enzyme," to -- enzyme. The vector containing fragment was isolated from gel as described --
Line 16, change "site at nucl 2949 in FIG. 24)." to -- were analysed. One clone that contained both expression cassettes in the same orientation --Line 17, change "choosen" to -- chosen --
Lines 18-19, change "coding region of Ad35.E1B-21K. Hereto, both the E1A and E1B-21K sequences are first" to -- that an extra BglII site was present probably due to an incomplete Klenow reaction (BglII --
Line 31, change "Agel" to -- AgeI --
Line 33, change "sre" to -- are --
Line 40, change "descrided" to -- described --
Line 43, change "forther sigested" to -- further digested --
Line 44, change "PRC" to -- PCR --
Line 50, change "Scal" to -- ScaI --
Line 64, change "differint" to -- different --
Line 64, change "encoded by the" to -- in lytic infection and in --
Line 66, change "Ed" to -- Eb --

UNITED STATES PATENT AND TRADEMARK OFFICE
CERTIFICATE OF CORRECTION

PATENT NO. : 6,492,169 B1
DATED : December 10, 2002
INVENTOR(S) : Ronald Vogels, Menzo Havenga and Majid Mehtali It is certified that error appears in the above-identified patent and that said Letters Patent is hereby corrected as shown below:

Column 25,
Line 12, change "fuictions" to -- functions --
Line 31, after "by" and before "fragment" insert -- the HBVpA. The hPGK promoter constitutes a HincII-EcoRI fragment of the promoter sequence described by Singer-Sam et al. (1984). The HBVpA is located in a BamHI-BglII --
Lines 33-36, delete "sequence described by Singer-Sam et al. (1984). The HBVpA is located in a BaMHI-BglII fragment of the Hepatitis B virus genome (Simonsen and Levinson, 1983; see also"
Line 41, change "HbVpA" to -- HBVpA --
Line 47, change "(Bemards" to -- (Bernards --
Line 49, after "in" and before "subgroups" insert -- transformation efficiency of E1 sequences observed for adenoviruses from different --
Line 50, after "genes" and before "proteins" insert -- suggested that the efficiency of transformation of BRK cells was determined by the E1A --
Line 50, change "(Bemards" to -- (Bernards --
Line 53, after "If" and before "function" insert -- these functions are related to the regulation of mRNA distribution or another late viral --
Line 68, after "(Orf6" insert -- binding). --

Column 26,
Line 5, change "retinobladt" to -- retinoblast --
Line 16, change "isolsted" to -- isolated --
Line 18, change "PRC" to -- PCR --
Line 21, change "33)." to -- 32) and --
Line 31, change "2bacteris" to -- 2 bacteria --
Lines 33 and 37, change "AdS" to -- Ad5 --
Lines 45 and 54, change "fragments" to -- fragment --
Line 56, change "solution" to -- addition --
Line 58, change "30'" (both occurrences) to -- 30" --
Line 62, change "30'" (both occurrences) to -- 30" --
Line 62, change "90'" to -- 90" --
Line 66, change "isochixomer" to -- isochizomer --

UNITED STATES PATENT AND TRADEMARK OFFICE
CERTIFICATE OF CORRECTION

PATENT NO. : 6,492,169 B1
DATED : December 10, 2002
INVENTOR(S) : Ronald Vogels, Menzo Havenga and Majid Mehtali It is certified that error appears in the above-identified patent and that said Letters Patent is hereby corrected as shown below:

Column 27,
Line 1, change "Kpnl" to -- KpnI -
Line 10, change "pIg." to -- pIG. --
Line 18, after "for" change "30'" to -- 30" --

Column 28,
Lines 27-28, change "CCID50 is shown for the 44 viruses used in this study and reflects" to --NaCI concentration at which the different serotypes eluted from --

Column 29,
Table III, after "Experiment 3" delete "nd" and "140" and after "Experiment 3" and on its own line in columns lining up with entries below, insert -- pIG.Ela.E1B --, -- nd --, and -- 140 --
Line 26, change "Bemards" to -- Bernards --
Line 30, change "Bemards" to -- Bernards --
Line 40, change "80" to -- 801 --
Line 42, change "tersfer" to -- transfer --
Line 43, delete "of" (first occurrence)
Line 52, change "Ed" to -- Eb --
Line 64, change "Naim" to -- Nairn --
Line 65, change "19770" to -- 1977) --

Column 30,
Line 15, change "tranport" to -- transport --
Line 18, change "polyeptide" to -- polypeptide --
Line 19, change "cytopladmic" to -- cytoplasmic --
Line 36, change "trandformation" to -- transformation --
Line 53, change "signal" to -- signals -- and change "hepatites" to -- hepatitis --

UNITED STATES PATENT AND TRADEMARK OFFICE
CERTIFICATE OF CORRECTION

PATENT NO.    : 6,492,169 B1
DATED         : December 10, 2002
INVENTOR(S)   : Ronald Vogels, Menzo Havenga and Majid Mehtali It is certified that error appears in the above-identified patent and that said Letters Patent is hereby corrected as shown below:

Column 71,
Line 40, change "lene" to -- LINE --
Line 43, change "bases" to -- based --
Line 48, change "sdequerces" to -- sequences --
Line 49, change "seguences" to -- sequences --
Line 52, change "bases" to -- based --
Line 58, change "seguences" to -- sequences --

Column 72,
Line 40, after "which" and before "E1-deleted" insert -- E1B sequences provide serotype-specific EIB function(s) that enable(s) efficient propagation of --
Line 41, change "theat" to -- the E1B --
Line 54, after "is" and before "type" insert -- adenovirus -- and after "type" and before the period insert -- 35 --
Line 57, change "fro" to -- for --
Line 58, after "adenovirus" and before "sub-" insert -- of --
Line 59, after "adenovirus" insert -- of --

Signed and Sealed this

Fifteenth Day of April, 2003

JAMES E. ROGAN
*Director of the United States Patent and Trademark Office*